United States Patent
Malcuit et al.

(10) Patent No.: US 9,663,792 B2
(45) Date of Patent: May 30, 2017

(54) PLANT MITOCHONDRIA TRANSFORMATION METHOD

(75) Inventors: Isabelle Malcuit, London (GB); Alexander Sorokin, London (GB)

(73) Assignee: Algentech SAS, Envry (FR)

(*) Notice: Subject to any disclaimer, the term of this patent is extended or adjusted under 35 U.S.C. 154(b) by 920 days.

(21) Appl. No.: 13/131,081

(22) PCT Filed: Nov. 25, 2009

(86) PCT No.: PCT/GB2009/002755
§ 371 (c)(1),
(2), (4) Date: Aug. 17, 2011

(87) PCT Pub. No.: WO2010/061187
PCT Pub. Date: Jun. 3, 2010

(65) Prior Publication Data
US 2011/0296551 A1    Dec. 1, 2011

(30) Foreign Application Priority Data
Nov. 25, 2008   (GB) .................................. 0821515.4

(51) Int. Cl.
*C12N 15/82*   (2006.01)

(52) U.S. Cl.
CPC ..... *C12N 15/8201* (2013.01); *C12N 15/8214* (2013.01); *C12N 15/8217* (2013.01); *C12N 15/8257* (2013.01); *C12N 15/8258* (2013.01); *C12N 15/8289* (2013.01)

(58) Field of Classification Search
None
See application file for complete search history.

(56) References Cited

U.S. PATENT DOCUMENTS

| | | | |
|---|---|---|---|
| 2,561,330 A * | 7/1951 | Ayers | ........................... 554/198 |
| 2003/0104352 A1 * | 6/2003 | Lambowitz et al. | ............. 435/4 |
| 2007/0180582 A1 | 8/2007 | Kim et al. | |
| 2008/0222750 A1 * | 9/2008 | Khan | ........................... 800/278 |

FOREIGN PATENT DOCUMENTS

| | | |
|---|---|---|
| CA | 2 272 788 A1 | 12/2000 |
| WO | 02/066661 A1 | 8/2002 |

OTHER PUBLICATIONS

Val et al (Nuc. Acid. Res., 29(21), pp. 9262-9274, 2011).*
Cui et al (JMB, 340(2), pp. 211-231, 2004).*
Xiang et al (J. Virol., 80(16), pp. 7952-7964, 2006).*
Loos, Holger, "Transformation der Plastiden und Mitochondrien bei höheren Pflanzen—Selektive Marker und Einsatzmöglichkeiten", Dissertation der Fakultät fur Biologie der Ludwig-Maximilian-Universität München, 2004.
Small, Ian, et al., "In vivo import of a normal or mutagenized heterologous transfer RNA into the mitochondria of transgenic plants: towards novel ways of influencing mitochondrial gene expression", The EMBO Journal, 1992, pp. 1291-1296, vol. 11, No. 4.
Logan, David C., et al., "Mitochondria-targeted GFP highlights the heterogeneity of mitochondrial shape, size and movement within living plant cells", Journal of Experimental Botany, May 2000, pp. 865-871, vol. 51, No. 346.
Tarassov, Ivan, et al., "Import of Nuclear DNA-Encoded RNAs into Mitochondria and Mitochondrial Translation", Cell Cycle, Oct. 2007, pp. 2473-2477, vol. 6, No. 20.

* cited by examiner

*Primary Examiner* — David T Fox
*Assistant Examiner* — Stephen Uyeno
(74) *Attorney, Agent, or Firm* — Sughrue Mion, PLLC

(57) ABSTRACT

Method for heterologous RNA species and protein production in plant cell mitochondria comprising introducing into plant cells nucleic acid components that encode heterologous proteins/RNAS under the control of promoters operative in mitochondria, vectors, host cells, plants and uses thereof.

17 Claims, 6 Drawing Sheets

PLANT MITOCHONDRIA TRANSFORMATION METHOD

CROSS REFERENCE TO RELATED APPLICATIONS

Figure 1:
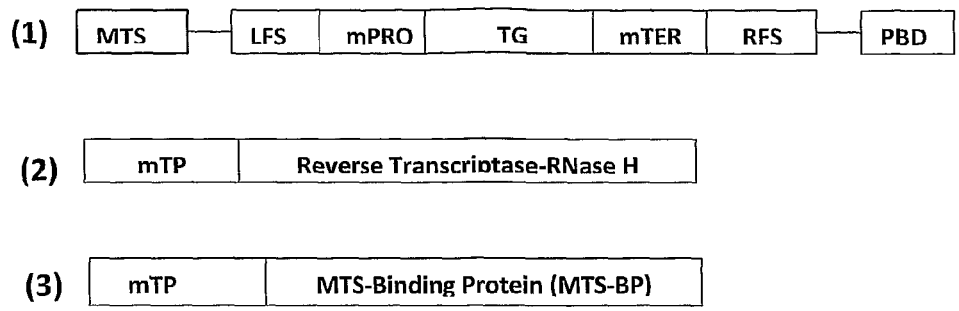

This application is a National Stage of International Application No. PCT/GB2009/002755 filed Nov. 25, 2009, which claims priority from British Patent Application No. 0821515.4 filed Nov. 25, 2008, the contents of all of which are incorporated herein by reference in their entirety.

The present invention relates to a method for producing heterologous or exogenous RNA species in plant cell material such as genetically transformed plant cells in culture, plant tissue and plants derived from genetically transformed plant cells. In particular, the method relates to a more efficient method for producing RNA species and/or heterologous or exogenous proteins in mitochondria comprised in plant cell material, the genetic material required therefor, such as DNA and RNA, vectors, host cells, methods of introduction of genetic material into plant cells, plant cells comprising genetically modified mitochondria, genetically modified mitochondria and uses thereof.

A disadvantage of prior art plant mitochondrion transformation methods is that the transformation efficiency in terms of numbers of transformed mitochondria per cell tends to be low. Furthermore, the amount of exogenous protein expressed from the mitochondria tends to be low as does the amount of exogenous protein produced per cell. A further disadvantage of prior art methods is that the delivery of genetic information into the mitochondria tends to be erratic in the sense that the delivery mechanisms employed rely on chance for the successful delivery of genetic information, such as RNA, into the mitochondrial genome. Prior art methods do not rely on efficient endogenous cellular processes for the transfer of RNA into the mitochondrial genome, subsequent reverse transcription and recombination of it within the mitochondrial genome, and where appropriate, followed by expression of protein of interest therefrom. As such, prior art processes for genetically modifying the mitochondrion are generally inefficient. These and other disadvantages of prior art mitochondrion transformation technology will become apparent from the foregoing description.

The present inventors have found that by using or adapting endogenous cellular processes for the transfer of polynucleotide sequences, such as RNAs, from the cytoplasm to mitochondria in the plant cell, polynucleotide sequences derived from nuclear transformation of the nucleus of a plant cell can be efficiently transferred or targeted to the mitochondrial genome within a plant cell that is so transformed, and expressed more efficiently in the mitochondrion as described herein. Furthermore, it is apparent that once the mitochondrion is transformed with sequences of the invention, it is not necessary for the nuclear encoded trangenes that are required for the initial transformation of mitochondria to remain in the nuclear genome. As a consequence, the nuclear encoded transgenes can be removed through deliberate or natural segregation in subsequent generations of plants. For the purposes of the present invention the terms "mitochondrion" and "mitochondria" and "mitochondrion population" are used interchangeably, as are the terms "plant cell" and "plant cells", unless context demands otherwise. By employing or adapting endogenous cellular processes for the transfer of RNA derived from polynucleotide sequences introduced to the nucleus to the mitochondrion genome, as described herein, the method of the invention is considered to be unique over prior art methods for the generation of plant cells or plants possessing genetically modified mitochondria. The mitochondrion population of the plant cell is constantly bombarded by RNA that is derived from the nucleus of the cell, which is carried over the mitochondrial membrane and into the mitochondrial matrix where it is reverse transcribed, integrated into the genome and then transcribed, resulting in the generation of RNA from which proteins of interest may be expressed.

There exists a need for a more efficient mitochondrion transformation method for the production of RNAs, and where required, proteins of interest in the mitochondrion in transformed plant cells and plant tissue derived therefrom. Furthermore, there exists a need for a more efficient nucleic acid based technology, for example an RNA-based technology to knock out genes located within the mitochondria.

The basis for the present invention, which does not appear to have been realised in the prior art, is the supply of a mitochondrial transformation system comprising nucleic acid sequences that encode: i) a plant mitochondria transformation unit (MTU); ii) a reverse transcriptase fused to a plant-derived mitochondrion transit peptide sequence; and iii) an RNA binding protein fused to a plant-derived mitochondrion transit peptide. Such mitochondrial fusion systems do not appear to have been described or alluded to in the prior art. Further simplified modifications of this kind of mitochondrion transformation unit include those that comprise nucleic acid sequences that encode i) a mitochondrion transformation unit (MTU; a mitochondrion translocation sequence (MTS-5'), fused to the 5' end of the MTU; a further mitochondrion translocation sequence (MTS-3') fused to the 3'-end of the MTU; and a primer binding domain designed for reverse transcription in the mitochondria using mitochondrion tRNA-Met (PBD-MIT). By placing the PBD-MIT next to the 3' end of the MTS-3', that is to say, outside of the LtrB intron as depicted in FIG. 8(A), the LtrA protein is able to function as both a translocation protein and as a source of reverse transcriptase. In such a variant, there is no need to introduce a second gene for reverse transcriptase functionality. In a second variant of this system, where the PBD (PBD-CYT) is designed to interact with endogenous cytoplasmic tRNA-Met, the PBD may be located adjacent to the 3'-end of the MTU and a mitochondrion translocation sequence is fused to it downstream. In this second variant, where a PBD is employed that is able to bind with cytoplasmic tRNA-Met as primer, reverse transcription is initiated by endogenous reverse transcriptase in the cytoplasm using cytoplasmic tRNA-Met. Thus, the second variant of the system does not require the co-delivery of a reverse transcriptase nucleic acid sequence to the mitochondria. The use of such mitochondrial transformation systems provides for an improved yield of RNA or protein of interest (depending on design), from mitochondrial sources than has been hitherto achievable in the prior art.

According to the present invention there is provided a method of transforming a plant cell that comprises:
1) introducing into the said plant cell a first nucleic acid sequence that comprises a plant nuclear promoter operably linked to a first nucleic acid sequence that comprises a plant mitochondrion transgene cassette, a plant mitochondrion translocation sequence, and a primer binding domain;
2) introducing into the said plant cell a second nucleic acid sequence that encodes for a translocation sequence (MTS) binding protein fused to a plant mitochondrion transit peptide wherein said second nucleic acid sequence is operably linked to a plant nuclear promoter; and 3) introducing into the said plant cell a third nucleic acid sequence that encodes for a reverse transcriptase protein fused to a plant mitochondrion transit peptide wherein the third nucleic acid sequence is operably linked to a plant nuclear promoter that drives expression in a plant cell nucleus.

As another aspect of the invention there is provided a plant cell obtained by the method of the invention as described hereinabove and in further refinements of the method as described hereinbelow.

In a further aspect of the invention there is provided a method of transforming a plant cell that comprises introducing into the plant cell a nucleic acid sequence that comprises a plant nuclear promoter operably linked to a first nucleic acid sequence that comprises a first mitochondrion translocation sequence (MTS-5') fused to the 5'-end of the mitochondrion transformation unit (MTU), a second mitochondrion translocation sequence (MTS-3') fused to the 3' end of the MTU, and a primer binding domain designed for reverse transcription in mitochondria, using tRNA-Met located within the mitochondria. The two mitochondrion translocation sequences may be the same or different depending on design. In this variant reverse transcription can be effected when the PBD is located downstream of the MTU, that is to say 3' to a mitochondrion translocation sequence (MTS-3'). Such a combination allows both translocation of the MTU into the mitochondrion and reverse transcription of the MTU by the LtrA protein and does not require the co-delivery of a nucleic acid sequence for reverse transcriptase functionality.

In a still further variant of the methods aspect of the invention, there is provided a method of transforming a plant cell that comprises introducing into the plant cell a nucleic acid sequence that comprises a plant nuclear promoter operably linked to a first nucleic acid sequence that comprises a first mitochondrion translocation sequence (MTS-5') fused to the 5'-end of the mitochondrion transgene unit (MTU), a second mitochondrion translocation sequence (MTS-3') fused to the 3'-end of a primer binding domain for binding tRNA-Met as primer that uses tRNA-Met that is located within the cytoplasm. Thus, the primer binding domain is capable of utilising native, endogenous reverse transcriptase located in the cytoplasm (PBD-CYT) for reverse transcription using cytoplasmic tRNA-Met as primer. Again, the two mitochondrion translocation sequences may be the same or different depending on design. In this variant, there is also no need to co-deliver a nucleic acid sequence to the mitochondria for reverse transcriptase functionality.

As another aspect of the invention there is provided a plant cell obtained by any one of the methods of the invention as described herein above.

In a further aspect of the invention there is provided a method of producing at least a heterologous or exogenous RNA species in a plant that comprises:
1) introducing into a regenerable plant cell a nucleic acid sequence that comprises a plant nuclear promoter operably linked to a first nucleic acid sequence that comprises a plant mitochondrion transgene cassette, a plant mitochondrion translocation sequence, and a primer binding domain;
2) introducing into the said regenerable plant cell a second nucleic acid sequence that encodes for a mitochondrion translocation sequence binding protein fused to a plant mitochondrion transit peptide wherein said second nucleic acid sequence is operably linked to a plant nuclear promoter; and
3) introducing into the said regenerable plant cell a third nucleic acid sequence that encodes for a reverse transcriptase protein fused to a plant mitochondrion transit peptide wherein the third nucleic acid sequence is operably linked to a plant nuclear promoter;
4) growing said regenerable plant cell of steps 1) to 3);
5) selecting a plant cell of (4) wherein the transgene comprised within the plant mitochondrion transgene cassette is integrated into the mitochondrial genome;
6) regenerating a plant from the plant cell of (5); and
7) growing the plant of (6).

Preferably, the plant obtained according to the above method is grown under conditions wherein the said heterologous or exogenous RNA species encoded by the transgene integrated into the mitochondrion is expressed as heterologous or exogenous protein.

Again, and with reference to the method of obtaining a plant above, the skilled addressee will appreciate that where there are native proteins present in a plant cell that are capable of binding to a mitochondrion translocation sequence, and which are capable of translocating RNA nucleic acid sequences to the mitochondrion, such as viroid proteins, step 2) of the said method may be omitted. In such an instance, there is provided a method of producing at least a heterologous or exogenous RNA species in a plant that comprises:
1) introducing into a regenerable plant cell a nucleic acid sequence that comprises a plant nuclear promoter operably linked to a first nucleic acid sequence that comprises a mitochondrion transgene cassette, a mitochondrion translocation sequence (PTS), and a primer binding domain (PBD);
2) introducing into the said regenerable plant cell a second nucleic acid sequence that encodes for a reverse transcriptase protein fused to a second mitochondrion transit peptide wherein the second nucleic acid sequence is operably linked to a plant nuclear promoter that drives expression in a plant cell;
3) growing said regenerable plant cell of steps 1) and 2);
4) selecting a plant cell of (3) wherein the transgene comprised within the mitochondrion transgene cassette is integrated into the plastid genome;
5) regenerating a plant from the plant cell of (4); and
6) growing the plant of (5).

In a further aspect of the invention there is provided a method of producing at least a heterologous or exogenous RNA species in a plant that comprises:
1) introducing into a regenerable plant cell a nucleic acid sequence that comprises a plant nuclear promoter operably linked to a first nucleic acid sequence that comprises a first mitochondrion translocation sequence (MTS-5') fused to the 5'-end of the mitochondrion transgene or transfromation unit (MTU), a second mitochondrion translocation sequence (MTS-3') fused to the 3'-end of the MTU, and a primer binding domain for reverse transcription in mitochondria;
2) growing said regenerable plant cell of step 1);
3) selecting a plant cell of (2) wherein the transgene comprised within the mitochondrion transgene cassette is integrated into the mitochondrion genome;
4) regenerating a plant from the plant cell of (3); and
5) growing the plant of (4).

The primer binding domain is designed for reverse transcription in the mitochondria (PBD-MIT), using tRNA-Met as primer that are located within the mitochondria. The two mitochondrion translocation sequences may be the same or different depending on design.

In a further variant of this aspect of the invention there is provided a method of producing at least a heterologous or exogenous RNA species in a plant that comprises:

1) introducing into a regenerable plant cell a nucleic acid sequence that comprises a plant nuclear promoter operably linked to a first nucleic acid sequence that comprises a first mitochondrion translocation sequence (MTS-5') fused to the 5'-end of the mitochondrion transgene unit (MTU), a second mitochondrion translocation sequence (MTS-3') fused to the 3'-end of a primer binding domain for binding tRNA-Met as primer that uses tRNA-Met that is located within the cytoplasm.
2) growing said regenerable plant cell of step 1);
3) selecting a plant cell of (2) wherein the transgene comprised within the mitochondrion transgene cassette (MTU) is integrated into the mitochondrion genome;
4) regenerating a plant from the plant cell of (3); and
5) growing the plant of (4).

The primer binding domain in the above variant is capable of utilising native, endogenous reverse transcriptase located in the cytoplasm (PBD-CYT) for reverse transcription using cytoplasmic tRNA-Met as primer. Again, the two mitochondrion translocation sequences may be the same or different depending on design.

Naturally, the person skilled in the art will understand that the plant nuclear promoter by being operably linked to the nucleic acid sequences provided for herein drives expression of such sequences in the plant nucleus.

The "plant mitochondrion transgene cassette" comprises a left flanking sequence (LFS) and a right flanking sequence (RFS) which are used for homologous recombination of the cassette into the mitochondrial genome. In between the LFS and RFS are located at least one mitochondrion specific promoter sequence (mPRO) and at least one mitochondrion specific terminator (mTER) sequence which in turn flanks at least one isolated gene or isolated nucleic acid sequence of interest, such as a recombinant DNA sequence (e.g. cDNA) or an introduced native DNA sequence. The LFS and RFS may include the mPRO and mTER sequences respectively, if for example, the isolated nucleic acid of interest is fused to a native mitochondrial nucleic acid of interest. Thus, the promoter and the terminator sequences are not necessarily included within the LFS or RFS respectively per se, or between the LFS and RFS if a transgene is inserted into the mitochondrial genome as a cistron unit or if a transgene is translationally fused to a native gene.

In such an instance, when a transgene is fused to a native mitochondrial coding sequence it is after the transformation event has taken place that the promoter may be found upstream of the sequence that is homologous to the LFS in the mitochondrial genome and is available to drive expression of the gene fused to the transgene of interest. For the purposes of the present invention "transgene" includes isolated nucleic acid sequences that may ultimately give rise to the expression of proteins or peptides of interest in the mitochondrion as herein described. Thus, the isolated nucleic acid sequence may be one that gives rise to an RNA sequence of interest which may not encode or give rise to the expression of a translatable product, or the isolated nucleic acid sequence may give rise to an RNA sequence that does encode or give rise to the expression of a translatable product such as a protein or peptide of interest. The person skilled in the art will also appreciate that the transgene that is carried on the isolated nucleic acid may also be designed to give rise to an RNA sequence that gives rise to the expression of a translatable product or products, and untranslatable RNAs. Such RNAs that do not give rise to the expression of proteins may give rise to RNA sequences that contain deletions or other mutations and these may find use as research tools for studying gene function in the mitochondrion. Where the "transgene" gives rise to the expression of proteins or peptides, suitable transgenes of interest include plant proteins capable of conferring desired traits to plant crops, and pharmaceutical proteins for use in mammals, including man, such as insulin, preproinsulin, proinsulin, glucagon, interferons such as α-interferon, β-interferon, γ-interferon, blood-clotting factors selected from Factor VII, VIII, IX, X, XI, and XII, fertility hormones including luteinising hormone, follicle stimulating hormone growth factors including epidermal growth factor, platelet-derived growth factor, granulocyte colony stimulating factor and the like, prolactin, oxytocin, thyroid stimulating hormone, adrenocorticotropic hormone, calcitonin, parathyroid hormone, somatostatin, erythropoietin (EPO), enzymes such as β-glucocerebrosidase, haemoglobin, serum albumin, collagen, biotic and abiotic stress proteins, such as insecticidal and insect toxic proteins, for example from, or derived from *Bacillus thuringiensis*, nematicidal proteins, herbicide resistance proteins, (e.g. to glyphosate), salt-tolerance proteins, drought tolerant proteins, proteins or RNA molecules that are capable of conferring cytoplasmic male sterility to plant breeding lines; nutritional enhancement proteins involved in the biosynthesis of phenolics, starches, sugars, alkaloids, vitamins, and edible vaccines, and the like. Furthermore, the method of the invention can be used for the production of specific monoclonal antibodies or active fragments thereof and of industrial enzymes or active fragments thereof.

All proteins mentioned hereinabove are of the plant and human type. Other proteins that are contemplated for production in the present invention include proteins for use in veterinary care and may correspond to animal homologues of human proteins, such as the human proteins mentioned hereinabove.

In a further aspect of the invention there is provided a plant cell that comprises mitochondria that are permanently transformed with an exogenous or a heterologous nucleic acid sequence that encodes for a protein or RNA of interest. Suitable proteins and peptides and nucleic acids of interest are provided herein. Certain heterologous nucleic acids of interest are useful in conferring cytoplasmic male sterility to plant breeding lines (for example, the petunia mitochondrion pcf sequence (Nivison and Hanson, Plant Cell. 1989 November; 1(11):1121-30.); the ORF79 from BORO-II RICE (Wang et al., 2006; Plant Cell. 2006 March; 18(3): 676-87. Epub 2006 Feb. 17.), the orf107 sequence of sorghum (Tang et al., *Plant J.* 1996 July; 10(1):123-33); the T-urf13 sequence of maize (Dewey et al., EMBO J. 1987 June; 6(6):1541-1546.)

The LFS and RFS may be selected from any nucleotide sequences that may be used for homologous recombination in the mitochondrion. Suitable examples include coding sequences such as the sequence coding for ATP6, ATP9, NAD1, NAD3, from tobacco, *Arabidopsis*, and rice, (Sugiyama et al., Mol Gen Genomics (2005) 272: 603-615; Unseld et al., (1997) Nat. Genet. 15 (1), 57-61; Notsu et al., Mol. Genet. Genomics 268 (4), 434-445 (2002), ATP1, ATP9 from wheat (Ogihara et al., 2005, Nucleic Acids Res., 33(19): 6235-6250), ATP6, ATP9 from *Brassica napus* (rapeseed) (Handa, 2003, Nucleic Acids Res. 31 (20), 5907-5916) and non-coding intergenic regions from tobacco, *Arabidopsis*, rice mitochondria (Sugiyama et al., Mol Gen Genomics (2005) 272: 603-615; Unseld et al., (1997) Nat. Genet. 15 (1), 57-61; Notsu et al., Mol. Genet. Genomics 268 (4), 434-445 (2002).

The mPRO and mTer may be selected from any mitochondrial promoter nucleotide sequences and any mitochondrial terminator nucleotide sequences known in the art. Suitable examples include the ATP6, ATP9, Cob, rrn18, Rps13, Rps19, Cox3, Nad6, Nad9 5' untranslated sequences (promoter region) of tobacco mitochondria (Sugiyama et al., 2004, Mol Gen Genomics (2005) 272: 603-615) and *Arabidopsis* mitochondria (Unseld et al., (1997) Nat. Genet. 15 (1), 57-61) and the ATP6, ATP9, Nad6, Nad9 3' untranslated sequence (terminator region) of tobacco mitochondia (Sugiyama et al., 2004, Mol Gen Genomics (2005) 272: 603-615) and *Arabidopsis* mitochondria (Unseld et al., (1997) Nat. Genet. 15 (1), 57-61)

The plant mitochondrion transgene cassette also comprises a primer binding domain (PBD) that once inside the mitochondrion is able to capture tRNAs as primers to form template RNA to initiate reverse transcription of introduced plant mitochondrion transformation units of the invention. A suitable tRNA for use in the present invention as a primer is tRNA-fMet which forms a template RNA ready for reverse transcription. The skilled person in the art will appreciate that PBDs are found naturally on retroelements including retroviruses and retrotransposons. PBDs comprise specific RNA domains that anneal to specific sequences on tRNA molecules. The tRNA itself does not serve as a PBD but as a primer for reverse transcription, the template for reverse transcription is the RNA molecule that carries a PBD. Novel PBDs can be readily engineered that can anneal to other tRNAs, for example any of the known 23 mitochondrial tRNAs. The tRNA itself is not the template but is used as a primer that binds to PBD on the MTU RNA template (FIG. 1).

PBDs can be designed to bind other types of tRNAs such as, tRNA-lys and tRNA-Met of tobacco mitochondria (and identified tRNAs of tobacco (23) Genbank, NC 006581), *Arabidopsis* mitochondria, and rice mitochondria (Notsu et al., Mol. Genet. Genomics 268 (4), 434-445 (2002).

Certain elements of retroelements such as retroviruses or retrotransposons, have native PBDs possessing conserved domains that anneal with complementary domains from tRNA (usually tRNA-met, or tRNA-trp); because of the conserved structures of all tRNAs (the so-called clover-leaf structure), PBDs can be engineered so that they carry specific domains that will anneal with a tRNA of choice.

A "plant mitochondrion translocation sequence" (MTS) is an RNA sequence that is capable of being bound to a plant MTS binding protein and thereby, the MTS and other RNA sequences that may be associated with it or fused with it can be transported across and into the mitochondrion. The MTS can be selected from naked RNA viruses, including the mitoviruses of the Narnaviridae, such as from Cryphonectria mitovirus 1 (CMV1),
Ophiostoma mitovirus 3a (OMV3a), Sclerotinia homoeocarpa mitovirus, Ophiostoma mitovirus 4 (OMV4), Ophiostoma mitovirus 5 (OMV5),
Ophiostoma mitovirus 6 (OMV6), *Botrytis cinerea* debilitation-related virus, Cryphonectria cubensis mitovirus 1a, Cryphonectria cubensis mitovirus 1b, Cryphonectria cubensis mitovirus 1c, Cryphonectria cubensis mitovirus 2a, Cryphonectria cubensis mitovirus 2b, Cryphonectria cubensis mitovirus 2c, Gremmeniella mitovirus S1 (GMVS1), Gremmeniella mitovirus S2, Helicobasidium mompa mitovirus 1-18, Ophiostoma mitovirus 1a (OMV1a),
Ophiostoma mitovirus 1b (OMV1b), Ophiostoma mitovirus 2 (OMV2), Ophiostoma mitovirus 3b (OMV3b), Thielaviopsis basicola mitovirus, Cryphonectria mitovirus I, viral RNAs such as those from positive stranded RNA viruses such as potato virus X (PVX), tobacco mosaic virus (TMV), tomato mosaic virus (ToMV), and viral RNAs from negative stranded RNA viruses, such as tomato spotted wilt virus (TSWV) and *Impatiens* necrotic spotted virus (INSV), viroids such as potato spindle tuber viroid PSTVd), satellite viruses such as satellite tobacco mosaic virus (STMV) and the like. Other sources of the MTS include group I and group II intron RNAs or modified versions thereof in which cryptic splicing sites have been eliminated that may be derived from a bacterium, a fungus or a mitochondrion from a plant, such as an LTRB intron lacking the sequence coding for LTRA (the protein encoded by an LTRA sequence being capable of serving as an MTS-binding protein in the methods of the invention).

Preferably, the intron is a group II intron, such as the *Lactococcus lactis* Ll.ltrB intron or a modified version of it in which cryptic splicing sites have been eliminated as outlined herein. Group II introns are widely represented in the organelles of plants and fungi, and in bacteria. Group II introns useful in the method of the invention are mobile, highly structural retroelements that encode multifunctional protein (intron encoded protein or IEP) which possesses reverse transcriptase (RT) activity. The IEP facilitates splicing of intron RNA by stabilization of the catalytically active RNA structure, performs reverse transcription and insertion of the intron into specific DNA target sites of the bacterial genome at high frequency (Moran et al. (1995) Mol Cell Biol 15:2828-2838; Cousineau et al. (1998) Cell 94:451-462).

Group II introns of bacterial origin, such as those derived from *Lactococcus* that comprise a modified LtrA gene, are preferably used in the method of the invention. The LtrA polynucleotide sequence of a *Lactococcus* bacterium, such as *Lactococcus lactis* may be modified for optimum expression in plants by inserting into it at least one polynucleotide sequence comprising one or more introns from at least one plant nucleic acid sequence, such as from one or more plant genes and by substituting certain selected codons having a low frequency of usage in native plants with codons that occur with a higher frequency in such plants. Typically, the bacterial LtrA sequence of interest is analysed with reference to plant codon usage using in silico comparisons such as those found at the website www.kazusa.or.jp/codon for bacterial codons that occur with low frequency in plants. Such codons may then be substituted with codons that have a high frequency of occurrence in plants, and an in silico-derived modified polynucleotide sequence is generated. From this optimised LtrA sequence a synthetic LtrA polynucleotide sequence corresponding to the in silico generated sequence is made using standard polynucleotide synthesis procedures known in the art, and may then be used in the preparation of constructs of use in the present invention as outlined herein. It is thought that by using a modified sequence that comprises plant codon substitutions as outlined above more plant cell environment stable polynucleotide RNA sequences are generated.

Other types of introns that may be used in the method of the invention include, for example, the group I intron from Tetrahymena (GenBank Acc. No.: X54512; Kruger K et al. (1982) Cell 31:147-157; Roman J and Woodson S A (1998) Proc Natl Acad Sci USA 95:2134-2139), the group II rIl intron from Scenedesmus obliquus (GenBank Acc. No.: X17375.2 nucleotides 28831 to 29438; Hollander V and Kuck U (1999) Nucl Acids Res 27: 2339-2344; Herdenberger F et al. (1994) Nucl Acids Res 22: 2869-2875; Kuck V et al. (1990) Nucl Acids Res 18:2691-2697), and the L1.LtrB intron (GenBank Acc. No.: U50902 nucleotides 2854 to 5345).

Aside from heterologous introns described herein, endogenous introns that occur naturally in the mitochondria, such as group II introns from plant mitochondria, for example the NAD4 intron 1 from *Arabidopsis* (Unseld et al., (1997) Nat. Genet. 15 (1), 57-61), the NAD4 intron 1 from tobacco_ (Sugiyama et al., Mol Gen Genomics (2005) 272: 603-615) or from maize Clifton et al., Plant Physiol. 136 (3), 3486-3503 (2004)), or from wheat (Ogigara et al., Nucleic Acids Res. 33 (19), 6235-6250 (2005)) or the Cox II intron and NADII intron 2 from wheat (Nucleic Acids Res. 33 (19), 6235-6250 (2005). Introns which occur naturally in the mitochondria of the plant of interest may be modified such that they have a sequence homology of about 50%, 60%, 70%, 75%, 80%, 85%, 90% or 95%, or of any percentage sequence homology therebetween, with the sequence of the starting intron, while retaining functionality, may also be employed in the method of the invention. Other MTS include RNA domains found on tobacco TNT1, yeast Ty1- and Ty3-like retrotransposons or other RNA that harbours a domain that is recognised by an RNA binding protein that is driven into the mitochondria.

A "mitochondrion translocation sequence binding protein" (MTS-BP) can be any RNA binding protein that recognises and binds to specific RNA domains of interest and is fused to a mitochondrial transit peptide. Examples of suitable MTS-BP proteins may be selected from the Ltra protein from the group II intron II Ltrb, coat proteins that bind to RNA viruses such as the coat protein from potato virus X (PVX), the coat protein of TMV, RNA-dependent RNA polymerases (RdRpS) of RNA viruses such as the replicases of PVX or TMV, reverse transcriptase protein from retrotransposons, such as tobacco TnT1, yeast Ty1-1 which recognise structures on the retrotransposon RNA molecule, and proteins that bind to cellular RNAs such as translation elongation factor proteins and ribosomal binding proteins. Preferably, MTS-BP protein is the LrtA protein from the group II intron 11Ltrb.

A "plant mitochondrion transit peptide" (TP) is one that may be derived or obtained from a mitochondrion-targeted protein, for example those described by Boutry et al Nature 328340-342 (1987), the signal peptide from the tobacco F1-ATPase β subunit and the *Arabidopsis* CPN60 protein and those that may be predicted by Mitochondrial localisation programmes such as "Predotar" and SignalP(Predotar: a neural network-based prediction service for identifying putative mitochondrial and ER targeting sequences urgi.versailles.inra.fr/predotar/predotar.html; SIGNALP (www.cbs.dtu.dk/services/SignalP).

The "mitochondrion reverse transcriptase" protein, if employed, may be selected from a retrovirus source, such as from plant retroviruses such as SIRE-1 from soybean, or from a retrotransposon source such as from the yeast Ty11 retrotransposon, for example the reverse transcriptase-RNaseH domain (Goffeau et al., Science 274 (5287), 546-547 (1996)) or the tobacco TnT1 retrotrasnposon (RTRH domain) (Vernhettes et., al.; Mol. Biol. Evol. 15 (7), 827-836 (1998)).

A plant nuclear promoter (for example, an exogenous nucleus specific promoter) is one that is able to drive expression of a nucleic acid sequence such as a cDNA sequence or a full length gene sequence in the nucleus of a plant cell, forming a transcribed RNA sequence. The plant nuclear promoter is one that is introduced in front of a nucleic acid sequence of interest and is operably associated therewith. Thus a plant nuclear promoter is one that has been placed in front of a selected polynucleotide component. Typically, a plant nuclear promoter, such as an exogenous nucleus specific promoter, is one that is transferred to a host cell or host plant from a source other than the host cell or host plant.

The cDNAs encoding a polynucleotide of the invention contain at least one type of nucleus specific promoter that is operable in a plant cell, for example, an inducible or a constitutive promoter operatively linked to a first and/or second nucleic acid sequence or nucleic acid sequence component as herein defined and as provided by the present invention. As discussed, this enables control of expression of polynucleotides of the invention. The invention also provides plants transformed with polynucleotide sequences or constructs and methods including introduction of such polynucleotide nucleic acid sequences or constructs into a plant cell and/or induction of expression of said first or second nucleic acid sequence or construct within a plant cell, e.g. by application of a suitable stimulus, such as an effective exogenous inducer.

The term "inducible" as applied to a promoter is well understood by those skilled in the art. In essence, expression under the control of an inducible promoter is "switched on" or increased in response to an applied stimulus (which may be generated within a cell or provided exogenously). The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus. The preferable situation is where the level of expression increases upon application of the relevant stimulus by an amount effective to alter a phenotypic characteristic. Thus an inducible (or "switchable") promoter may be used which causes a basic level of expression in the absence of the stimulus which level is too low to bring about a desired phenotype (and may in fact be zero). Upon application of the stimulus, expression is increased (or switched on) to a level, which brings about the desired phenotype. One example of an inducible promoter is the ethanol inducible gene switch disclosed in Caddick et al (1998) Nature Biotechnology 16: 177-180. A number of inducible promoters are known in the art.

Chemically regulated promoters can be used to modulate the expression of a gene or a polynucleotide sequence of the invention in a plant through the application of an exogenous chemical regulator. Depending upon the objective, the promoter may be a chemically inducible promoter, where application of the chemical induces gene expression, or a chemical-repressible promoter, where application of the chemical represses gene expression. Chemically inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemically regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Where enhanced expression in particular tissues is desired, tissue-specific promoters can be utilized. Tissue-specific promoters include those described by Yamamoto et al. (1997) *Plant J.* 12(2)255-265; Kawamata et al. (1997) *Plant Cell Physiol.* 38(7):792-803; Hansen et al. (1997) *Mol. Gen. Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et-al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol. Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505.

So-called constitutive promoters may also be used in the methods of the present invention. Constitutive promoters include, for example, CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. application Ser. No. 08/409,297), and the like. Other constitutive promoters include those in U.S. Pat. Nos. 5,608,149; 5,608,144; 5,604,121; 5,569,597; 5,466,785; 5,399,680; 5,268,463; and 5,608,142. In a preferment, the plant nuclear promoter used in the method of the invention is a constitutive promoter.

The expression in the mitochondrion is effected by employing a plant mitochondrion promoter such as mitochondrion specific promoters and/or transcription regulation elements. Examples include the ATP6 promoter from tobacco or *Arabidopsis* mitochondria, the ATP9 promoter from *Arabidopsis* or tobacco mitochondria or the mitochondrion specific promoter may have a polycistronic "operon" assigned to it, such as the Orf125-NAD3-RSP12 region from tobacco (Sugiyama et al., Mol Gen Genomics (2005) 272: 603-615) or the NAD3-RPS12-Orf299-orf156 region from wheat mitochondria (Clifton et al., Plant Physiol. 136 (3), 3486-3503 (2004).

In another aspect of the invention there is provided a mitochondrion transformation sequence that comprises:
i) a plant mitochondrion translocation sequence;
ii) a mitochondrion transgene cassette; and
iii) a primer binding domain.

The plant mitochondrion translocation sequence and the primer binding domain are as defined herein.

The mitochondrion transgene cassette comprises a left flanking sequence (LFS) and a right flanking sequence (RFS) as herein described, and may include a promoter region and/or a terminator region sourced from a higher or lower plant mitochondrion, for example from tobacco, *arabidopsis, brassica* sp., potato, corn (maize), canola, rice, wheat, barley, *brassica* sp., cotton, algae (e.g. blue green species), lemnospora ("duckweed"), or moss (e.g. *physcomitrella patens*). Preferably, the mPRO and mTER regions are sourced from higher plant species. Where the LFS and RFS do not include a promoter and/or a terminator region, these components may be placed adjacent to the LFS and/or RFS, as appropriate, or there may be a spacer region therein between. Included within the mitochondrion transgene cassette is at least one transgene or one nucleotide sequence of choice that is destined to be transcribed and/or translated in the mitochondrion in accordance with the design of the method of the present invention for example, for the production of desired protein(s), RNAs of interest, or knockout of endogenous mitochondrial genes and regulatory sequences. Suitable transgenes of interest contemplated for protein or peptide production in a method of the present invention include plant proteins and pharmaceutical proteins for use in mammals, including man, such as insulin, pre-proinsulin, proinsulin, glucagon, interferons such as α-interferon, β-interferon, γ-interferon, blood-clotting factors selected from Factor VII, VIII, IX, X, XI, and XII, fertility hormones including luteinising hormone, follicle stimulating hormone growth factors including epidermal growth factor, platelet-derived growth factor, granulocyte colony stimulating factor and the like, prolactin, oxytocin, thyroid stimulating hormone, adrenocorticotropic hormone, calcitonin, parathyroid hormone, somatostatin, erythropoietin (EPO), enzymes such as β-glucocerebrosidase, haemoglobin, serum albumin, collagen, insect toxic protein from *Bacillus thuringiensis*; herbicide resistance protein (glyphosate); salt-tolerance proteins; proteins involved in conferring cytoplasmic male sterility to plant breeding lines; nutritional enhancement proteins involved in the biosynthesis of phenolics, starches, sugars, alkaloids, vitamins, and edible vaccines, and the like. Furthermore, the method of the invention can be used for the production of specific monoclonal antibodies, or active fragments thereof and of industrial enzymes.

All proteins mentioned hereinabove are of the plant and human type. Other proteins that are contemplated for production in the present invention include proteins for use in veterinary care and may correspond to animal homologues of human proteins, such as the human proteins mentioned hereinabove.

In a further aspect of the invention there is provided a plant cell that comprises mitochondria that are permanently transformed with an exogenous or a heterologous nucleic acid sequence that encodes for a protein of interest. Suitable proteins and peptides of interest may be selected from those provided herein. Certain heterologous nucleic acids of interest are useful in conferring cytoplasmic male sterility to plant breeding lines such as the petunia mitochondrion pcf sequence (Nivison and Hanson, Plant Cell. 1989 November; 1(11):1121-30.); the ORF79 from BORO-II RICE (Wang et al., 2006; Plant Cell. 2006 March; 18(3):676-87. Epub 2006 Feb. 17.), the orf107 sequence of sorghum (Tang et al., Plant J. 1996 July; 10(1):123-33); the T-urf13 sequence of maize (Dewey et al., EMBO J. 1987 June; 6(6):1541-1546) and as a consequence plant breeding lines breeding true for male sterility may be achieved in far fewer generations of crosses, for example in one generation or two generations. The invention provides for the first time, a reliable means by which to confer permanent cytoplasmic male sterility in male plant breeding lines without the need for engaging in multiple crossings over generations of plants, thus speeding up breeding processes where male sterile lines are desired, for example in *brassica* species such as in cauliflower, broccoli (e.g. green and purple sprouting), cabbage (e.g. red, green and white cabbages), curly kale, Brussels sprouts, tomato, *capsicum*, squashes, canola (rape), sunflower, soyabean, corn (maize), rice, wheat, barley and the like. In a preferment of this aspect of the invention, there is provided a plant cell comprising mitochondria that are permanently transformed with an exogenous or a heterologous nucleic acid sequence that encodes for a protein that is capable of conferring cytoplasmic male sterility to a plant derived from the said plant cell. Accordingly, there is also provided a plant derived from a plant cell as described herein.

Naturally, the person skilled in the art will appreciate that where nuclear terminator DNA sequences will be present in constructs used in the invention, these are contemplated as comprising a DNA sequence at the end of a transcriptional unit which signals termination of transcription. These elements are 3'-non-translated sequences containing polyadenylation signals, which act to cause the addition of polyadenylate sequences to the 3' end of primary transcripts. For expression in plant cells the nopaline synthase transcriptional terminator (A. Depicker et al., 1982, J. of Mol. & Applied Gen. 1:561-573) sequence serves as a transcriptional termination signal.

Those skilled in the art are well able to construct vectors and design protocols for recombinant nucleic acid sequences or gene expression. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology*, Second Edition, Ausubel et al. eds., John Wiley & Sons, 1992. The disclosures of Sambrook et al. and Ausubel et al. are incorporated herein by reference. Specific procedures and vectors previously used with wide success upon plants are described by Bevan (Nucl. Acids Res. 12, 8711-8721 (1984)) and Guerineau and Mullineaux (1993) (Plant transformation and expression vectors. In: Plant Molecular Biology Labfax (Croy RRD ed.) Oxford, BIOS Scientific Publishers, pp 121-148).

Naturally, the skilled addressee will appreciate that each introduced transgene in a transgene cassette will be under regulatory control of its own exogenous mitochondrial promoter and mitochondrial terminator. When two or more target proteins are destined to be produced from a single carrier RNA it is preferable if they are able to be readily separated, for example by binding to different protein-specific antibodies (monoclonal or polyclonal) in the harvesting phase of the plant cell culture system.

Selectable genetic markers may facilitate the selection of transgenic plants and these may consist of chimaeric genes that confer selectable phenotypes such as resistance to antibiotics such as spectinomycin, streptomycin, kanamycin, neomycin, hygromycin, puramycin, phosphinotricin, chlorsulfuron, methotrexate, gentamycin, spectinomycin, imidazolinones and glyphosate.

When introducing selected nucleic acid sequences according to the present invention into a cell, certain considerations must be taken into account, well known to those skilled in the art. The nucleic acid to be inserted should be assembled within a construct, which contains effective regulatory elements, which will drive transcription. There must be available a method of transporting the construct into the cell. Once the construct is within the cell, integration into the endogenous chromosomal material either will or will not occur. Finally, as far as plants are concerned the target cell type must be such that cells can be regenerated into whole plants.

Plants transformed with DNA segments containing sequences of interest as provided herein may be produced by standard techniques, which are already known for the genetic manipulation of plants. DNA can be transformed into plant cells using any suitable technology, such as a disarmed Ti-plasmid vector carried by *Agrobacterium* exploiting its natural gene transfer ability (EP-A-270355, EP-A-0116718, NAR 12(22) 8711-87215 1984), particle or micro projectile bombardment (U.S. Pat. No. 5,100,792, EP-A-444882, EP-A-434616) microinjection (WO 92/09696, WO 94/00583, EP 331083, EP 175966, Green et al. (1987) *Plant Tissue and Cell Culture*, Academic Press), electroporation (EP 290395, WO 8706614) other forms of direct DNA uptake (DE 4005152, WO 9012096, U.S. Pat. No. 4,684,611), liposome mediated DNA uptake (e.g. Freeman et al. *Plant Cell Physiol.* 29: 1353 (1984)), or the vortexing method (e.g. Kindle, *PNAS U.S.A.* 87: 1228 (1990d) Physical methods for the transformation of plant cells are reviewed in Oard, 1991, *Biotech. Adv.* 9: 1-11.

Thus once a nucleic acid sequence or gene has been identified, it may be reintroduced into plant cells using techniques well known to those skilled in the art to produce transgenic plants of the appropriate phenotype.

*Agrobacterium* transformation is widely used by those skilled in the art to transform dicotyledonous species. Production of stable, fertile transgenic plants in almost all economically relevant monocot plants is also now routine: (Toriyama, et al. (1988) *Bio/Technology* 6, 1072-1074; Zhang, et al. (1988) *Plant Cell Rep.* 7, 379-384; Zhang, et al. (1988) *Theor. Appl. Genet.* 76, 835-840; Shimamoto, et al. (1989) *Nature* 338, 274-276; Datta, et al. (1990) *Bio/Technology* 8, 736-740; Christou, et al. (1991) *Bio/Technology* 9, 957-962; Peng, et al. (1991) International Rice Research Institute, Manila, Philippines 563-574; Cao, et al. (1992) *Plant Cell Rep.* 11, 585-591; Li, et al. (1993) *Plant Cell Rep.* 12, 250-255; Rathore, et al. (1993) *Plant Molecular Biology* 21, 871-884; Fromm, et al. (1990) *Bio/Technology* 8, 833-839; Gordon-Kamm, et al. (1990) *Plant Cell* 2, 603-618; D'Halluin, et al. (1992) *Plant Cell* 4, 1495-1505; Walters, et al. (1992) *Plant Molecular Biology* 18, 189-200; Koziel, et al. (1993) *Biotechnology* 11, 194-200; Vasil, I. K. (1994) *Plant Molecular Biology* 25, 925-937; Weeks, et al. (1993) *Plant Physiology* 102, 1077-1084; Somers, et al. (1992) *Bio/Technology* 10, 1589-1594; WO92/14828). In particular, *Agrobacterium* mediated transformation is now a highly efficient alternative transformation method in monocots (Hiei et al. (1994) *The Plant Journal* 6, 271-282).

The generation of fertile transgenic plants has been achieved in the cereals rice, maize, wheat, oat, and barley (reviewed in Shimamoto, K. (1994) *Current Opinion in Biotechnology* 5, 158-162.; Vasil, et al. (1992) *Bio/Technology* 10, 667-674; Vain et al., 1995, *Biotechnology Advances* 13 (4): 653-671; Vasil, 1996, *Nature Biotechnology* 14 page 702). Wan and Lemaux (1994) *Plant Physiol.* 104: 37-48 describe techniques for generation of large numbers of independently transformed fertile barley plants.

Micro projectile bombardment, electroporation and direct DNA uptake are preferred where *Agrobacterium* is inefficient or ineffective. Alternatively, a combination of different techniques may be employed to enhance the efficiency of the transformation process, e.g. bombardment with *Agrobacterium* coated micro particles (EP-A-486234) or micro projectile bombardment to induce wounding followed by co-cultivation with *Agrobacterium* (EP-A-486233).

Following transformation, a plant may be regenerated, e.g. from single cells, callus tissue or leaf discs, as is standard in the art. Almost any plant can be entirely regenerated from cells, tissues and organs of the plant. Available techniques are reviewed in Vasil et al., *Cell Culture and*

*Somatic Cell Genetics of Plants, Vol. I, II and III, Laboratory Procedures and Their Applications*, Academic Press, 1984, and Weiss Bach and Weiss Bach, *Methods for Plant Molecular Biology*, Academic Press, 1989.

The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention, nor is the choice of technique for plant regeneration.

The invention further encompasses a host cell transformed with vectors or constructs as set forth above, especially a plant or a microbial cell. Thus, a host cell, such as a plant cell, including nucleotide sequences of the invention as herein indicated is provided. Within the cell, the nucleotide sequence may be incorporated within the chromosome.

Also according to the invention there is provided a plant cell having incorporated into its genome at least a nucleotide sequence, particularly heterologous nucleotide sequences, as provided by the present invention under operative control of regulatory sequences for control of expression as herein described. The coding sequence may be operably linked to one or more regulatory sequences which may be heterologous or foreign to the nucleic acid sequences employed in the invention, such as those not naturally associated with the nucleic acid sequence(s) for its (their) expression. The nucleotide sequence according to the invention may be placed under the control of an externally inducible promoter to place expression under the control of the user. A further aspect of the present invention provides a method of making such a plant cell involving introduction of nucleic acid sequence(s) contemplated for use in the invention or a suitable vector including the sequence(s) contemplated for use in the invention into a plant cell and causing or allowing recombination between the vector and the plant cell genome to introduce the said sequences into the genome. The invention extends to plant cells containing a nucleotide sequence according to the invention as a result of introduction of the nucleotide sequence into an ancestor cell.

The term "heterologous" may be used to indicate that the gene/sequence of nucleotides in question have been introduced into said cells of the plant or an ancestor thereof, using genetic engineering, i.e. by human intervention. A transgenic plant cell, i.e. transgenic for the nucleotide sequence in question, may be provided. The transgene may be on an extra-genomic vector or incorporated, preferably stably, into the genome. A heterologous gene may replace an endogenous equivalent gene, i.e. one that normally performs the same or a similar function, or the inserted sequence may be additional to the endogenous gene or other sequence. An advantage of introduction of a heterologous gene is the ability to place expression of a sequence under the control of a promoter of choice, in order to be able to influence expression according to preference. Furthermore, mutants, variants and derivatives of the wild-type gene, e.g. with higher activity than wild type, may be used in place of the endogenous gene. Nucleotide sequences heterologous, or exogenous or foreign, to a plant cell may be non-naturally occurring in cells of that type, variety or species. Thus, a nucleotide sequence may include a coding sequence of or derived from a particular type of plant cell or species or variety of plant, placed within the context of a plant cell of a different type or species or variety of plant. A further possibility is for a nucleotide sequence to be placed within a cell in which it or a homologue is found naturally, but wherein the nucleotide sequence is linked and/or adjacent to nucleic acid which does not occur naturally within the cell, or cells of that type or species or variety of plant, such as operably linked to one or more regulatory sequences, such as a promoter sequence, for control of expression. A sequence within a plant or other host cell may be identifiably heterologous, exogenous or foreign.

Plants which include a plant cell according to the invention are also provided, along with any part or propagule thereof, seed, selfed or hybrid progeny and descendants. Particularly provided are transgenic crop plants, which have been engineered to carry genes identified as stated above. Examples of suitable plants include tobacco (*Nicotiana tabacum*) and other *Nicotiana* species, carrot, vegetable and oilseed Brassicas, melons, Capsicums, grape vines, lettuce, strawberry, sugar beet, wheat, barley, corn (maize), rice, soybean, peas, sorghum, sunflower, tomato, cotton, and potato. Especially preferred transgenic plants of the invention include cotton, rice, oilseed *Brassica* species such as canola, corn (maize) and soybean.

In addition to a plant, the present invention provides any clone of such a plant, seed, selfed or hybrid progeny and descendants, and any part of any of these, such as cuttings, seed. The invention provides any plant propagule that is any part which may be used in reproduction or propagation, sexual or asexual, including cuttings, seed and so on. Also encompassed by the invention is a plant which is a sexually or asexually propagated offspring, clone or descendant of such a plant, or any part or propagule of said plant, offspring, clone or descendant.

The present invention also encompasses the polypeptide expression product of a nucleic acid molecule according to the invention as disclosed herein or obtainable in accordance with the information and suggestions herein. Also provided are methods of making such an expression product by expression from a nucleotide sequence encoding therefore under suitable conditions in suitable host cells e.g. *E. coli*. Those skilled in the art are well able to construct vectors and design protocols and systems for expression and recovery of products of recombinant gene expression.

The heterologous or exogenous target protein is contemplated to be any protein of interest that may be produced by the method of the invention.

A polypeptide according to the present invention may be an allele, variant, fragment, derivative, mutant or homologue of the (a) polypeptides as mentioned herein. The allele, variant, fragment, derivative, mutant or homologue may have substantially the same function of the polypeptides alluded to above and as shown herein or may be a functional mutant thereof.

"Homology" in relation to an amino acid sequence or polypeptide sequence produced by the method of the invention may be used to refer to identity or similarity, preferably identity. As noted already above, high level of amino acid identity may be limited to functionally significant domains or regions.

In certain embodiments, an allele, variant, derivative, mutant derivative, mutant or homologue of the specific sequence may show little overall homology, say about 20%, or about 25%, or about 30%, or about 35%, or about 40% or about 45%, with the specific sequence. However, in functionally significant domains or regions, the amino acid homology may be much higher. Putative functionally significant domains or regions can be identified using processes of bioinformatics, including comparison of the sequences of homologues.

Functionally significant domains or regions of different polypeptides may be combined for expression from encoding nucleic acid as a fusion protein. For example, particularly advantageous or desirable properties of different homologues may be combined in a hybrid protein, such that the resultant expression product, may include fragments of various parent proteins, if appropriate.

Similarity of amino acid sequences may be as defined and determined by the TBLASTN program, of Altschul et al. (1990) *J. Mol. Biol.* 215: 403-10, which is in standard use in the art. In particular, TBLASTN 2.0 may be used with Matrix BLOSUM62 and GAP penalties: existence: 11, extension: 1. Another standard program that may be used is BestFit, which is part of the Wisconsin Package, Version 8, September 1994, (Genetics Computer Group, 575 Science Drive, Madison, Wis., USA, Wisconsin 53711). BestFit makes an optimal alignment of the best segment of similarity between two sequences. Optimal alignments are found by inserting gaps to maximize the number of matches using the local homology algorithm of Smith and Waterman (*Adv. Appl. Math.* (1981) 2: 482-489). Other algorithms include GAP, which uses the Needleman and Wunsch algorithm to align two complete sequences that maximizes the number of matches and minimizes the number of gaps. As with any algorithm, generally the default parameters are used, which for GAP are a gap creation penalty=12 and gap extension penalty=4. Alternatively, a gap creation penalty of 3 and gap extension penalty of 0.1 may be used. The algorithm FASTA (which uses the method of Pearson and Lipman (1988) *PNAS USA* 85: 2444-2448) is a further alternative.

Use of either of the terms "homology" and "homologous" herein does not imply any necessary evolutionary relationship between compared sequences, in keeping for example with standard use of terms such as "homologous recombination" which merely requires that two nucleotide sequences are sufficiently similar to recombine under the appropriate conditions. Further discussion of polypeptides according to the present invention, which may be encoded by nucleic acid according to the present invention, is found below.

The teaching of all references cited herein is incorporated in its entirety into the present description.

There now follow non-limiting examples and figures illustrating the invention.

FIG. 1: Major components of the plant mitochondria transformation system.

(1) Mitochondria transformation unit (MTU) (i) a plant mitochondrion translocation sequence (MTS); (ii) a mitochondrion transgene cassette comprising: a left flanking sequence (LFS)[1] and right flanking sequence (RFS)[1] to facilitate insertion of the cassette into the mitochondria genome using homologous recombination, a promoter region from tobacco mitochondria (mPro)[1], a sequence (transgene) of interest (TG), a transcription terminator from the tobacco mitochondrial genome (mTER)[1]; and (iii) a primer binding domain (PBD). (2) Reverse Transcriptase-RNase H gene translationally fused to the mitochondria transit peptide from tobacco F1-ATPAse beta subunit (mTP). (3) MTS-Binding peptide translationally fused to the mitochondria transit peptide from Tobacco F1-ATPAse beta subunit (mTP).[1] mPRO and mTER can be part of LFS and RFS respectively, if for example the transgene is fused to a native mitochondrial gene.

Figure 2:
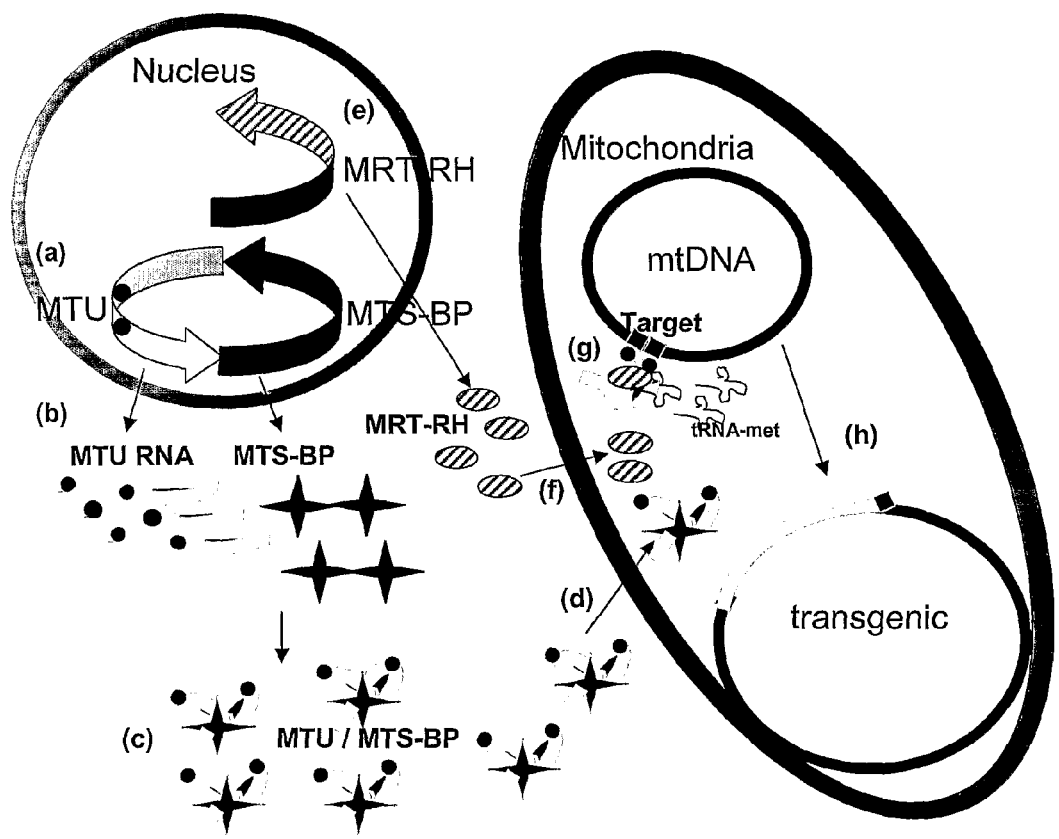

FIG. 2: Schematic representation of the mitochondria transformation system (1) Targeting of RNA-protein complexes to the plant mitochondria.

(a) After transformation of the mitochondria transformation unit (MTU) construct into the plant genome a strong expression of the MTU RNA which contains the mitochondria targeting cassette and mitochondria translocation sequence (MTS) is achieved from a nuclear specific promoter. The MTS-binding protein (MTS-BP) is expressed from a separate cassette. (b) Both MTS-BP and MTU RNAs are transferred from the nucleus into the cytoplasm where MTS-BP is translated. and (c) binds to the MTU RNA via recognition of MTS to form the MTU/MTS-BP nucleoprotein complex. (d) As MTS-BP carries a mitochondria transit peptide it preferentially transfers the MTU/MTS-BP complex into the mitochondria. Once MTU is presented in the plant cell via nuclear transformation, the mitochondria will then be permanently bombarded by the expressed MTU/MTS-BP complex. Such stable and continuous pumping of the complex into the targeted organelle is a prerequisite for achieving a high efficiency of organelle transformation.

(2) Reverse transcription and insertion into the mitochondrial genome.

The third component of the mitochondria transformation system is the mitochondria-targeted reverse transcriptase-RNaseH protein (MRT-RH). (e) MRT-RH is expressed from a nuclear expression cassette and (f) is driven to the mitochondria by its mitochondria transit peptide. (g) Once inside the organelle, MRT-RH catalyses reverse transcription of the MTU RNA primed with tRNA-Met. (h) Insertion of the reverse transcribed cassette into the mitochondrial genome is induced due to homologous recombination between sequences flanking the mitochondria transgene cassette and the homologous sequences in the mitochondrial genome.

Figure 3:
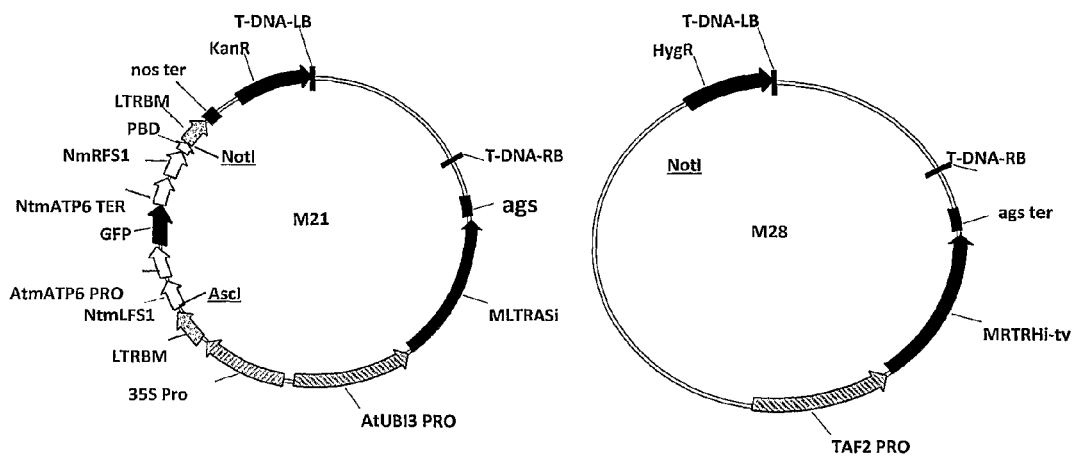

FIG. 3: M21 and M28 constructs

M21 Construct

The binary vector pGreen0029 was used as a backbone and enables selection of transgenic plants with kanamycin. It is used for co-expression of the mitochondria transformation unit with the MTS-binding protein mLTRASi in the plant cell.

The mitochondria transformation unit is made up the following components: NtmLFS1 and NtmRFS1 are homologous to two adjacent sequences in the tobacco mitochondrial mitochondria non-coding sequences (position 292641-293235 and 293262-293835, respectively), the GFP gene is placed under the control of *Arabidopsis* mitochondria ATP6 promoter AtmATP6 PRO and the tobacco ATP6 terminator NtmATP6 TER. PBD (primer-binding domain) is designed to capture the plant mitochondria tRNA-fMet to initiate reverse transcription, LTRBM is based on the LtrB intron sequence from *lactococcus lactis* and serves as the mitochondria translocation sequence (MTS) into which the first six components were cloned, between the AscI and NotI restriction sites. The whole mitochondria transformation unit was placed under the control of the 35S promoter and the nos terminator.

The second cassette is for expression of the MTS-binding protein MLTRASi placed under the control of the AtUBI3 promoter and ags terminator.

M28 Construct

The pSOUP vector (EU048870) carrying T-DNA from the pGreen0179 vector (EU048866) was used as a backbone and enables selection of transgenic plants with Hygromycin. It is used for expression of the mitochondria-targeted reverse transcriptase-RNaseH protein (mRTRHi-Ty) under the control of the TAF2 promoter and ags terminator.

Figure 4:
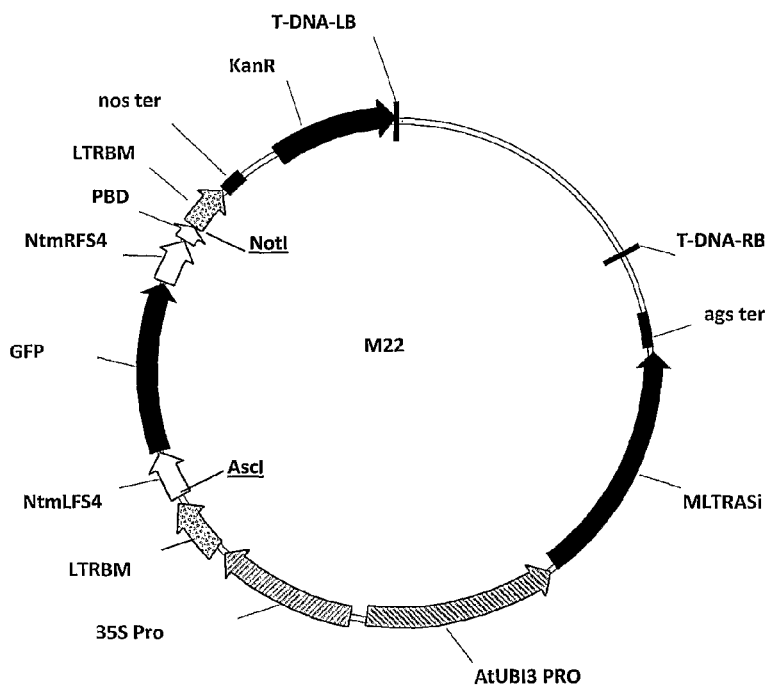

FIG. 4: M22 construct

The binary vector pGreen0029 was used as a backbone and enables selection of transgenic plants with kanamycin. It is used for co-expression of the mitochondria transformation unit with the MTS-binding protein mLTRASi in the plant cell.

The mitochondria transformation unit is made up the following components: NtmLFS4 and NtmRFS4 correspond to *Nicotiana tabacum* mitochondria sequences position 24888-24579 and 24578-24269 respectively (on the complementary strand). NtmLFS4 corresponds to the 5' end of the gene coding for ATP6 and can be used for translational fusion with any gene of interest, promoter activity is provided by the ATP6 promoter upstream of NtmLFS4 on the tobacco mitochondrial genome and termination of transcription is achieved with the ATP6 terminator sequence within NtmRFS4. The GFP gene was fused to NtmLFS4 and cloned upstream of NtmRFS4 and PBD. LTRBM is based on the LtrB intron sequence from *lactococcus lactis* and serves as the mitochondria translocation sequence (MTS) into which the first four components were cloned, between the AscI and NotI restriction sites. The whole mitochondria transformation unit was placed under the control of the 35S promoter and the nos terminator.

The second cassette is for expression of the MTS-binding protein MLTRASi placed under the control of the AtUBI3 promoter and ags terminator.

Figure 5:
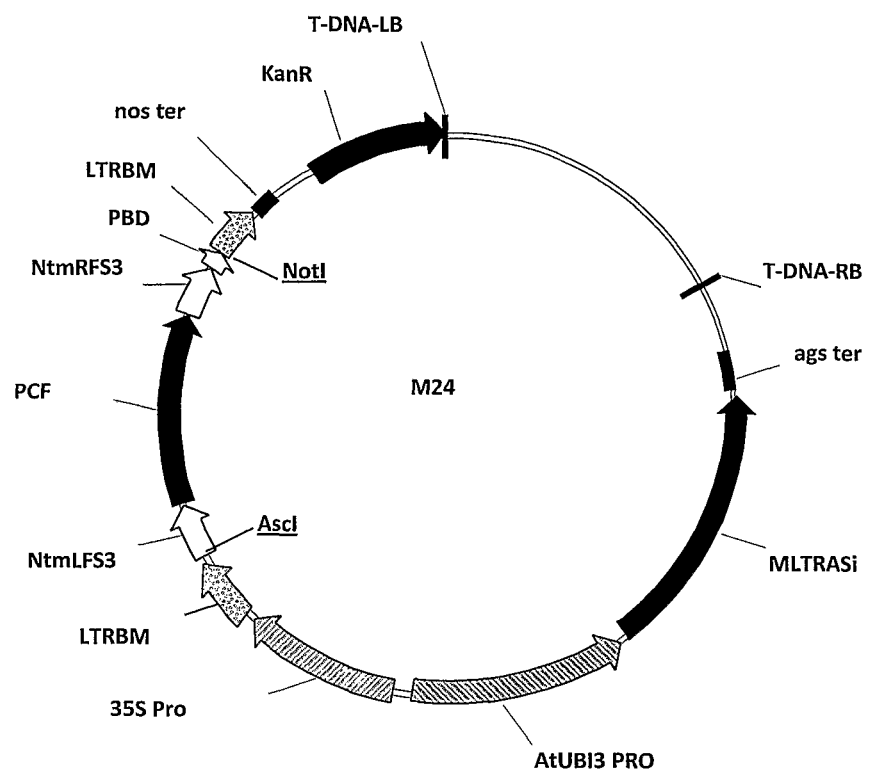

FIG. 5: M24 construct

The binary vector pGreen0029 was used as a backbone and enables selection of transgenic plants with kanamycin. It is used for co-expression of the mitochondria transformation unit with the MTS-binding protein mLTRASi in the plant cell.

The mitochondria transformation unit is made up the following components: NtmLFS3 and NtmRFS3 correspond to *Nicotiana tabacum* mitochondria sequences position 85896-86331 and 86332-86860, respectively. the PCFM gene is based on the CMS-inducing PCF gene from petunia mitochondria, PBD (primer-binding domain) is designed to capture the plant mitochondria tRNA-fMet to initiate reverse transcription. LTRBM is based on the LtrB intron sequence from *lactococcus lactis* and serves as the mitochondria translocation sequence (MTS) into which the first four components were cloned, between the AscI and NotI restriction sites. The whole mitochondria transformation unit was placed under the control of the 35S promoter and the nos terminator.

Figure 6:
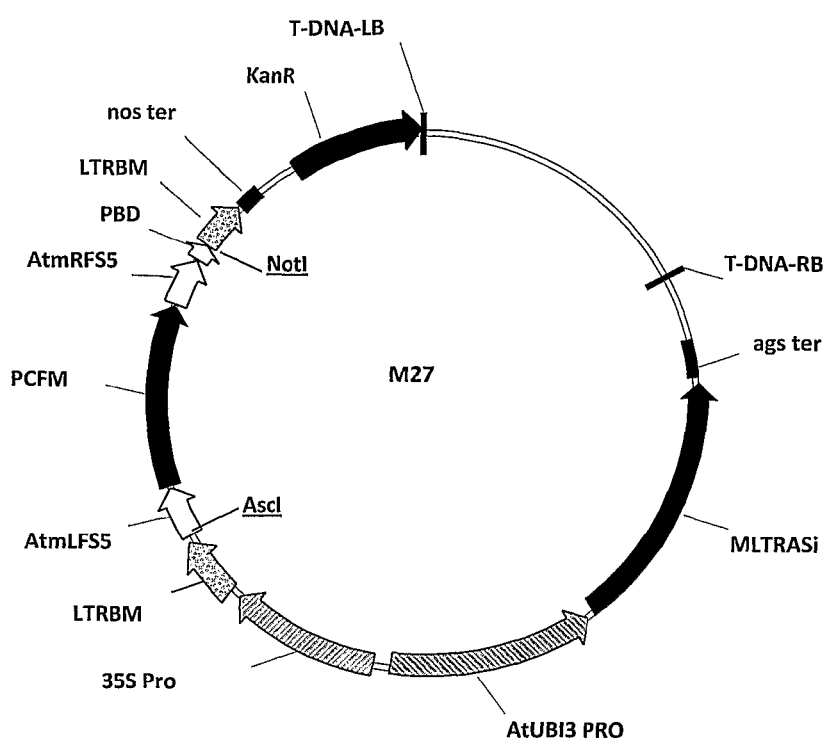

The second cassette is for expression of the MTS-binding protein MLTRASi placed under the control of the AtUBI3 promoter and ags terminator FIG. 6: M27 construct The binary vector pGreen0029 was used as a backbone and enables selection of transgenic plants with kanamycin. It is used for co-expression of the mitochondria transformation unit with the MTS-binding protein mLTRASi in the plant cell.

The mitochondria transformation unit is made up five components: AtmLFS5 and AtmRFS5 are homologous to two adjacent sequences in the *Arabidopsis* mitochondrial (position 344225-344571 and 344572-344926, respectively), the PCFM gene is based on the CMS-inducing PCF gene from petunia mitochondria, PBD (primer-binding domain) is designed to capture the plant mitochondria tRNA-fMet to initiate reverse transcription, LTRBM is based on the LtrB intron sequence from *lactococcus lactis* and serves as the mitochondria translocation sequence (MTS) into which the first four components were cloned, between the AscI and NotI restriction sites. The whole mitochondria transformation unit was placed under the control of the 35S promoter and the nos terminator.

The second cassette is for expression of the MTS-binding protein MLTRASi placed under the control of the AtUBI3 promoter and ags terminator.

M28 Construct

The pSOUP vector (EU048870) carrying T-DNA from the pGreen0179 vector (EU048866) was used as a backbone and enables selection of transgenic plants with Hygromycin. It is used for expression of the mitochondria-targeted reverse transcriptase-RNaseH protein (mRTRHi-Ty) under the control of the TAF2 promoter and ags terminator FIG. 7: Aborted pollen phenotype in tobacco plants transformed with the CMS-inducing pcf gene from petunia mitochondria (A,B) Pollen from wild type (WT) plants.

(C,D) Pollen from transgenic tobacco line PCFM1, transformed with the M24 vector carrying the CMS-inducing PCF orf from petunia, showing 90% of aborted pollen.

Figures 7, 8:
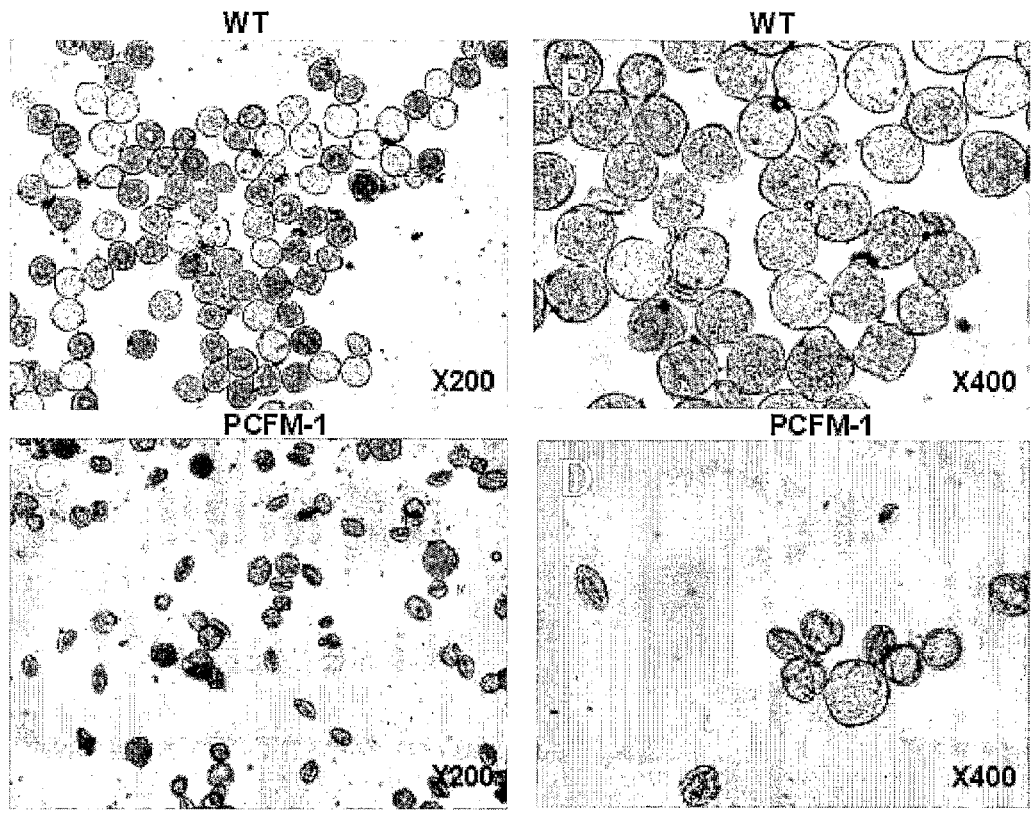

FIG. 8: Modifications of the mitochondria transformation cassette were made by designing primer binding domain and positioning of building blocks on the transgene cassette.

MTU—mitochondria transformation unit; MTS—mitochondria translocation sequence; PDB-MIT—primer binding domain designed for reverse transcription in the mitochondria using tRNA-Met from mitochondria; PBD-CYT—primer binding domain designed for reverse transcription, in the cytoplasm using cytoplasmic tRNA-Met.

The modifications detailed in Example section 1B hereinafter and corresponding figures include modifications of the use of PBD for the binding of cytoplasmic tRNA-Met as primer. As one modification MTS can be located at both the 5'- and 3'-ends of the transformation cassette, such as in the case with the LtrB intron. The transgene cassette is inserted inside of the LtrB intron (domain IV). The PDB-MIT is located downstream of the LtrB 3'-end of the cassette (MTS-3'), so that the LtrA protein is able to function as both a translocation protein and reverse transcriptase. The LtrA protein has three major functions: (1) as a maturase (it binds to LtrB RNA and stabilises the secondary structure of the RNA, and assists splicing); (2) as an endonuclease (it induces single-stranded DNA breaks on target site); and (3) as a reverse transcriptase (it performs reverse transcription of the intron RNA after insertion of the LtrB intron RNA into the donor site).

The LtrA protein is unable to perform the reverse transcription reaction efficiently if the PBD-CYT is located adjacent to and in front of a mitochondrion translocation sequence at the 3'-end of the MTU (MTS-3') as in FIG. 8(B), but can efficiently reverse transcribe RNA if the PBD is located downstream of a chloroplast translocation sequence (MTS-3') as shown in FIG. 8A. Such a positioning or the combination of components of the transformation cassette as shown in FIG. 8(A) allows both the translocation of the MTU into the mitochondrion and reverse transcription of the MTU by the LtrA protein. Thus, by positioning of the MTS components and of the PBD-MIT as shown in FIG. 8(A) the procedure of transformation is simplified since there is no requirement to co-deliver another gene to provide a reverse transcriptase function.

A similar simplification of the procedure is achieved if a PBD-CYT is used, since there is a significant amount of native endogenous reverse transcriptase in the cytoplasm, and reverse transcription is initiated by endogenous reverse transcriptase using cytoplasmic tRNA-Met. This also eliminates the necessity for the co-delivery of another gene for reverse transcription in the mitochondria.

The case in FIG. 8A and FIG. 8B is attributed to the LtrB intron.

Figure 9:
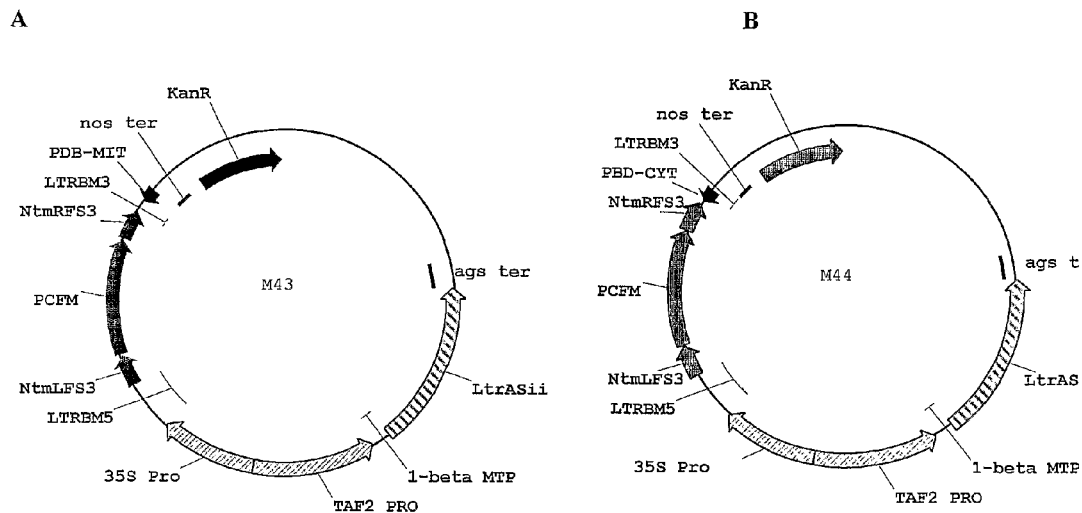

FIG. 9: Tobacco mitochondria transformation constructs
(A) M43 construct: PBD-MIT was fused to the 3' end of the LtRB intron
(B) M44 construct: PBD-CYT was fused to MTU PBD-MIT: Primer binding domain designed to anneal with t-RNAmet from mitochondria to initiate reverse transcription. LTRB5, LTRB3: 5' and 3' sequences of the LTRB intron, respectively. NtmLFS3: tobacco mitochondria left flanking sequence. NtmRFS3: tobacco mitochondria left flanking sequence. PCFM: CMS-inducing open reading frame from petunia. 35S pro: promoter from CaMV (Cauliflower mosaic virus). TAF2 Pro: *Arabidopsis* promoter. 1-beta MTP: mitochondria transit peptide from ATPase 1 beta subunit. LTRASii: sequence coding for the LTRA protein. Ags ter and nos ter: transcription terminator sequences from agrobactérium. KanR: NPTII gene for kanamycin resistance.

Figure 10:
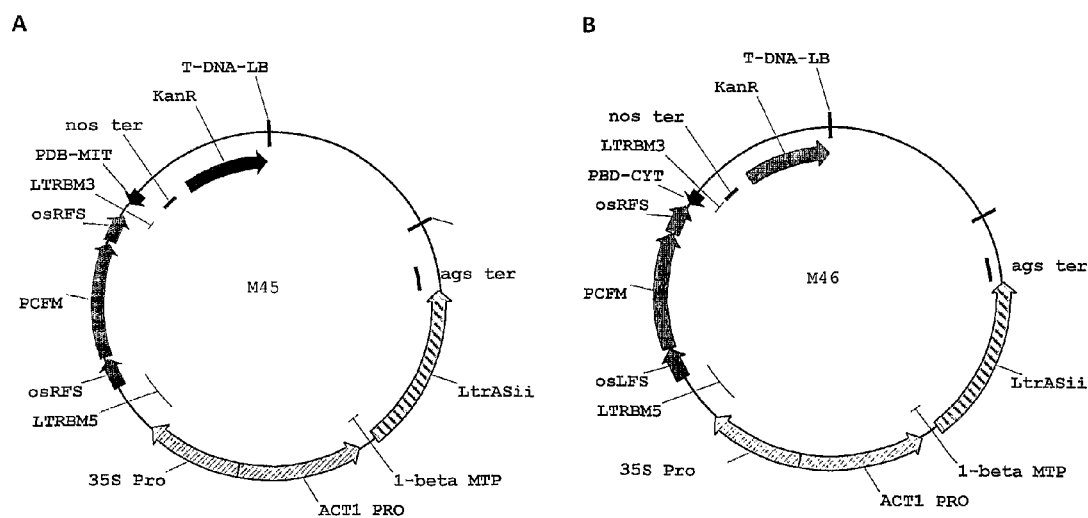

FIG. 10: Rice mitochondria transformation constructs
(A) M45 construct: PBD-MIT was fused to the 3' end of the LtrB intron
(B) M46 construct: PBD-CYT was fused to MTU PBD-MIT: Primer binding domain designed to anneal with t-RNA Met from mitochondria to initiate reverse transcription. LTRB5, LTRB3: 5' and 3' sequences of the LTRB intron, respectively. osLFS3: rice mitochondria left flanking sequence. osRFS3: rice mitochondria left flanking sequence. PCFM: CMS-inducing open reading frame from petunia. 35S pro: promoter from CaMV (Cauliflower mosaic virus). Act1 Pro: rice promoter from the actin gene. 1-beta MTP: mitochondria transit peptide from ATPase 1 beta subunit. LTRASii: sequence coding for the LTRA protein. Ags ter and nos ter: transcription terminator sequences from agrobactérium. KanR: NPTII gene for kanamycin resistance.

EXPERIMENTAL SECTION 1A

A Novel Approach for Plant Mitochondria Transformation

A new method for transformation of the plant mitochondrial genome comprises
(1) a plant mitochondria transformation unit (MTU) consisting of 3 major domains:
   (i) a plant mitochondria translocation sequence (MTS),
   (ii) a plant mitochondria transgene cassette
   (iii) a primer binding domain (PBD) which uses plant mitochondria tRNA-fMet or any other mitochondrial RNAs as a primer for reverse transcription;
(2) a reverse Transcriptase-RNase H(RT-RH) from retrotransposons, retroviruses, intron maturases or any protein with reverse transcription activity is fused to a plant mitochondria transit peptide for targeting into the plant mitochondria;
(3) an RNA binding protein that binds to the plant mitochondria translocation sequence (MTS), fused to a plant mitochondria transit peptide (FIG. 1).

Technology Rationale

The process of plant mitochondria transformation comprises two steps (see FIG. 2).

(1) Targeting of an RNA-Protein Complex to the Plant Mitochondria

The mitochondria transformation construct is expressed from the nucleus using a constitutive promoter. After delivery of the mitochondria transformation construct into the plant cell a strong expression of the RNA which contains the mitochondria translocation sequence (MTS), transgene cassette and primer binding domain (PBD) is achieved. The MTS binding protein (MTS-BP) fused to a plant mitochondria transit peptide, is also expressed on co-delivery from the same or a different nuclear transformation vector. It is used to bind to MTS and facilitate the translocation of the MTU RNA into the mitochondria.

Once the plant mitochondria transformation vector is presented in the plant cell via nuclear transformation, the mitochondria will then be permanently bombarded by the expressed MTS-BP/MTU RNA complex. Such stable and continuous pumping of the complex into the targeted organelle is a prerequisite for achieving a high efficiency of organelle transformation. The technology exploits the finding that the plant mitochondria transit sequence is sufficient to permit the whole MTS-BP/MTU RNA complex to be then taken up by the mitochondria.

The plant mitochondrial translocation sequences (MTS) can be selected from a number of RNA sequences such as mitoviruses, viral RNAs (including viral coat protein binding domains), group I and group II intron RNAs, retrotransposon primer binding sites, or any RNA that harbors a domain recognised by RNA binding proteins.

The MTS-binding protein can be any RNA binding protein that recognises and binds to specific RNA domains.

The plant mitochondrial transit peptide can be derived from any mitochondria-targeted proteins.

The fusion of MTS-BP to a mitochondrial transit peptide enables this protein to act as a carrier of RNA molecules into the plant mitochondria provided that these RNA molecules carry the corresponding MTS domain.

(2) Reverse Transcription of the Transgene Cassette and Insertion into the Plant Mitochondria Genome.

Once the MTU RNA is inside the mitochondria, its' primer binding domain (PBD) captures tRNA-fMet as a primer to form a template ready for reverse transcription. Simultaneously, a reverse transcriptase (RT-RH) fused to a plant mitochondria transit peptide is expressed from the nucleus using a constitutive promoter. It is targeted into the mitochondria where it facilitates reverse transcription of the MTU-RNA into single stranded DNA.

This is followed by insertion of the reverse transcribed cassette into the plant mitochondrial genome using homologous recombination between sequences flanking the transgene cassette (LFS, RFS) and the homologous regions in the plant mitochondria genome.

The Primer binding domain (PBD) is designed to capture the RT-RH protein and plant mitochondria tRNA-fMet (or any other plant mitochondrial tRNAs) as a primer, to initiate reverse transcription of the MTU RNA, carrying the plant mitochondria transgene cassette, into single-stranded DNA.

Once the population of organelle genomes has been transformed in the initial plant line, the nuclear encoded transgenes are no longer required and can then be removed through segregation in subsequent plant generations, leaving a clean organelle transformed plant line (FIG. 2).

Materials and Methods.
Part 1~Nucleic Acid Sequence Information
1. Preparation of a Group II Intron-Based Plant Mitochondria Translocation Sequence (MTS).

The LtrB intron from *Lactococcus lactis* lacking the gene coding for LTRA (intron-encoded maturase) was synthesised by a commercial DNA synthesis provider (Bio S&T Inc., Montreal (Quebec), Canada). Potential splicing donor and acceptor sites were mutagenised to prevent splicing for optimum accumulation of the groupII intron RNA in plant cytoplasm, the resulting group II intron sequence was named LtrBM.

The domain for insertion of the plant mitochondria transgene cassette (AscI-MluI-NotI sites) is underlined and shown in bold letters.

LtrBM Intron Sequence

SEQ ID NO. 1
```
GGATCCCTCGAGGTGCGCCCAGATAGGGTGTTAAGTCAAGTAGTTTA
AGGTACTACTCAGTAAGATAACACTGAAAACAGCCAACCTAACCGAA
AAGCGAAAGCTGATACGGGAACAGAGCACGGTTGGAAAGCGATGAGT
TAGCTAAAGACAATCGGCTACGACTGAGTCGCAATGTTAATCAGATA
TAAGCTATAAGTTGTGTTTACTGAACGCAAGTTTCTAATTTCGGTTA
TGTGTCGATAGAGGAAAGTGTCTGAAACCTCTAGTACAAAGAAAGCT
AAGTTATGGTTGTGGACTTAGCTGTTATCACCACATTTGTACAATCT
GTTGGAGAACCAATGGGAACGAAACGAAAGCGATGGCGAGAATCTGA
ATTTACCAAGACTTAACACTAACTGGGGATAGCCTAAACAAGAATGC
CTAATAGAAAGGAGGAAAAAGGCTATAGCACTAGAGCTTGAAAATCT
TGCAAGGCTACGGAGTAGTCGTAGTAGTCTGAGAAGGCTAACGGCCT
TTACATGGCAAAGGGCTACAGTTATTGTGTACTAAAATTAAAAATTG
ATTAGGGAGGAAAACCTCAAAATGAAACCAACAATGGCAATTTTAGA
AAGAATCAGTAAAAATTCACAAGAAAATATAGACGAAGTTTTTACAA
GACTTTATCGTTATCTTTTACGTCCTGATATTTATTACGTGGCGGGC
GCGCCACGCGTGCGGCCGCTGGGAAATGGCAATGATAGCGAAAGAAC
CTAAAACTCTGGTTCTATGCTTTCATTGTCATCGTCACGTGATTCAT
AAACACAAGTGAATTTTTACGAACGAACAATAACAGAGCCGTATACT
CCGAGAGGGGTACGTACGGTTCCCGAAGAGGGTGGTGCAAACCAGTC
ACAGTAATGTGAACAAGGCGGTACCTCCCTACTTCACCATATCATTT
TTAATTCTACGAATCTTTATACTGGCAAACAATTTGACTG
```

2. Mitochondria Transgene Cassettes

Positions of the various mitochondria sequences described below are derived from GenBank sequence accession numbers NC_006581 (*Nicotiana tabacum* mitochondrion) and NC_001284 (*Arabidopsis thaliana* mitochondrion).

2.1 Left and Right Flanking Sequences Used for Homologous Recombination

The mitochondria transgene cassette contains left and right flanking sequences (LFS and RFS) for insertion of the whole cassette into the mitochondrial genome using homologous recombination.

LFS and RFS sequences were amplified from coding and non-coding sequences of the mitochondrial genome of *Nicotiana tabacum* (NtmLFS, NtmRFS) and *Arabidopsis Thaliana* (AtmLFS, AtmRFS) using the primers described below.

2.1.1 NtmLFS1 and NtmRFS1, corresponding to corresponding to *Nicotiana tabacum* mitochondria non-coding sequences (position 292641-293235 and 293262-293835, respectively) were amplified from tobacco total cellular DNA using the following primers:

NtmLFS1:

IM101

SEQ ID NO. 2
GCGGGCGCGCCTATTACTCTCGGTCCTTGTTC

IM102

SEQ ID NO. 3
GCGGAGCTCTACCCTTTAAGACTCAATTACATCGAG

NTmRFS1:

IM103

SEQ ID NO. 4
GCATGCATTGCATAAGTAATCTCTTTTCTTATGAG

IM104

SEQ ID NO. 5
ACTAGTAAGGGGATTTGCCACATCGTTG

NtmLFS1 sequence:

SEQ ID NO. 6
```
TATTACTCTCGGTCCTTGTTCTTGGTCTCTGTGAAAGATCCAGTCGA
TGGGAATGAATCCATGTTCAAATCTTATTACCGGGTTCGATTACGGG
AAGGAAATAGAGAAGGTAAGGGACCGCTTTCCTTGTTCAAGCCGGTA
TTGTTTGAGTAAGTAGTAAGTAAGTGAGAAGTGGTGAATTGGCCAGG
AGGAATAAAGCTTATTTCAAGTACTAATAAAAGCATTCATTACAAAC
TCTTGTGCTCACTTATCCCAAGTATAGGATGTTTTCCCTGAGCCTGT
CTGTGTTGAATACGCTTTTTCCGTGTAGAATAGAGATTCTCTCTAAG
GTTGATAGAATATACGTTTTCTTTCTCTGATTAAAGGTTGTCCAAAG
AGGACTAAGAGACAGATGCTGTGCTTGCAAGTAAGCTTCAGCCAAGC
ATCAGATAAACCAAGTTCGGGTTGGGAAAAGGGCTATTTACCCCAGC
AATATAGAATAATTATTACCCCCAGCACATCCCCAAATGAGAGCATC
GTCTTTACCCCTAGAAAAGGTGCGATGTAATTTCCTGGTTCGATTAC
ATTGCTCGATGTAATTGAGTCTTAAAGGGTAGAGCTC
```

NtmRFS1 sequence:

SEQ ID NO. 7
```
ATTGCATAAGTAATCTCCTTTCTTATGAGAACTACGAATCATCCTCA
TGAATAAGCTCTACTCTACCTTAAGGAGATGTGGAGGCAATAGGTCC
CGTGCAGCTTTAACTAACTCTACTCCTCCATACGCCTATCCTTTAGT
TTAGTGGGCCAGGTCCTCCAGCCTTCCATTAGCTTTCGATTTAGTTT
GCATTCAAAGTCTTGGAATGCGAGCTTATGTGCTTTCAGGTATAGGC
ACCATTCGCCTGACTTTCTTGAAGTCCTAGGATTCTCCCCTAGTATT
CCATTCTCTCCCCCTCTCGGCCTTGCTTTCATTCCTGTCTCATTTGA
AATTGCTCCTAAGGCAGGGAGTCTTCTCGAAGCTGTCTAAGTCTTGT
AAGGCTCCTATATCTATATATAGAGAGGTCATGGTATGGAGGGAGGA
TTTCTACGCGCAACATCGTGGTTGGGGCATTCCTCCTTCTTTTAAAA
```

```
GAAGACTAGAGGACGAAAGAAGAAGCTCTTACATCGGATAAAGCCTA

ATTCCACTGTCCTTTGAAGATTGGAAGATAGTGAAGGCCGACTTCCT

TTTTAAAGATCACTCAACGATGTGGCAAATCCCCTTACTAGT
```

2.1.2 NtmLFS3 and NtmRFS3, corresponding to *Nicotiana tabacum* mitochondria sequences (position 85896-86331 and 86332-86860, respectively) were amplified from tobacco total cellular DNA using the following primers:
NtmLFS3

```
IM263    GGCGCGCCAGCAGATTTCCTCCCTCTATC    SEQ ID NO. 8

IM264    GCATGCAGATCGACGACGGAACGAAGAAC    SEQ ID NO. 9
```

NtmRFS3

```
IM265    TCTAGATCCAATTTCTTCCGGTATGC       SEQ ID NO. 10

IM375    CCGCGGTACGGTCCGTGCGCCGTT         SEQ ID NO. 11
```

NtmLFS3 Sequence:

```
                                                  SEQ ID NO. 12
AGCAGATTTCCTCCCTCTATCAACTCCTTTTTTATGGTCGGGAGGAT

CCACAATTCTTCATTGATCCACAAGACCTGGATTCCATACTGAGGGT

GCACCTTGAACCCTTAGAATTCAATCACCCTGCTCTATGCCAGGTCT

TAGAAAGTCTATGTGTCGAGAAGCATGATTCCCCTTTTTATCAAGAT

GTAAAAATGGCTCAAGCGCATCATTTTCGTGGCTTTATAAACTTAAA

GCACCAAGCGAAATTGGAAATGCAACATCGCCTAGAGTTAGGAGAGG

TATGGAAATCTCTTGAGAGAAGGAACGCTTTTCTAAGCCAGGAAAAC

GCCTCTCTAAGAGAAAAACTTTTAATTCTCGACAGGGAAGCCCCATA

GAAATTCTTCTTTGTTGTTGCTATCCTAAAATTGCGTTCTTCGTT

CCGTCGTCGATCT
```

NtmRFS3 Sequence:

```
                                                  SEQ ID NO. 13
TCTAGATCCAATTTCTTCCGGTATGCCGCTCCGCCAGCAAGGAGCGA

AAGAACCAAGTTTTCTGTGGTGATGTCAGAATTTGCACCTATTTGTA

TCTATTTAGTGATCAGTCCGCTAGTTTCTTTGCTCCCACTCGGTCTT

CCTTTTCTATTTTCTTCCAATTCTTCGACCTATCCAGAAAAATTGTC

GGCCTACGAATGTGGTTTCGATCCTTCCGGTGATGCCAGAAGTCGTT

TTGATATAAGATTTTATCTTGTTTCCATTTTATTTATTATTCCTGAT

CCGGAAGTAACCTTTTCCTTTCCTTGGGCAGTACCTCCCAACAAGAT

TGATCCGTTTGGATCTTGGTCCATGATGGCCTTTTTATTGATTTTGA

CGATTGGATCTCTCTATGAATGGAAAAGGGGTGCTTCGGATCGGGAG

TAACCACTAGTGAGAGGGCAAAAATTGGGGGGAAGGACAAAGGAAAG

AGCGATGCCTACATTAAATCAATTGATTCGTCATGGTAGAGAAGAAA

AACGGCGCACGGACCGTA
```

2.1.3 NtmLFS4 and NtmRFS4 corresponding to *Nicotiana tabacum* mitochondria sequences position 24888-24579 and 24578-24269 respectively (on the complementary strand).

NtmLFS4 corresponds to the 5' end of the gene coding for ATP6 and can be used for translational fusion with any gene of interest, promoter activity is provided by the ATP6 promoter upstream of NtmLFS4 on the tobacco mitochondrial genome and termination of transcription is achieved with the ATP6 terminator sequence within NtmRFS4. Any plant mitochondrial coding sequence can be used instead of ATP6 to achieve expression of any gene of interest.

NtmLFS4 and NtmRFS4 were amplified from tobacco total cellular DNA using the following primers:
NtmLFS4

```
IM376    GGCGCGCCAGGGTATGATACCTTATAGCT    SEQ ID NO. 14

IM287    CTCGAGTGAGACTCGCTTTTGTTC         SEQ ID NO. 15
```

NtmRFS4

```
IM289    GAGCTCATGGGTATACTTAGTCGTGG       SEQ ID NO. 16

IM377    CCGCGGCTGAGATAGCTCCGTAAACTAAT    SEQ ID NO. 17
```

NtmLFS4 Sequence:

```
                                                  SEQ ID NO. 18
CCAGGGTATGATACCTTATAGCTTCACAGTTACAAGTCATTTTCTCA

TTACTTTGGGTCTCTCATTTTCTATTTTTATTGGCATTACTATAGTG

GGATTTCAAAAAAATGGGCTTCATTTTTTAAGCTTCTTATTACCTGC

AGGAGTCCCACTGCCATTAGCACCTTTTTTAGTACTCCTTGAGCTAA

TCCCTTATTGTTTTCGAGCATTAAGCTCAGGAATACGTTTATTTGCT

AATATGATGGCCGGTCATAGTTCAGTAAAGATTTTAAGTGGGTTCGC

TTGGACTATGCTATGTATGAATGATCTTTTATATTTCATAGGGGATC

TTGGTCCTTTATTTATAGTTCTTGCATTAACCGGTCTGGAATTAGGT

GTAGCTATATCACAAGCTCATGTTTCTACGATCTTAATCTGTATTTA

CTTGAATGATGCTATAAATCTTCATCAAAGTGCTTCTTTTTTTATAA

TTGAACAAAAGCGAGTCTCA
```

NtmRFS4 Sequence

```
                                                  SEQ ID NO. 19
ATGGGTATACTTAGTCGTGGAGCATTCCGAGTATTTGCTTTAGGGAT

CGTTCCTGCGCATCTCCTTACTTTATAGCAGTTATTGCTCCGGTTCC

AGAAGGTATAGCTCTCGCCTCAGCTTTTTCTTTGAAATCGGAGACTG

TTCCAATTTCCTACTGAGATAGGCAAGCGGAGGGAGAACTAGACGTA

TCTTGCTAGGCAAAGACAGGTTAGAATGGATAGCTCGCGGGTGGGAT

TGACGGGATAGATCACTATTGCAGAAGGAGGTAGAACCGGGGGAAGA

ATTATGGCTATAAAGGTCCTCGCCCTCTTAGGCACATGGTTCTAAAG

ATTAAATCTCAAAGCGGTACTAAAGATTAGGCAGAAGAAGAACTAGA

ACTAGAATTCTTCGCCCCTCCCCTTGTACCAAGAAGCAAGTTCAGAA

CATAAGGATAATGGGCTCGTCTATTATAAGTTATTAGTTTACGGAGC

TATCTCAG
```

2.1.4 AtmLFS5 and AtmRFS5 corresponding to *Arabidopsis thaliana* mitochondria sequences (position 344225-344571 and 344572-344926, respectively) were amplified from *Arabidopsis* total cellular DNA using the following primers:
AtmLFS5

```
                                   SEQ ID NO. 20
    IM398    GGCGCGCCGGGAGGAAGCTGGGCCAGTAGT

SEQ ID NO. 21
    IM399    GCATGCGAAAAATAAAGAAAGAAGCAAAAGCCCAT
```

AtmRFS5

```
IM400  ATCGATATGCCGCTTCTTCGCCA      SEQ ID NO. 22

IM401  CCGCGGATTTTGTGCCCTATCACTTTAC SEQ ID NO. 23
```

AtmLFS5 Sequence

```
                                                SEQ ID NO. 24
GGGAGGAAGCTGGGCCAGTAGTCCCCTATCCATACAGGAGGGATGAA

ATGATTGGGGGGATAGCGTAGAGGCGATAGAACGCCGCCTTCTGGC

GAAATACCCCGAAGGCTCTCCCTCTGCGGAGATCATAGAGATGGCCC

GAATAGAGGCCGAAGATCTATTCGAGATCAAAGCCCAAATCATCCAA

CGGATGGCTCTATATGACCCAACCGGCGATTGGATGGCGCGTGGGGC

TCGGGCCCTCGATAATCCGAGGACCACTAGTGGGGAAGAGTCCTTGG

AGCGTCTTTATGATATATGGAAGGACCTCCAAGAAACCGGGCCCCTC

TCGGACGAGTTTTCTCGTTTACAAGAGAAAGTATTCCTCAAGAAAGG

CGGCCCTGGGGGGGACCCTATCGCATAAGGTCTGCAAGCCTTTCGGG

ATGGGCTTTTGCTTCTTTCTTTATTTTTCG
```

AtmRFS5 Sequence

```
                                                SEQ ID NO. 25
ATATGCCGCTTCTTCGCCAGCAAGGAGCGAGAAAACAAAGTGGGCTG

TAATGATGTCAGAATTTGCACCAATTTCTATCTATTTAGTGATTAGT

CTGCTAGTTTCTTTGATCCTACTCGGTGTTCCTTTTCCATTTGCTTC

CAATAGTTCTACCTACCCAGAAAAATTGTCGGCCTACGAATGTGGTT

TCGATCCTTCCGGTGATGCCAGAAGTCGTTTCGATATACGATTTTAT

CTTGTTTCAATTTTATTTTTAATCCCTGATCTGGAAGTAACCTTTTT

CTTTCCTTGGGCAGTACCTCCCAACAAGATTGATCTGTTTGGATTTT

GGTCCATGATGGCCTTTTTATTTATTTTGACGATTGGATTTCTATAT

GAATGGAAAAGGGGTGCTTCGGATCGGGAGTAAAGTGATAGGGCACA

AAAT
```

2.2 Plant Mitochondria Promoter and Terminator Sequences
2.2.1 ATP6 promoter sequences were amplified from total cellular DNA of *Nicotiana tabacum* (NtATP6-PRO) and *Arabidopsis thaliana* (AtATP6-PRO) using the following primers:
NtATP6-PRO

```
IM364  GGCGCGCCTCTAGTCGAATAGAGTATTAG   SEQ ID NO. 26

IM365  ATCTCGAGTGTGATTGAGATAAAAAGATTCC SEQ ID NO. 27
```

AtATP6-PRO

```
                                               SEQ ID NO. 28
IM346    CTGCATGCTCCTCTACTGAGTCAGTGACAG

SEQ ID NO. 29
IM347    ATTCTAGAATTGGATTAATTGATTTCAACAAAATG
```

NtATP6-PRO Sequence

```
                                                SEQ ID NO. 30
CCTCTAGTCGAATAGAGTATTAGTCCGCTCCATTATATTCCCCATTATTT

CACTTTCTCGCTATTCGAAATATCATAAGAGAAGAAAGCTGGCAGGTTGG

ATCCTAGGGTAGATTCCTGCTGTTGAATGATCGACTAGCTTCCTCTTTAG

TTCTTTGATATTGGGTTCGTGTTCAGTGTACCGCTCTTTTTATATATGAA

ATTACTTCGTCCTTTTTTTAGCCCTTTTTCGTTTGTCCATCTTTTTTTC

TCCCATGCTTTCCGTTGGTCAACAACCAACCAAAGTGCTCTATACTTCTT

CACTACTCGTACAGGCTTGACGGAGTTAAGCTGTATTGAGGGAATCTTTT

TATCTCAATCA
```

AtATP6-PRO Sequence

```
                                                SEQ ID NO. 31
TCCTCTACTGAGTCAGTGACAGAAGTGCAGCAGCCAATAATACGTATATA

AGAAGAGGACTGCTTACGGGATCAAACTATCAATCTCATAAGAGAAGAAA

TCTCTATGCCCCTTTTTCTTGGTTTTCTCCCATGCTTTTGTTGGTCAAC

AACCAACCACAACTTTCTATAGTTCTTCACTACTCCTAGAGGCTTGACGG

AGTGAAGCTGTCTGGAGGGAATCATTTTGTTGAAATCAATTAATCCAAT
```

2.2.2 ATP6 terminator sequence was amplified from total cellular DNA of *Nicotiana tabacum* (NtATP6-TER) using the following primers:

```
IM289GAGCTCATGGGTATACTTAGTCGTGG        SEQ ID NO. 32

IM366CCGCGGCGAGGACCTTTATAGCCATAATTC    SEQ ID NO. 33
```

NtATP6-TER Sequence

```
                                                SEQ ID NO. 34
ATGGGTATACTTAGTCGTGGAGCATTCCGAGTATTTGCTTTAGGGATCGT

TCCTGCGCATCTCCTTACTTTATAGCAGTTATTGCTCCGGTTCCAGAAGG

TATAGCTCTCGCCTCAGCTTTTTCTTTGAAATCGGAGACTGTTCCAATTT

CCTACTGAGATAGGCAAGCGGAGGGAGAACTAGACGTATCTTGCTAGGCA

AAGACAGGTTAGAATGGATAGCTCGCGGGTGGGATTGACGGGATAGATCA

CTATTGCAGAAGGAGGTAGAACCGGGGGAAGAATTATGGCTATAAGGTC

CTCG
```

2.3 Transgene Sequences
2.3.1 Green Fluorescent Protein (GFP) Sequence

The GFP gene was synthesised according to GenBank accession number XXU70496

GFP Sequence

SEQ ID NO. 35
ATGAGTAAAGGAGAAGAACTTTTCACTGGAGTTGTCCCAATTCTTGTTGA

ATTAGATGGTGATGTTAATGGGCACAAATTTTCTGTCAGTGGAGAGGGTG

AAGGTGATGCAACATACGGAAAACTTACCCTTAAATTTATTTGCACTACT

GGAAAACTACCTGTTCCATGGCCAACACTTGTCACTACTTTCACTTATGG

TGTTCAATGCTTTTCAAGATACCCAGATCATATGAAGCGGCACGACTTCT

TCAAGAGCGCCATGCCTGAGGGATACGTGCAGGAGAGGACCATCTCTTTC

AAGGACGACGGGAACTACAAGACACGTGCTGAAGTCAAGTTTGAGGGAGA

CACCCTCGTCAACAGGATCGAGCTTAAGGGAATCGATTTCAAGGAGGACG

GAAACATCCTCGGCCACAAGTTGGAATACAACTACAACTCCCACAACGTA

TACATCACGGCAGACAAACAAAAGAATGGAATCAAAGCTAACTTCAAAAT

TAGACACAACATTGAAGATGGAAGCGTTCAACTAGCAGACCATTATCAAC

AAAATACTCCAATTGGCGATGGCCCTGTCCTTTTACCAGACAACCATTAC

CTGTCCACACAATCTGCCCTTTCGAAAGATCCCAACGAAAAGAGAGACCA

CATGGTCCTTCTTGAGTTTGTAACAGCTGCTGGGATTACACATGGCATGG

ATGAACTATACAAATAA

2.3.2 Gene for Induction of Cytoplasmic Male Sterility

The sequence coding for the PCFM gene was based on the petunia mitochondria PCF gene responsible for induction of CMS. It comprises a promoter, open reading frame and 3' untranslated sequence. It was modified to remove putative splicing sites for optimum expression of the PCFM RNA in the cytoplasm on transit to the mitochondria.

PCFM was synthesised using a commercial DNA synthesis provider (Bio S&T Inc., Montreal (Quebec), Canada).

The location of mutagenised donor sites are underlined
PCFM Sequence

SEQ ID NO. 36
GAACTCAATGGGCCAGTTATAGCATCCTGCTTCTTCTTACAAAAGAAAT

TTCATAAGATAAGAGAGATGAGGCAAAGAAGGAATTGATAGAGGTGCGGC

GAGAAGTTCAATACCTTCTTGATCGAGAAAATGTCCTTGCTTGTACTTCT

CTTTCTTTATCGAGATTGGGTTGGTGTTCAGTGTACCGCTTGTCTAGCCT

ATGCTTTGCATGAACATCTCAATGTCCAAGATAAAAGAACGAGGGGAAG

AATCGACGAGGCCAGTGTTCTCGAAGAGAAATCGTGATGGAAAAGCGT

GAGGAGAATTCGAAACTCGAGATGTTAGAAGGTGCAAAATCAATGGGTGC

AGGAGCTGCTACAATTGCTTCAGCGGGAGCTGCTATCGGTATTGGAAACG

TCCTTAGTTCCTCGATTCATTCCGTTTTAGGGATACAAATAACAGACTTA

CATCACGATGTCTTTTTCTTCGTTATTCTGATTTTGGTTTTCGTATCATG

GATCTTGGGTCGCGCTTTATGGCATTTCCACTATAAAAAAATCCAATCC

CGCAAAGGATTGTTCATGGAACTACTATCGAGATTCTTCGGACCTTATTT

CCTAGTATCATCCCTATGTTCATTGCTATACCATCATTTGCCCTGTATGG

GTATTCGGACTATAACAGTTCCGATGAACAGTCACTCACTTTTGACAGTT

ATACGATTCCAGAAGATGATCCAGAATTGGGTCAATCACGTTTATTAGAA

GTCGACAATAGAGTGGTTGTACCAGCAAACAGTTCTCTCCGTTTTATTGT

AACATCTGCGGCTGTACCTTCCTTAGGTGTCAAAGGTGATGCTGTGCCTT

CCTTAGGTGTCAAAGGTGATGCTGTGCCTTCCTTAGGTGTCAAAGGTGAT

GCTGTGCCTGGGCCTGGGCGGGTTTTTCAGACTTGGACCCGAGCTTTTGA

GCGTTTGGGCCTGTTGACGGTTGCCCATTGCGCCGGCACCGGAACATCAA

GCTCGGGCTCGGTAGTCAGTCTTCCACAGGACGAAATATGGGCCGCCCTT

GAGGGCGATCCCCAGGCCCTTCCGGAAGACGGGCAATTTCACGCCGTCGC

CCCTGAGGGGAATCCCCAGGCCCTTCCGGAAGACGGGCAATTTCACGCCG

TCGCCCCTGAGGGGAATCCCCAGGCCCTTCCGGAAGACGGGCAATTTCAC

GCCGTCGCCCCTGAGGGGAATCCCCAGGCCCTTCCGGAAGACGGGCAATT

TCACGCCATCGCCTTTGACCCTCTTATAGCAACACGGCAAGACGCGTGGA

ATACGCTACTTGTCTTGTTGCGGCGCAGCACCAAAATTGAGCCTAAGGCC

AATTTTGTTACTAAAGCAGGGGAAGATCTTGGTATAGATACCGCAGACCC

TGTTCGCCTTGACAAGTTAGTACGGGTACTGAACACGTATATCCAACTCG

CCCCATTAGAAAGCGGGAGAAAGGTCCTCCAAAACCTGAAAGCCACGATG

GCTGAATGGGAAAAGAACGGAAGGCCC<u>T</u>AAGTGGTGTCGTGTACTTTTTT

CAATTATAATTAAATAAAAGGAGGTTACCGAATTTACGCGGTGGCCCTTT

TATGTATGTTGCTGTCGTAAAGTTTCGTTCT

2.4 Primer Binding Domain for Reverse Transcription

A Primer Binding Domain (PBD) was designed to capture the plant mitochondria tRNA-fMet as described by Friant et al., (1998) to be used as a template for reverse transcription PBD was constructed by overlapping PCR using the set of following primers:

IM374
SEQ ID NO. 37
TTCCGCGGCCTATCTCACATTCACCCAATTGTCA

IM368
SEQ ID NO. 38
TTAGAAGTATCCAATGCACAGTAGGTACCATGACAATTGGGTGAA

IM369
SEQ ID NO. 39
ATTGGATACTTCTAAGGAAGTCCACACAAATCAAGAACCATTAGA

IM370
SEQ ID NO. 40
CTCACATTCTTCTGTTTGGTTAGATGAAACGTCTAATGGTTCTTGA

PBD MIT

SEQ ID NO. 41
TATCTCACATTCACCCAATTGTCATGGTACCTACTGTGCATTGGATACTT

CTAAGGAAGTCCACACAAATCAAGAACCATTAGACGTTTCATCTAACCAA

ACAGAAGAATGTGAGAAGGCTTCCACTAAGGCTAACTCTCAACAGACAAC

3 Mitochondria Transit Peptide (mTP)

The sequence coding for the Mitochondrial ATPase 1β subunit transit peptide (1β-mTP) was amplified from total tobacco cellular DNA with the following primers:

Proteins translationally fused to 1β-mTP can be driven inside the plant mitochondria.

IM267  ATACTCGAGTCTCTCTCTACTCCTTTCAC  SEQ ID NO. 42

IM268  ATAGCATGCTGATGGCTGAGATGCCGGTG  SEQ ID NO. 43

1β-mTP Sequence

SEQ ID NO. 44
TCTCTCTCTACTCCTTTCACTCTCTCTCTAGCCAAACCCTCCACCATGGC
TTCTCGGAGGCTTCTCGCCTCTCTCCTCCGTCAATCGGCTCAACGTGGCG
GCGGTCTAATTTCCCGATCGTTAGGAAACTCCATCCCTAAATCCGCTTCA
CGCGCCTCTTCACGCGCATCCCCTAAGGGATTCCTCTTAAACCGCGCCGT
ACAGTACGCTACCTCCGCAGCGGCACCGGCATCTCAGCCATCA

4 Mitochondria-Targeted Reverse Transcriptase-RNaseH Protein

The reverse transcriptase-RNase H gene from the yeast Ty1-H3 retrotransposon (Boeke et al., Mol. Cellul. Biology (1988), 8: 1432-1442; bank accession No. M18706) was optimised for codon usage in plants and by insertion of 5 introns from the *Arabidopsis* genome (intron 1—from At1g04820, intron 2—from At2g29550, intron 3—from At1g31810, intron 4 and 5—from At1g09170). The gene was synthesised by a commercial DNA synthesis provider and fused to the sequence coding for the mitochondria transit peptide 1β-mTP. The resulting gene was named mRTRHi-Ty1. The introns are underlined and shown in bold letters. The sequence coding for 1β-mTP is in italics lower case.

mRTRHi-Ty1 Sequence

SEQ ID NO. 45
*ctcgagtctctctctactcctttcactctctctctagccaaaccctccac*
*catggcttctcggaggcttctcgcctctctcctccgtcaatcggctcaac*
*gtggcggcggtctaatttcccgatcgttaggaaactccatccctaaatcc*
*gcttcacgcgcctcttcacgcgcatcccctaagggattcctcttaaaccg*
*cgccgtacagtacgctacctccgcagcggcaccggcatctcagccatcag*
*catgc*ATGAACAATTCATCCCACAACATCGTTCCTATCAAGACTCCAACT
ACTGTTTCTGAGCAGAACACTGAAGAATCTATCATCGCTGATCTTCCACT
TCCTGATCTTCCTCCAGAATCTCCTACTGAATTTCCTGATCCATTCAAAG
AACTTCCACCTATCAACTCAAGACAAACTAACTCTTCATTGGGCGGAATT
GGCGATTCTAATGCTTACACTACTATCAACTCTAAGAAGAGGTATTGTAG
CCAGCCTCAACCAGTCTTTTTGCTGTTACATTTTCTTGGGCTCATCTAAT
GTTATTTTCCTATTTTGTTTTCAGGTCACTTGAAGATAATGAAACTGAAA
TCAAAGTTTCTAGGGATACATGGAATACTAAGAATATGAGATCACTTGAA
CCTCCAAGATCTAAGAAGAGAATCCATCTTATTGCAGCTGTTAAAGCTGT
GAAATCAATCAAACCAATTAGAACAACTCTTAGATACGATGAAGCAATTA
CATACAACAAAGACATCAAGGAGAAGGAGAAATACATCGAGGCTTACCAC
AAAGAAGTTAACCAACTTCTTAAGATGAAAACTTGGGATACTGATGAATA
CTACGATAGAAAAGAGATTGACCCTAAGGAGAGTTATCAACTCAATGTTCA
TCTTCAACAAGAAGAGAGACGGAACTCACAAAGCTAGATTCGTTGCAAGA
GGAGATATTCAGCATCCTGACACTTACGATTCAGGTAAGTATTCCAATGT
TCTTCGATTATGAGTCAATGTTGTTACTGTATCTGTCTCTGTGGTTTATT
GTTTCAGGCTTAGTTATTGATTAGTATTGAAACTTCACTCACATATTTTT
TTGTTTGTTTTCTGAATTGTGCAGGTATGCAATCTAATACTGTTCATCAC
TACGCATTGATGACATCTCTTTCACTTGCATTGGACAATAACTACTACAT
TACACAACTTGACATATCTTCTGCATACCTTTACGCTGATATCAAGGAGG
AGCTTTACATTAGACCTCCACCACATTTGGGAATGAATGATAAGTTGATC
CGTTTGAAGAAATCACTTTACGGATTGAAACAATCTGGAGCTAATTGGTA
CGAAACTATCAAATCATACCTTATTCAGCAATGCGGTATGGAGGAAGTTA
GGGGATGGTCATGCGTATTCAAGAACTCTCAAGTTACAATCTGCCTCTTC
GTTGATGATATGGTGCTCTTCTCTAAGAATCTTAACTCAAACAAGAGAAT
CATTGAGAAGTTGAAGATGCAATACGACACTAAGATCATCAACCTTGGAG
AATCTGATGAGGAAATTCAATACGACATTCTTGGATTGGAAATCAAATAC
CAAAGAGGTGAGTTATATTTAACAGCTCATCAGTTACTTAAACACTTTTT
GGGACAAGCAGTTCAAACTCATGTTCCAATCCTAAAATTAATTGCAATTC
ACAGGTAAGTACATGAAGTTGGGAATGGAAAACTCATTGACTGAGAAGAT
TCCTAAACTTAACGTTCCTTTGAATCCAAAGGGAAGAAAGCTCTCTGCTC
CAGGACAACCAGGACTTTACATTGACCAGGATGAACTTGAGATTGATGAG
GATGAATACAAGGAGAAAGTACACGAGATGCAGAAGTTGATTGGACTTGC
TTCATACGTTGGATACAAATTCAGATTCGACCTTCTTTACTACATCAACA
CACTTGCTCAGCATATACTTTTCCCATCTAGGCAAGTTCTTGACATGACA
TACGAGCTTATCCAATTCATGTGGGACACTAGAGACAAGCAACTCATATG
GCACAAGAACAAGCCTACAGAGCCAGATAACAAGCTCGTTGCAATCTCTG
ATGCTTCTTACGGAAACCAACCATACTACAAATCACAAATTGGAAACATC
TACTTGCTTAACGAAAGGTACTTTTCTCAAAGACTTTACCTTATTGTGG
AATATTGAATTTTCTGAAAGACTTCACCTTATCTACATTTGTAATTTTAC
TATGGTAATCAGGTGATTGGAGGAAAGAGCACTAAGGCTTCACTTACATG
CACTTCAACTACTGAGGCAGAGATCCACGCTATATCAGAATCTGTACCAC
TTCTTAACAACCTTTCTTACCTTATCCAAGAGCTTAACAAGAAGCCAATC
ATCAAGGGACTTCTTACTGACTCAAGATCAACAATCTCTATCATTAAGTC
TACAAATGAAGAGAAATTCAGAAACAGATTCTTCGGAACAAAGGCAATGA
GACTTAGAGATGAAGTTTCAGGTAAGTATTAACTTACCAAATGATCAATA
TTATTTTGAAATGCAGGTTTTAGAATAATACTCTCTGCCGTTCTTGTTTA
TTTCCAGGTAACAACCTTTACGTTTACTACATCGAGACTAAGAAGAACAT
TGCTGACGTTATGACAAAGCCTCTTCCTATCAAGACCTTCAAGTTGCTTA
CTAACAAATGGATTCATTA 5 MTS-Binding Protein (MTS-BP)

The LtrA protein from *Lactococcus lactis* encoded by the LtrB intron is able to bind to the LtrB intron-based plant mitochondria translocation sequence (MTS) described in part 1 and therefore serves as a MTS-binding protein. The sequence of the LtrA protein was first optimised for codon usage in plants and 5 plant introns were inserted into the coding sequence to improve LtrA expression in plants. The introns 1, 2 4 are from *Arabidopsis* gene At5g01290, intron 3 and 5 were selected from *Arabidopsis* gene At5g43940. The gene was synthesised by commercial DNA synthesis provider and fused to the sequence coding for the mitochondria transit peptide 1β-mTP. The resulting gene was named mLTRASi. The mLTRASi protein is able to bind to RNA molecules carrying the LtrB intron MTS and transfer these RNAs into the plant mitochondria.

Plant introns inserted in the coding sequence of the LtrA gene are underlined and shown in bold letters. The sequence coding for 1β-mTP is in italics lower case.

mLTRASi Sequence:

SEQ ID NO. 46
*ctcgagtctctctctactcctttcactctctctctagccaaaccctccac*

*catggcttctcggaggcttctcgcctctctcctccgtcaatcggctcaac*

*gtggcggcggtctaatttcccgatcgttaggaaactccatccctaaatcc*

*gcttcacgcgcctcttcacgcgcatcccctaagggattcctcttaaaccg*

*cgccgtacagtacgctacctccgcagcggcaccggcatctcagccatcag*

*catgc*ATGAAGCCAACAATGGCAATCCTCGAACGAATCTCTAAGAACTCA

CAGGAGAACATCGACGAGGTACAATAACCCATATATATGAATTGATTCAT

GTGTTACTCGTACTTGTTTGAATATGTTTGGAGCAAGTTTGATACTTTTG

GATGATGATATCGCAAATTCGTTATCTTTTTGGCGTTATAGGTCTTCACA

AGACTTTACCGTTACCTTCTCCGTCCTGACATCTACTACGTGGCATATCA

GAACCTCTACTCTAACAAGGGAGCTTCTACAAAGGGAATCCTCGATGATA

CAGCTGATGGATTCTCTGAGGAGAAGATCAAGAAGATCATCCAATCTTTG

AAGGACGGAACTTACTACCCTCAGCCTGTCCGAAGAATGTACATCGCAAA

GAAGAACTCTAAGAAGATGAGACCTCTTGGAATCCCAACTTTCACAGACA

AGTTGATCCAGGAGGCTGTGAGAATCATCCTTGAATCTATCTATGAGCCT

GTCTTCGAGGATGTGTCTCACGGTTTCCGACCTCAGCGAAGCTGTCACAC

AGCTTTGAAGACAATCAAGAGAGAGTTCGGAGGTAAATTATATGCTTTGC

CACTTCCTCAAAAGATCATTTTAGGTTCATTGGTATGTGGTTTTTTTCTT

AACAGGTGCAAGATGGTTCGTGGAGGGAGATATCAAGGGATGCTTCGATA

ACATCGACCACGTCACACTCATCGGACTCATCAACCTTAAGATCAAGGAT

ATGAAGATGAGCCAGTTGATCTACAAGTTCCTCAAGGCAGGTTACCTCGA

AAACTGGCAGTACCACAAGACTTACAGCGGAACACCTCAGGGCGGAATCC

TCTCTCCTCTCCTCGCTAACATCTATCTTCATGAATTGGACAAGTTCGTT

CTCCAACTCAAGATGAAGTTCGACCGAGAGAGTCCAGAGAGAATCACACC

TGAATACCGGGAGCTTCACAACGAGATCAAAAGAATCTCTCACCGTCTCA

AGAAGTTGGAGGGCGAGGAGAAGGCTAAGGTTCTCTTGGAATACCAGGAG

AAGAGGAAGAGGTTGCCTACACTCCCTTGTACATCACAAACAAACAAGGT

TCGTTCTCTCCATTTTCATTCGTTTGAGTCTGATTTAGTGTTTTGTGGTT

GATCTGAATCGATTTATTGTTGATTAGTGAATCAATTTGAGGCTGTGTCC

TAATGTTTTGACTTTTGATTACAGGTCTTGAAGTACGTCCGATACGCTGA

CGACTTCATCATCTCTGTTAAGGGAAGCAAGGAGGACTGTCAATGGATCA

AGGAGCAATTGAAGCTCTTCATCCATAACAAGCTCAAGATGGAATTGAGT

GAGGAGAAGACACTCATCACACATAGCAGTCAGCCTGCTCGTTTCCTCGG

ATACGACATCCGAGTCAGGAGAAGTGGAACTATCAAGCGATCTGGAAAGG

TTCAATTCTTTCTTTCACATTTGTACTTGTTCACTCGTTTTATTAATCCT

CTTTAGAATGGAGATTCTTACCTCTGTGTGGCCTTTGGCAGGTCAAGAAG

AGAACACTCAACGGGAGTGTGGAGCTTCTCATCCCTCTCCAAGACAAGAT

CCGTCAATTCATCTTCGACAAGAAGATCGCTATCCAGAAGAAGGATAGCT

CATGGTTCCCAGTTCACAGGAAGTACCTTATCCGTTCAACAGACTTGGAG

ATCATCACAATCTACAACTCTGAATTGAGAGGTAAGCTGCTACCTCAAAC

TTTCTAGTGCTTCCATATTTCCTTTCTTCTGCAAGGCAGAGAACCATTGT

GGTTAAGTGTTTTAAATTGTGAATGTATAGGTATCTGCAACTACTACGGT

CTCGCAAGTAACTTCAACCAGCTCAACTACTTCGCTTACCTTATGGAATA

CTCTTGCTTGAAGACTATCGCATCTAAGCATAAGGGAACACTCTCAAAGA

CCATCTCTATGTTCAAGGATGGAAGTGGTTCTTGGGGAATCCCTTACGAG

ATCAAGCAGGGGAAGCAGAGGAGATACTTCGCCAACTTCAGTGAATGCAA

ATCTCCTTACCAATTCACTGATGAGATCAGTCAAGCTCCTGTGCTTTACG

GAACGCTCGGAACACTCTTGAGAACAGACTTAAGGCTAAGTGTTGTGAGT

CTTTGTGGAACATCTGATGAGAACACATCTTACGAGATCCACCACGTCAA

CAAGGTCAAGAACCTTAAGGGAAAGGAGAAGTGGGAGATGGCAATGATCG

CTAAGCAGCGGAAGACTCTTGTTGTTTGCTTCCATTGTCATCGTCACGTG

ATCCATAAGCACAAGTGAACTAGTAA

6. Promoter and Terminator Sequences used for Expression of Nuclear Cassettes 6.1 Promoter Sequences 6.1.1 *Arabidopsis* Ubiquitin Promoter AtUbi3-PRO The 5' promoter region from *Arabidopsis* ubiquitin 3 gene was amplified with the following primers:

SEQ ID NO. 47
IM326    CGAAGCTTGAATTCTACCGGATTTGGAGCCAAGTC

SEQ ID NO. 48
IM327    AAGGATCCTCTAGATGTTTGGTGACCTGAAATAAAACAATAG

AtUbi3-PRO Sequence

SEQ ID NO. 49
TACCGGATTTGGAGCCAAGTCTCATAAACGCCATTGTGGAAGAAAGTCTT

GAGTTGGTGGTAATGTAACAGAGTAGTAAGAACAGAGAAGAGAGAGAGTG

TGAGATACATGAATTGTCGGGCAACAAAAATCCTGAACATCTTATTTTAG

CAAAGAGAAAGAGTTCCGAGTCTGTAGCAGAAGAGTGAGGAGAAATTTAA

GCTCTTGGACTTGTGAATTGTTCCGCCTCTTGAATACTTCTTCAATCCTC

ATATATTCTTCTTCTATGTTACCTGAAAACCGGCATTTAATCTCGCGGGT

TTATTCCGGTTCAACATTTTTTTTGTTTTGAGTTATTATCTGGGCTTAAT

AACGCAGGCCTGAAATAAATTCAAGGCCCAACTGTTTTTTTTTTTAAGAA

GTTGCTGTTAAAAAAAAAAAAAGGGAATTAACAACAACAACAAAAAAGA

TAAAGAAAATAATAACAATTACTTTAATTGTAGACTAAAAAAACATAGAT

TTTATCATGAAAAAAGAGAAAAGAAATAAAAACTTGGATCAAAAAAAA

ACATACAGATCTTCTAATTATTAACTTTTCTTAAAAATTAGGTCCTTTTT

CCCAACAATTAGGTTTAGAGTTTTGGAATTAAACCAAAAAGATTGTTCTA

AAAAATACTCAAATTTGGTAGATAAGTTTCCTTATTTTAATTAGTCAATG

GTAGATACTTTTTTTTCTTTTCTTTATTAGAGTAGATTAGAATCTTTTAT

GCCAAGTATTGATAAATTAAATCAAGAAGATAAACTATCATAATCAACAT

GAAATTAAAAGAAAAATCTCATATATAGTATTAGTATTCTCTATATATAT

TATGATTGCTTATTCTTAATGGGTTGGGTTAACCAAGACATAGTCTTAAT

GGAAAGAATCTTTTTTGAACTTTTTCCTTATTGATTAAATTCTTCTATAG

AAAAGAAAGAAATTATTTGAGGAAAAGTATATACAAAAAGAAAAATAGAA

AAATGTCAGTGAAGCAGATGTAATGGATGACCTAATCCAACCACCACCAT

AGGATGTTTCTACTTGAGTCGGTCTTTTAAAAACGCACGGTGGAAAATAT

GACACGTATCATATGATTCCTTCCTTTAGTTTCGTGATAATAATCCTCAA

CTGATATCTTCCTTTTTTTGTTTTGGCTAAAGATATTTTATTCTCATTAA

TAGAAAAGACGGTTTTGGGCTTTTGGTTTGCGATATAAAGAAGACCTTCG

TGTGGAAGATAATAATTCATCCTTTCGTCTTTTTCTGACTCTTCAATCTC

TCCCAAAGCCTAAAGCGATCTCTGCAAATCTCTCGCGACTCTCTCTTTCA

AGGTATATTTTCTGATTCTTTTTGTTTTTGATTCGTATCTGATCTCCAAT

TTTTGTTATGTGGATTATTGAATCTTTTGTATAAATTGCTTTTGACAATA

TTGTTCGTTTCGTCAATCCAGCTTCTAAATTTTGTCCTGATTACTAAGAT

ATCGATTCGTAGTGTTTACATCTGTGTAATTTCTTGCTTGATTGTGAAAT

TAGGATTTTCAAGGACGATCTATTCAATTTTTGTGTTTTCTTTGTTCGAT

TCTCTCTGTTTTAGGTTTCTTATGTTTAGATCCGTTTCTCTTTGGTGTTG

TTTTGATTTCTCTTACGGCTTTTGATTTGGTATATGTTCGCTGATTGGTT

TCTACTTGTTCTATTGTTTTATTTCAGGTCACCAAACA 6.1.2 CaMV 35S Promoter

The 35S promoter from Cauliflower mosaic virus (35S-PRO) was synthesised based on GenBank accession number AF502128

35S-PRO Sequence

SEQ ID NO. 50
TTAGCCTTTTCAATTTCAGAAAGAATGCTAACCCACAGATGGTTAGAG

AGGCTTACGCAGCAGGTCTCATCAAGACGATCTACCCGAGCAATAATC

TCCAGGAAATCAAATACCTTCCCAAGAAGGTTAAAGATGCAGTCAAAA

GATTCAGGACTAACTGCATCAAGAACACAGAGAAAGATATATTTCTCA

AGATCAGAAGTACTATTCCAGTATGGACGATTCAAGGCTTGCTTCACA

AACCAAGGCAAGTAATAGAGATTGGAGTCTCTAAAAAGGTAGTTCCCA

CTGAATCAAAGGCCATGGAGTCAAAGATTCAAATAGAGGACCTAACAG

AACTCGCCGTAAAGACTGGCGAACAGTTCATACAGAGTCTCTTACGAC

TCAATGACAAGAAGAAAATCTTCGTCAACATGGTGGAGCACGACACAC

TTGTCTACTCCAAAAATATCAAAGATACAGTCTCAGAAGACCAAAGGG

CAATTGAGACTTTTCAACAAAGGGTAATATCCGGAAACCTCCTCGGAT

TCCATTGCCCAGCTATCTGTCACTTTATTGTGAAGATAGTGGAAAAGG

AAGGTGGCTCCTACAAATGCCATCATTGCGATAAAGGAAAGGCCATCG

TTGAAGATGCCTCTGCCGACAGTGGTCCCAAAGATGGACCCCCACCCA

CGAGGAGCATCGTGGAAAAAGAAGACGTTCCAACCACGTCTTCAAAGC

AAGTGGATTGATGTGATATCTCCACTGACGTAAGGGATGACGCACAAT

CCCACTATCCTTCGCAAGACCCTTCCTCTATATAAGGAAGTTCATTTC

ATTTGGAGAGAACACGGGGGAC 6.1.3 TAF2 Promoter Sequence

The 5' untranslated region upstream of the TAF2 gene from *Arabidopsis thaliana* was synthesised based on sequence At1g73965 from the *Arabidopsis* genome, (www.arabidopsis.org).

SEQ ID NO. 51
GGTACCATGATCGCTTCATGTTTTTATCTAATTTGTTAGCATATTGAA

TGATTGATTTTCTTTTAATTTGGATATGTTGATTGTCTTGTTGCATCA

TCAATGTATGTTTTATTTAACACCGGAAGATCTTATGATGGGTTCATT

ACTTCATAATAATCTCCGAGTTCTACAAGACTACAACTTTCACGTGAC

TTTTACAGCGACAAAAAATGCATCTAGCGAAAATTAATCCACAACCTA

TGCATTTTTGTCACTCTTCACACGCGTATGTGCATAAATATATAGTAT

ATACTCGACAATCGATGCGTATGTGTACACAATTACCAAAACAATTAT

TTGAATATTCAGACATGGGTTGACATCACCAAGTAATATTCACAGTAT

CTGAAAACTATGTTTTGACATCCCTAAATAGTTTGACTAACCAGTTTA

ATATGAGAGCATTTGTAAGAGGCAAGAGCCATGGTTTTGTTGGCTCGT

TTAATATGCTCATTTAACCCCCCCAAAAAATACTATTAGATTTAAACG

TAAAAGAATTAACGAACACAAGAACTGCTAAAACAAAAAAAATCAAT

GGCCGACATTTCATAGTTCATACATCACTAATACTAAAAGATGCATCA

TTTCACTAGGGTCTCATGAAATAGGAGTTGACATTTTTTTTTGTAACG

ACAGAAGTTGACATGTTAAGCATCAATTTTTTTAAGAGTGGATTATAC

TAGTTTTTTTTTTTTTTTAATGTATGGTATGATACAACAACAAAAA

CTATAAAATAGAAAAGTCAGTGAAACCTCAAATTGAAGGAAAACTT

TTGCACAAAAAGAGAGAGAGAGAAAGAATGTAAATCCAAATAAATG

GGCCTAATTGAGAATGCTTTAACTTTTTTTTTTGGCTAAAAGAGAAT

GCTTTAACTAAGCCCATAAAATGAACATCAAACTCAAAGGGTAAGATT

AATACATTTAGAAAACAATAGCCGAATATTTAATAAGTTTAAGACATA

GAGGAGTTTTATGTAATTTAGGAACCGATCCATCGTTGGCTGTATAAA

AAGGTTACATCTCCGGCTAACATATCGGCAAAAAGGAACCTCGAG

6.3 Terminator Sequences
6.3.1 Nos Terminator

The nos terminator fragment was synthesised based on GenBank sequence accession EU048864.

nos Terminator Sequence

SEQ ID NO. 52

```
TCTAGAGTCAAGCAGATCGTTCAAACATTTGGCAATAAAGTTTCTTAA

GATTGAATCCTGTTGCCGGTCTTGCGATGATTATCATATAATTTCTGT

TGAATTACGTGAAGCATGTAATAATTAACATGTAATGCATGACGTTAT

TTATGAGATGGGTTTTTATGATTAGAGTCCCGCAATTATACATTTAAT

ACGCGATAGAAAACAAAATATAGCGCGCAAACTAGGATAAATTATCGC

GCGCGGTGTCATCTATGTTACTAGATCGACCTGCAG
```

6.3.2 Ags Terminator

The agropine synthase polyA signal (ags terminator) was synthesized based on the GenBank sequence EU181145.

ags Terminator Sequence

SEQ ID NO. 53

```
GAATTAACAGAGGTGGATGGACAGACCCGTTCTTACACCGGACTGGGC

GCGGGATAGGATATTCAGATTGGGATGGGATTGAGCTTAAAGCCGGCG

CTGAGACCATGCTCAAGGTAGGCAATGTCCTCAGCGTCGAGCCCGGCA

TCTATGTCGAGGGCATTGGTGGAGCGCGCTTCGGGGATACCGTGCTTG

TAACTGAGACCGGATATGAGGCCCTCACTCCGCTTGATCTTGGCAAAG

ATATTTGACGCATTTATTAGTATGTGTTAATTTTCATTTGCAGTGCAG

TATTTTCTATTCGATCTTTATGTAATTCGTTACAATTAATAAATATTC

AAATCAGATTATTGACTGTCATTTGTATCAAATCGTGTTTAATGGATA

TTTTTATTATAATATTGATGAT
```

Part 2—Plant Transformation Methods and Vector Maps

Transformation of plants was carried out using constructs based on the pGreen0029 and pSOUP binary vectors (GenBank accession numbers EU0490266, EU048864 and EU048870) (Hellens et al, 2000, Plant Mol. Biol. 42: 819-832). The pSOUP-0179 vector is carrying the T-DNA from the pGreen0179 (GenBank accession number EU048866) vector into the pSOUP vector (GenBank accession number EU048870)

1. Transformation of Tobacco Plants 1.1. Transformation of tobacco plants was performed as described by Horsch et al (1985) (Science 227: 1229-1231) using *Agrobacterium* strain AGL1.

Plant transformants were selected on regeneration medium supplemented with Kanamycin 300 mg/l and/or Hygromycin 30 mg/l.

1.2 Vectors for Transformation of Tobacco Mitochondria
1.2.1 General Vectors for Transgene Expression into Mitochondria Expression using a Heterologous Promoter The ATP6 promoter region from *Arabidopsis thaliana* mitochondria (AtmATP6-PRO) can be used to direct expression of transgenes in tobacco mitochondria.

The gene coding for GFP was cloned between AtmATP6-PRO and the ATP6 terminator sequence from tobacco (NtmATP6-TER). This transgene expression construct was cloned between NtmLFS1 and NtmRFS1 upstream of PCD to form the mitochondria transformation unit (MTU). The mLTRASi sequence was placed under the control of the AtUbi3 promoter and ags terminator and cloned into the pGreen0029 together with the mitochondria transformation unit to generate the M21 vector (FIG. 3).

The mitochondria targeted reverse transcriptase-RNase H mRTRHi-Ty1 was placed under the control of the TAF2 promoter and ags terminator and cloned into the pSOUP-0179 vector to generate the M28 vector (FIG. 3).

The M21 and M28 constructs were co-transformed in *Agrobacterium* strain AGL1 and used for *Nicotiana tabacum* transformation.

Transgenic lines were recovered on selection medium supplemented with 300 mg/l of Kanamycin and/or 30 mg/l of Hygromycin:

Expression by Translational Fusion with a Native Mitochondrial Gene

NtmLFS4 corresponds to the 5' end of the gene coding for ATP6 and can be used for translational fusion with any gene of interest, promoter activity is provided by the ATP6 promoter upstream of NtmLFS4 upon insertion in the tobacco mitochondrial genome and termination of transcription is achieved with the ATP6 terminator sequence within NtmRFS4. The gene coding for GFP was fused to NtmLFS4 and cloned together with NtmRFS4 and PBD into domain IV of the LtrBM intron to form the mitochondria transformation unit (MTU). The mLTRASi sequence was placed under the control of the AtUbi3 promoter and ags terminator and cloned into the pGreen0029 together with the mitochondria transformation unit to generate the M22 vector (FIG. 4).

The M22 and M28 constructs were co-transformed in *Agrobacterium* strain AGL1 and used for *Nicotiana tabacum* transformation.

Transgenic lines were recovered on selection medium supplemented with 300 mg/l of Kanamycin and/or 30 mg/l of Hygromycin.

1.2.2 Cytoplasmic-Male Sterility (CMS) Inducing Construct

The CMS-inducing tobacco mitochondria transformation unit containing NtmLFS3, PCFM, NtmLFS3 and primer binding domain (PBD) was inserted into domain IV of the LtrBM intron. The resulting DNA fragment was fused to the 35S promoter and nos terminator and introduced into the pGreen0029 binary vector. The mLTRASi sequence was placed under the control of the AtUbi3 promoter and ags terminator and cloned into the pGreen0029 together with the mitochondria transformation unit to generate the M24 vector (FIG. 5).

The M24 and M28 constructs were co-transformed in *Agrobacterium* strain AGL1 and used for *Nicotiana tabacum* transformation.

Transgenic lines were recovered on selection medium supplemented with 300 mg/l of Kanamycin and/or 30 mg/l of Hygromycin.

2. Transformation of *Arabidopsis Thaliana*

2.1. Transformation of *Arabidopsis* plants was performed as described by Clough & Bent (Clough & Bent (1998) Plant Journal 16:735-743). The *Agrobacterium tumefaciens* strain GV3101 (Koncz & Schell (1986)—Mol Gen Genet. 204: 383-396) was used for transformation. The resulting DNA fragment was fused to the 35S promoter and nos terminator and introduced into the pGreen0029 binary vector.

2.2 Vectors for Transformation of *Arabidopsis thaliana* Mitochondria

Cytoplasmic-Male Sterility (CMS) Inducing Construct

The CMS-inducing *arabidopsis* mitochondria transformation unit containing AtmLFS5, PCFM, AtmLFS5 and primer binding domain (PBD) was inserted into domain IV of the LtrBM intron. The resulting DNA fragment was fused to the 35S promoter and nos terminator and introduced into the pGreen0029 binary vector. The mLTRASi sequence was placed under the control of the AtUbi3 promoter and ags terminator and cloned into the pGreen0029 together with the mitochondria transformation unit to generate the M27 vector (FIG. 6).

The M27 and M28 constructs (FIG. 3) were co-transformed in *Agrobacterium* strain GV3101 and used for *Arabidopsis* (Col-0) transformation.

Transgenic lines were recovered on selection medium supplemented with 300 mg/l of Kanamycin and/or 30 mg/l of Hygromycin.

Part 3—Results

The transformation of *Nicotiana tabacum* and *arabidopsis* with our vectors containing transgene cassettes generated transgenic plants. In all cases we were able to detect insertion of the transgene cassette into the mitochondria genome using PCR amplification of junction regions.

Five independent transgenic lines were analysed for each construct. Molecular analyses including sequencing of insert junctions showed that there was correct insertion in the mitochondrial genome in 80% of transformed plants.

Furthermore, male sterile tobacco plants transformed with the CMS-inducing open reading frame PCF from petunia mitochondria were generated (FIG. 7).

EXPERIMENTAL SECTION 1B

Modifications of the mitochondria transformation method described in Experimental section 1A can be improved using PBD designed for reverse transcription in the cytoplasm or in mitochondria, and by re-positioning of the building blocks on the transformation cassette (FIG. 8).

A set of constructs was prepared for tobacco and rice transformation with LtrB intron (LtrB-MTS) as the MTS (FIG. 9-10). The positioning of the transgene cassette building blocks was designed as described in FIG. 8, A-B.

PBD-MIT was designed as described previously.
PBD-MIT

```
                                        SEQ ID NO. 41
TATCTCACATTCACCCAATTGTCATGGTACCTACTGTGCATTGGATAC

TTCTAAGGAAGTCCACACAAATCAAGAACCATTAGACGTTTCATCTAA

CCAAACAGAAGAATGTGAGAAGGCTTCCACTAAGGCTAACTCTCAACA

GACAAC
```

The primer binding domain of the tobacco tnt1 retrotransposon was used as the PBD-CYT, and was amplified from genomic DNA of tobacco cv Petit Gerard using the following primers:

```
AS912   gccgcggctttattaccgtgaatatta      SEQ ID NO. 54

AS913   cgcggccgctctgataagtgcaacctgatt   SEQ ID NO. 55
```

PDB-CYT

```
                                        SEQ ID NO. 56
CTTTATTACCGTGAATATTATTTTGGTAAGGGGTTTATTCCCAACAAC

TGGTATCAGAGCACAGGTTCTGCTCGTTCACTGAAATACTATTCACTG

TCGGTAGTACTATACTTGGTGAAAAATAAAAATGTCTGGAGTAAAGTA
```

```
CGAGGTAGCAAAATTCAATGGAGATAACGGTTTCTCAACATGGCAAAG

AAGGATGAGAGATCTGCTCATCCAACAAGGATTACACAAGGTTCTAGA

TGTTGATTCCAAAAAGCCTGATACCATGAAAGCTGAGGATTGGGCTGA

CTTGGATGAAAGAGCTGCTAGTGCAATCAGGTTGCACTTATCAGA
```

In the first case, PBD-MIT was fused to the 3' end of the LtrB intron (FIG. 8A, FIG. 9A for tobacco and FIG. 10A for rice). As the LtrA protein possesses both LtrB-MTS-binding feature and reverse transcription activity it can fulfil both functions of (i) transgene RNA translocation into mitochondria and (ii) reverse transcription of the RNA cassette using mitochondrial tRNA-Met as a primer.

In the second case, PBD-CYT was fused to MTU (FIG. 8B, FIG. 9B for tobacco and FIG. 10B for rice), so that reverse transcription of the transgene cassette is initiated and performed by endogenous reverse transcriptases in the cytoplasm using cytoplasmic tRNA-Met. The LtrA protein serves as the MTS-binding protein for translocation of RNA:DNA complexes initiated by cytoplasmic reverse transcriptases, into the mitochondria.

Rice PCF Construct M45

Primers used to amplify the rice mitochondria left flanking sequence (osLFS) for insertion of the PCF open reading frame:

```
IM416   ggatccatatcgagccattgaagcag    SEQ ID NO. 57

IM417_gcatgctcaatcttgtcctttgg        SEQ ID NO. 58
``` osLFS

```
                                        SEQ ID NO. 59
ggattcatatcgagccattgaagcagcgcgtcgggctacaatcgggca attccatcgtgctatgagcggacaattccgaagaaattgtaagatatg ggtaagagttctcgcagatcttcctattacggggaaacccgcagaagt tcgaatgggaagaggaaaaggaaatcctacgggttggattgctcgtgt gtccacgggacaaatcccatttgaaatggatggtgtgagtttgtcaaa tgctcgacaagccgctagattagcggcgcataaccatgttcgtcaac caagtttgttcagtggtcgtaacgtaattggttagtggggaaaaaccg ggccgggactcaaaagaatttggcgaagtgtttgttcctgaacgaggg aagtggaaagacaaagagggataggagctcgcctccttcttttttg aatcgccgaaattgtacgacgaccttcttgttccaggcatacgactc tgagacgtgacggtgtcacttttccggccoggtaaagtgacagttata taaataagaataagaaagagaagcgtgatgttgtcagcaatcaaatta tcgtaaatagatagtacggttgcgttgtttcaatttctgttcgtcggt ccttgggttacgaaggtgtgggcttactaatacggagagggttccgaa tgataaagtgtcatgaaagttcgtgaaagaatgttcttgtttttcgtt ggaaaacccaacgccacggccacaaaacgaaaaagtctcccgtttgtt ttgggagcagagctttaaaaggatatagttaccctatgatgagattta
```

```
-continued
gttcaacggataagaaggatagaagaaatatgctatttgctgctattc catctatttgtgcattcagtgctgccgttccccggccccaaaggaca agattgagcatgc
```

Primers used to Amplify the Rice Mitochondria Left Flanking Sequence (osRFS) for Insertion of the PCF Open Reading Frame:

```
IM418   ttctagagtcgccgctatcacttt    SEQ ID NO. 60

IM419   ccgcggctaagactatagaatgttcc  SEQ ID NO. 61
``` osRFS

```
                                    SEQ ID NO. 62
ttctagagtcgccgctatcacttttttggggggccaatcccgcgaag agttatggaaagattttatagctcaattgaatgaagaaagtgaattca tggacaacattttttttggtgtttacaacgcgagaaacggctatgaaa gcgccacagttcttcagggaatacggatagatttagcgataaacggct atgaaagtgcattttttgtcggaatttgcacctatttgtatctatttag tgatcagtccgctagtttctttgattccactcggtgttccttttccat ttgcttccaatagttcgacctatccagaaaaattgtcggcctacgaat gtggtttcgatccctccggtgatgccagaagtcgtttcgatatacgat tttatccggttcctattttatttattatccctgatctggaagtcacct ttttttttccttgggcagtacctcctaacaagattgatctgtttggat cttggtccatgatggcctttttattgattttgacgattggatttctct atgaatggaaaaggggtgcttcggatcgggagtaaccactagtgaaag ggcaaaggggggaaggacataggaagagggatgcctacaaaaaatca attgattcgtcatggtagagaagaaaaacagcgcacggaccgtactcg agcttcggatcaatgtccccaaaagcaaggagtatgcctgcgtgtttc gacgagaacaccgaaaaaacctaattcagctctacgtaagatagcaaa agtacggttgagcaatcgacatgatatatttgctcacattccaggcga aggtcataattcgcaggaacattctatagtcttagccgcggcc
```

The LtrA gene was driven by the actin1 rice promoter amplified using the following primers:

```
ARP1  gtcattcatatgcttgagaaga   SEQ ID NO. 63

ARP2  gcctacaaaaaagctccgcacg   SEQ ID NO. 64
```

Rice act1 Promoter Sequence

```
                                    SEQ ID NO. 65
gtcattcatatgcttgagaagagagtcgggatagtccaaaataaaaca aaggtaagattacctggtcaaaagtgaaaacatcagttaaaaggtggt ataagtaaaatatcggtaataaaaggtggcccaaagtgaaatttactc ttttctactattataaaaattgaggatgttttgtcggtactttgatac gtcattttgtatgaattggttttttaagtttattcgcgatttggaaat gcatatctgtatttgagtcggttttttaagttcgttgcttttgtaaata cagagggatttgtataagaaatatctttaaaaaacccatatgctaatt tgacataatttttgagaaaaatatatattcaggcgaattccacaatga acaataataagattaaaatagcttgcccccgttgcagcgatgggtatt ttttctagtaaaataaaagataaacttagactcaaaacatttacaaaa acaaccccctaaagtcctaaagcccaaagtgctatgcacgatccatagc aagcccagcccaacccaacccaacccaacccaccccagtgcagccaac tggcaaatagtctccacccccggcactatcaccgtgagttgtccgcac caccgcacgtctcgcagccaaaaaaaaaaaagaaagaaaaaaaagaa aaagaaaaacagcaggtgggtccgggtcgtgggggccggaaaagcgag gaggatcgcgagcagcgacgaggcccggccctccctccgcttccaaag aaacgcccccatcgccactatatacatacccccccctctcctcccat cccccaaccctaccaccaccaccaccaccaccacctcctcccccctcgct gccggacgacgagctcctcccccctcccctccgccgccgccggtaac caccccgcccctctcctctttctttctccgtttttttttttcgtctogg tctcgatctttggccttggtagtttgggtgggcgagagcggcttcgtc gcccagatcggtgcgcgggaggggcgggatctcgcggctggcgtctcc gggcgtgagtcggccoggatcctcgcggggaatgggctctoggatgt agatctgcgatccgccgttgttgggggagatgatgggggggtttaaaat ttccgccatgctaaacaagatcaggaagaggggaaaagggcactatgg tttatatttttatatatttctgctgcttcgtcaggcttagatgtgcta gatcttctttctttcttcttttttgtggtagaatttgaatccctcagca ttgttcatcggtagttttttcttttcatgatttgtgacaaatgcagcct cgtgcggagcttttttgtaggc
```

Transformation of Rice Immature Embryos.
Immature Embryo Excision
Day 1:
Remove milky/post-milky stage immature seeds from panicles (immature embryos 1-2 mm in size are desired).
Sterilize immature seeds: 50% sodium hypochlorite (12%)+1 drop of tween 20. Shake 10 min.
Rinse 3-5× in sterile deionised water. Drain off surplus water. Aliquot seeds (around 40) in sterile Petri dishes.
Set up a 60×15 mm Petri dish containing a 50% sodium hypochlorite solution and next to this a sterile beaker on its side with a sterile filter paper in it. Use sterile forceps to aseptically remove glumes from the first seed. Immerse this seed in the 50% sodium hypochlorite. Remove glumes from a second seed and immerse the second seed into the sodium hypochlorite solution whilst removing the first seed and storing this dehusked/sterilized seed on the filter paper in the beaker. Continue.
After all the glumes are removed:
Sterilize dehusked seeds: 50% sodium hypochlorite: 5 min. with agitation.
Rinse: 5-7× in sterile deionized water, drain.
Place all seeds in a large sterile Petri dish. Aliquot for embryo excision (to keep seeds from drying out, work with only 50-100 in the plate at a time leaving the rest in the master plate).
Remove the embryo from each seed and place embryo, scutellum up, in a 90×15 mm Petri dish containing proliferation medium (40-50 embryos/plate). Culture at 28° C. in the dark for 2 days prior to bombardment Day 3:

Check each Embryo for Contamination before Blasting

Remove the embryos from the proliferation medium. Distribute 35-40 embryos scutellum upwards in an area 1 cm² in the centre of a 60×15 mm target plate containing 10 ml of proliferation medium+osmoticum (0.6 M). Check each target plate so that the scutellum is straight. Allow enough room so the scutella do not shade each other out.

Bombardment:

| Gun | 14 kV |
| --- | --- |
| | Vacuum: 25 inches of Hg |
| 1$^{st}$ bombardment | 4 hours after osmoticum treatment |
| 2$^{nd}$ bombardment | 4 hours after 1$^{st}$ bombardment |

Day 4:

4-16 hours after the 2nd blast transfer immature embryos to proliferation medium without osmoticum. Culture in the dark at 28° C. for 2 days.

Selection:

Day 5:

Aseptically cut out with scissors the germinating shoot. Transfer 16-20 immature embryos to fresh proliferation medium containing 30-50 mg/l Hygromycin (depending on the genotype); culture in the dark at 28° C.; record total number of embryos.

After 10 days carefully remove the callus from the scutellum by breaking it up into 2-10 small pieces; subculture onto fresh proliferation medium+hygromycin. Do not subculture brown tissue and remaining immature embryo which could inhibit further growth of healthy callus.

Subculture every 10 days by selecting healthy tissue: (embryogenic if present) and transfer it to fresh proliferation medium+hygromycin. Remove brown callus as it could be inhibiting to Embryogenic callus.

30 to 40 days after bombardment change selection procedure. Instead of eliminating bad-looking tissue keep embryogenic tissue only (eliminate healthy non-embryogenic tissue)

Regeneration:

After 40 to 60 days, transfer established embryogenic callus showing differential growth on proliferation medium+ hygromycin to regeneration medium+hygromycin. Culture at 28° C. under low light for 10 days then under high light for 10 additional days. Check plates periodically in the light for the development of embryos and green shoots. As shoots develop it is sometimes beneficial to gently move the developing shoot away from the callus it originated from and remove any dead tissue from the shoot itself to prevent inhibition of growth.

Germination:

Transfer white compact embryos and green shoots initiating roots to the germination medium under high light at 28° C. for 1 to 2 weeks. Check plates periodically. Remove necrotic tissue and divide germinating embryos if necessary.

Results

The transformation of *Nicotiana tabacum* and rice was performed with group II intron-based vectors containing transgene cassettes for transformation of the mitochondrial genome.

Seven to ten independent transgenic lines were analysed for each construct. Molecular analyses including sequencing of insert junctions showed that there was correct insertion in the mitochondrial genome in 80% of transformed plants. Insertion of the PCF open reading frame in the plant mitochondria was correlated with a sterility phenotype.

The analysis of transgenic plants was performed using PCR for insertion flanking sequences using the following pairs, of primers:

For Tobacco:

| ntLFS3F | cccaagttacagcgggctct | SEQ ID NO. 66 |
| PCFMR | tatggggcttccctgtcgag | SEQ ID NO. 67 |
| PCFMF | gcagcaccaaaattgagcct | SEQ ID NO. 68 |
| ntRFS3R | cgagttccagaggcatcttc | SEQ ID NO. 69 |

For Rice:

| osLFSF | actgaatgcggaaagtatgg | SEQ ID NO. 70 |
| PCFMR | tatggggcttccctgtcgag | SEQ ID NO. 71 |
| PCFMF | gcagcaccaaaattgagcct | SEQ ID NO. 72 |
| osRFSR | tagggctactagaaagagga | SEQ ID NO. 73 |

The invention claimed is:

1. A method of transforming a plant cell, the method comprising:
   1) introducing into the plant cell a first nucleic acid sequence that comprises a plant nuclear promoter operably linked to a first nucleic acid sequence that comprises a plant mitochondrion transgene cassette, a plant mitochondrion translocation sequence from a group II intron RNA, wherein the group II intron is Ll.LtrB, and a primer binding domain; and
   2) introducing into the plant cell a second nucleic acid sequence that encodes for a translocation sequence binding protein from an intron encoded protein (IEP) of a group II intron,
   wherein the IEP is LtrA fused to a plant mitochondrion transit peptide,
   wherein the second nucleic acid sequence is operably linked to a plant nuclear promoter, and
   wherein the mitochondrion translocation sequence of the product of 1) binds with the translocation sequence binding protein of the product of 2).

2. The method according to claim 1, wherein the plant mitochondrion transgene cassette comprises:
   i) a left flanking sequence (LFS) having least one mitochondrion specific promoter (mPRO) and a right flanking sequence (RFS) having at least one mitochondrion specific terminator (mTER) sequence; and
   ii) at least one isolated nucleic acid of interest.

3. The method according to claim 1, wherein the said isolated nucleic acid sequence is a recombinant DNA sequence or an introduced native, isolated genomic DNA sequence selected from isolated mammalian or plant nucleic acid sequences.

4. The method according to claim 3, wherein the isolated nucleic acid sequence is selected from nucleic acid sequences encoding proteins that confer cytoplasmic male sterility to a plant.

5. The method according to claim 1, wherein the primer binding domain is selected from that of a retrotransposon, or of a retrovirus.

6. A method of producing at least a heterologous or exogenous RNA species in a plant that comprises:
   1) introducing into a regenerable plant cell a nucleic acid sequence that comprises a plant nuclear promoter operably linked to a first nucleic acid sequence that comprises a plant mitochondrion transgene cassette, a plant mitochondrion translocation sequence from a group II intron RNA, wherein the group II intron is Ll.LtrB, and a primer binding domain;
   2) introducing into the regenerable plant cell a second nucleic acid sequence that encodes for a translocation sequence binding protein from an intron encoded protein (IEP) of a group II intron, wherein the IEP is LtrA fused to a plant mitochondrion transit peptide, and wherein said second nucleic acid sequence is operably linked to a plant nuclear promoter;
   3) growing the regenerable plant cell of steps 1) to 2);
   4) selecting a plant cell of 3), wherein the transgene comprised within the plant mitochondrion transgene cassette is integrated into the mitochondrial genome;
   5) regenerating a plant from the plant cell of 4); and
   6) growing the plant of 5).

7. The method according to claim 6, wherein the heterologous or exogenous RNA species encoded by the transgene that is integrated into the mitochondrion is expressed as a heterologous or exogenous protein.

8. An isolated polynucleotide sequence that comprises a plant nuclear promoter operably linked to a first nucleic acid sequence that comprises a plant mitochondrion transgene cassette, a plant mitochondrion translocation sequence from a group II intron RNA, wherein the group II intron is Ll.LtrB, and a primer binding domain for use in a method according to claim 1.

9. An isolated polynucleotide sequence that encodes for a mitochondrion translocation sequence-binding protein fused to a plant mitochondrion transit peptide wherein the polynucleotide sequence is operably linked to a plant nuclear promoter for use in a method according to claim 1.

10. An isolated polynucleotide sequence that encodes for a mitochondrion translocation sequence-binding protein from an intron encoded protein (IEP) of a group II intron, wherein the IEP is LtrA fused to a plant mitochondrion transit peptide, and wherein the polynucleotide sequence is operably linked to a plant nuclear promoter for use in a method according to claim 6.

11. An isolated polynucleotide sequence that encodes for a reverse transcriptase protein fused to a plant mitochondrion transit peptide, wherein the polynucleotide sequence is operably linked to a plant nuclear promoter for use in a method according to claim 1.

12. An isolated polynucleotide sequence that encodes for a reverse transcriptase protein fused to a plant mitochondrion transit peptide wherein the polynucleotide sequence is operably linked to a plant nuclear promoter for use in a method according to claim 6.

13. The isolated polynucleotide sequence according to claim 8 comprising genomic DNA or cDNA.

14. A cell containing a heterologous polynucleotide according to claim 8 comprised in a plant, a plant part, or a plant propagule, or in plant cell culture wherein the plant is selected from the group consisting of tobacco (*Nicotiana tabacum*) and other *Nicotiana* species, carrot, vegetable and oilseed Brassicas, melons, capsicums, grape vines, lettuce, strawberry, sugar beet, wheat, barley, corn (maize), rice, peas, sorghum, sunflower, tomato, cotton, and potato.

15. The method according to claim 3, wherein the isolated nucleic acid sequence is selected from nucleic acid sequences encoding proteins selected from the petunia mitochondrion pcf sequence, the orf107 sequence of sorghum and the orf79 of rice.

16. The method according to claim 1, wherein the primer binding domain is selected from the yeast Ty1 retrotransposon and the TnT1 tobacco retrotransposon.

17. The method according to claim 1, wherein the MTS sequence is selected from the group II intron-derived MTS from the *Lactococcus lactis* Ll.LtrB intron.

* * * * *

SEQUENCE LISTING

```
<160> NUMBER OF SEQ ID NOS: 73

<210> SEQ ID NO 1
<211> LENGTH: 980
<212> TYPE: DNA
<213> ORGANISM: Artificial Sequence
<220> FEATURE:
<223> OTHER INFORMATION: Synthetic sequence: LtrBM intron sequence

<400> SEQUENCE: 1
ggatccctcg aggtgcgccc agatagggtg ttaagtcaag tagtttaagg tactactcag      60
taagataaca ctgaaaacag ccaacctaac cgaaaagcga aagctgatac gggaacagag     120
cacggttgga aagcgatgag ttagctaaag acaatcggct acgactgagt cgcaatgtta     180
atcagatata agctataagt tgtgtttact gaacgcaagt ttctaatttc ggttatgtgt     240
cgatagagga aagtgtctga aacctctagt acaaagaaag ctaagttatg gttgtggact     300
```

```
tagctgttat caccacattt gtacaatctg ttggagaacc aatgggaacg aaacgaaagc    360
gatggcgaga atctgaattt accaagactt aacactaact ggggatagcc taaacaagaa    420
tgcctaatag aaaggaggaa aaaggctata gcactagagc ttgaaaatct tgcaaggcta    480
cggagtagtc gtagtagtct gagaaggcta acggccttta catggcaaag ggctacagtt    540
attgtgtact aaaattaaaa attgattagg gaggaaaacc tcaaaatgaa accaacaatg    600
gcaattttag aaagaatcag taaaaattca caagaaaata tagacgaagt ttttacaaga    660
ctttatcgtt atcttttacg tcctgatatt tattacgtgg cgggcgcgcc acgcgtgcgg    720
ccgctgggaa atggcaatga tagcgaaaga acctaaaact ctggttctat gctttcattg    780
tcatcgtcac gtgattcata aacacaagtg aattttttacg aacgaacaat aacagagccg    840
tatactccga gaggggtacg tacggttccc gaagagggtg gtgcaaacca gtcacagtaa    900
tgtgaacaag gcggtaccct cctacttcac catatcattt ttaattctac gaatctttat    960
actggcaaac aatttgactg                                                980

<210> SEQ ID NO 2
<211> LENGTH: 32
<212> TYPE: DNA
<213> ORGANISM: Artificial Sequence
<220> FEATURE:
<223> OTHER INFORMATION: Synthetic sequence: NtmLFS1 primer IM101

<400> SEQUENCE: 2
gcgggcgcgc ctattactct cggtccttgt tc                                   32

<210> SEQ ID NO 3
<211> LENGTH: 36
<212> TYPE: DNA
<213> ORGANISM: Artificial Sequence
<220> FEATURE:
<223> OTHER INFORMATION: Synthetic sequence: NtmLFS1 primer IM102

<400> SEQUENCE: 3
gcggagctct acccttttaag actcaattac atcgag                              36

<210> SEQ ID NO 4
<211> LENGTH: 35
<212> TYPE: DNA
<213> ORGANISM: Artificial Sequence
<220> FEATURE:
<223> OTHER INFORMATION: Synthetic sequence: NtmRFS1 primer IM103

<400> SEQUENCE: 4
gcatgcattg cataagtaat ctcttttctt atgag                                35

<210> SEQ ID NO 5
<211> LENGTH: 28
<212> TYPE: DNA
<213> ORGANISM: Artificial Sequence
<220> FEATURE:
<223> OTHER INFORMATION: Synthetic sequence: NtmRFS1 primer IM104

<400> SEQUENCE: 5
actagtaagg ggatttgcca catcgttg                                        28

<210> SEQ ID NO 6
<211> LENGTH: 601
<212> TYPE: DNA
<213> ORGANISM: Nicotiana tabacum
```

<400> SEQUENCE: 6

```
tattactctc ggtccttgtt cttggtctct gtgaaagatc cagtcgatgg gaatgaatcc      60
atgttcaaat cttattaccg ggttcgatta cgggaaggaa atagagaagg taagggaccg     120
ctttccttgt tcaagccggt attgtttgag taagtagtaa gtaagtgaga agtggtgaat     180
tggccaggag gaataaagct tatttcaagt actaataaaa gcattcatta caaactcttg     240
tgctcactta tcccaagtat aggatgtttt ccctgagcct gtctgtgttg aatacgcttt     300
ttccgtgtag aatagagatt ctctctaagg ttgatagaat atacgttttc tttctctgat     360
taaaggttgt ccaaagagga ctaagagaca gatgctgtgc ttgcaagtaa gcttcagcca     420
agcatcagat aaaccaagtt cgggttggga aagggctat ttaccccagc aatatagaat      480
aattattacc cccagcacat ccccaaatga gagcatcgtc tttacccta gaaaaggtgc      540
gatgtaattt cctggttcga ttacattgct cgatgtaatt gagtcttaaa gggtagagct    600
c                                                                     601
```

<210> SEQ ID NO 7
<211> LENGTH: 606
<212> TYPE: DNA
<213> ORGANISM: Nicotiana tabacum

<400> SEQUENCE: 7

```
attgcataag taatctcctt tcttatgaga actacgaatc atcctcatga ataagctcta     60
ctctacctta aggagatgtg gaggcaatag gtcccgtgca gctttaacta actctactcc   120
tccatacgcc tatcctttag tttagtgggc caggtcctcc agccttccat tagctttcga   180
tttagtttgc attcaaagtc ttggaatgcg agcttatgtg ctttcaggta taggcaccat   240
tcgcctgact tcttgaagt cctaggattc tcccctagta ttccattctc tcccctctc     300
ggccttgctt tcattcctgt ctcatttgaa attgctccta aggcagggag tcttctcgaa   360
gctgtctaag tcttgtaagg ctcctatatc tatatataga gaggtcatgg tatggaggga   420
ggatttctac gcgcaacatc gtggttgggg cattcctcct tcttttaaaa gaagactaga   480
ggacgaaaga agaagctctt acatcggata aagcctaatt ccactgtcct ttgaagattg   540
gaagatagtg aaggccgact tcctttttaa agatcactca acgatgtggc aaatccctt    600
actagt                                                               606
```

<210> SEQ ID NO 8
<211> LENGTH: 29
<212> TYPE: DNA
<213> ORGANISM: Artificial Sequence
<220> FEATURE:
<223> OTHER INFORMATION: Synthetic sequence: NtmLFS3 primer IM263

<400> SEQUENCE: 8

```
ggcgcgccag cagatttcct ccctctatc                                       29
```

<210> SEQ ID NO 9
<211> LENGTH: 29
<212> TYPE: DNA
<213> ORGANISM: Artificial Sequence
<220> FEATURE:
<223> OTHER INFORMATION: Synthetic sequence: NtmLFS3 primer IM264

<400> SEQUENCE: 9

```
gcatgcagat cgacgacgga acgaagaac                                       29
```

```
<210> SEQ ID NO 10
<211> LENGTH: 26
<212> TYPE: DNA
<213> ORGANISM: Artificial Sequence
<220> FEATURE:
<223> OTHER INFORMATION: Synthetic sequence: NtmRFS3 primer IM265

<400> SEQUENCE: 10
tctagatcca atttcttccg gtatgc                                              26

<210> SEQ ID NO 11
<211> LENGTH: 24
<212> TYPE: DNA
<213> ORGANISM: Artificial Sequence
<220> FEATURE:
<223> OTHER INFORMATION: Synthetic sequence: NtmRFS3 primer IM375

<400> SEQUENCE: 11
ccgcggtacg gtccgtgcgc cgtt                                                24

<210> SEQ ID NO 12
<211> LENGTH: 436
<212> TYPE: DNA
<213> ORGANISM: Nicotiana tabacum

<400> SEQUENCE: 12
agcagatttc ctccctctat caactccttt tttatggtcg ggaggatcca caattcttca         60
ttgatccaca agacctggat tccatactga gggtgcacct tgaacccttta gaattcaatc       120
accctgctct atgccaggtc ttagaaagtc tatgtgtcga aagcatgat tccccttttt         180
atcaagatgt aaaaatggct caagcgcatc attttcgtgg ctttataaac ttaaagcacc        240
aagcgaaatt ggaaatgcaa catcgcctag agttaggaga ggtatggaaa tctcttgaga        300
gaaggaacgc ttttctaagc caggaaaacg cctctctaag agaaaaactt ttaattctcg        360
acagggaagc cccatagaaa ttcttctttg ttgtgttgct atcctaaaat tgcgttcttc        420
gttccgtcgt cgatct                                                       436

<210> SEQ ID NO 13
<211> LENGTH: 535
<212> TYPE: DNA
<213> ORGANISM: Nicotiana tabacum

<400> SEQUENCE: 13
tctagatcca atttcttccg gtatgccgct ccgccagcaa ggagcgaaag aaccaagttt         60
tctgtggtga tgtcagaatt tgcacctatt tgtatctatt tagtgatcag tccgctagtt       120
tctttgctcc cactcggtct tccttttcta ttttcttcca attcttcgac ctatccagaa       180
aaattgtcgg cctacgaatg tggtttcgat ccttccggtg atgccagaag tcgttttgat        240
ataagatttt atcttgtttc cattttattt attattcctg atccggaagt aaccttttcc        300
tttccttggg cagtacctcc caacaagatt gatccgtttg gatcttggtc catgatggcc        360
tttttattga ttttgacgat tggatctctc tatgaatgga aaggggtgc ttcggatcgg        420
gagtaaccac tagtgagagg gcaaaaattg gggggaagga caaggaaag agcgatgcct         480
acattaaatc aattgattcg tcatggtaga gaagaaaaac ggcgcacgga ccgta            535

<210> SEQ ID NO 14
<211> LENGTH: 29
<212> TYPE: DNA
<213> ORGANISM: Artificial Sequence
<220> FEATURE:
```

<223> OTHER INFORMATION: Synthetic sequence: NtmLFS4 primer IM376

<400> SEQUENCE: 14
ggcgcgccag ggtatgatac cttatagct                29

<210> SEQ ID NO 15
<211> LENGTH: 24
<212> TYPE: DNA
<213> ORGANISM: Artificial Sequence
<220> FEATURE:
<223> OTHER INFORMATION: Synthetic sequence: NtmLFS4 primer IM287

<400> SEQUENCE: 15
ctcgagtgag actcgctttt gttc                24

<210> SEQ ID NO 16
<211> LENGTH: 26
<212> TYPE: DNA
<213> ORGANISM: Artificial Sequence
<220> FEATURE:
<223> OTHER INFORMATION: Synthetic sequence: NtmRFS4 primer IM289

<400> SEQUENCE: 16
gagctcatgg gtatacttag tcgtgg                26

<210> SEQ ID NO 17
<211> LENGTH: 29
<212> TYPE: DNA
<213> ORGANISM: Artificial Sequence
<220> FEATURE:
<223> OTHER INFORMATION: Synthetic sequence: NtmRFS4 primer IM377

<400> SEQUENCE: 17
ccgcggctga gatagctccg taaactaat                29

<210> SEQ ID NO 18
<211> LENGTH: 490
<212> TYPE: DNA
<213> ORGANISM: Nicotiana tabacum

<400> SEQUENCE: 18
ccagggtatg ataccttata gcttcacagt tacaagtcat tttctcatta ctttgggtct    60
ctcattttct attttttattg gcattactat agtgggattt caaaaaaatg ggcttcattt   120
tttaagcttc ttattacctg caggagtccc actgccatta gcacctttt  tagtactcct   180
tgagctaatc ccttattgtt ttcgagcatt aagctcagga atacgtttat ttgctaaatat   240
gatggccggt catagttcag taaagatttt aagtgggttc gcttggacta tgctatgtat   300
gaatgatctt ttatatttca taggggatct tggtcctta tttatagttc ttgcattaac    360
cggtctggaa ttaggtgtag ctatatcaca agctcatgtt tctacgatct taatctgtat   420
ttacttgaat gatgctataa atcttcatca aagtgcttct tttttataa ttgaacaaaa    480
gcgagtctca                                                          490

<210> SEQ ID NO 19
<211> LENGTH: 478
<212> TYPE: DNA
<213> ORGANISM: Nicotiana tabacum

<400> SEQUENCE: 19
atgggtatac ttagtcgtgg agcattccga gtatttgctt tagggatcgt tcctgcgcat    60
ctccttactt tatagcagtt attgctccgg ttccagaagg tatagctctc gcctcagctt   120

```
tttctttgaa atcggagact gttccaattt cctactgaga taggcaagcg gagggagaac    180
tagacgtatc ttgctaggca aagacaggtt agaatggata gctcgcgggt gggattgacg    240
ggatagatca ctattgcaga aggaggtaga accgggggaa gaattatggc tataaaggtc    300
ctcgccctct taggcacatg gttctaaaga ttaaatctca aagcggtact aaagattagg    360
cagaagaaga actagaacta gaattcttcg cccctcccct tgtaccaaga agcaagttca    420
gaacataagg ataatgggct cgtctattat aagttattag tttacggagc tatctcag     478
```

<210> SEQ ID NO 20
<211> LENGTH: 30
<212> TYPE: DNA
<213> ORGANISM: Artificial Sequence
<220> FEATURE:
<223> OTHER INFORMATION: Synthetic sequence: AtmLFS5 primer IM398

<400> SEQUENCE: 20

```
ggcgcgccgg gaggaagctg ggccagtagt                                      30
```

<210> SEQ ID NO 21
<211> LENGTH: 35
<212> TYPE: DNA
<213> ORGANISM: Artificial Sequence
<220> FEATURE:
<223> OTHER INFORMATION: Synthetic sequence: AtmLFS5 primer IM399

<400> SEQUENCE: 21

```
gcatgcgaaa aataaagaaa gaagcaaaag cccat                                35
```

<210> SEQ ID NO 22
<211> LENGTH: 23
<212> TYPE: DNA
<213> ORGANISM: Artificial Sequence
<220> FEATURE:
<223> OTHER INFORMATION: Synthetic sequence: AtmRFS5 primer IM400

<400> SEQUENCE: 22

```
atcgatatgc cgcttcttcg cca                                             23
```

<210> SEQ ID NO 23
<211> LENGTH: 28
<212> TYPE: DNA
<213> ORGANISM: Artificial Sequence
<220> FEATURE:
<223> OTHER INFORMATION: Synthetic sequence: AtmRFS5 primer IM401

<400> SEQUENCE: 23

```
ccgcggattt tgtgccctat cactttac                                        28
```

<210> SEQ ID NO 24
<211> LENGTH: 453
<212> TYPE: DNA
<213> ORGANISM: Arabidopsis thaliana

<400> SEQUENCE: 24

```
gggaggaagc tgggccagta gtcccctatc catacaggag ggatgaaatg attgggggg     60 atagcgtaga ggcgatagaa cgccgccttc tggcgaaata ccccgaaggc tctccctctg   120
cggagatcat agagatggcc cgaatagagg ccgaagatct attcgagatc aaagcccaaa   180
tcatccaacg gatggctcta tatgacccaa ccggcgattg gatggcgcgt ggggctcggg   240
ccctcgataa tccgaggacc actagtgggg aagagtcctt ggagcgtctt tatgatatat   300
```

```
ggaaggacct ccaagaaacc gggcccctct cggacgagtt ttctcgttta caagagaaag    360
tattcctcaa gaaaggcggc cctgggggga accctatcgc ataaggtctg caagcctttc    420
gggatgggct tttgcttctt tctttatttt tcg                                 453

<210> SEQ ID NO 25
<211> LENGTH: 427
<212> TYPE: DNA
<213> ORGANISM: Arabidopsis thaliana

<400> SEQUENCE: 25
atatgccgct tcttcgccag caaggagcga gaaaacaaag tgggctgtaa tgatgtcaga     60
atttgcacca atttctatct atttagtgat tagtctgcta gtttctttga tcctactcgg    120
tgttcctttt ccatttgctt ccaatagttc tacctaccca gaaaaattgt cggcctacga    180
atgtggtttc gatccttccg gtgatgccag aagtcgtttc gatatacgat tttatcttgt    240
ttcaatttta tttttaatcc ctgatctgga agtaaccttt ttctttcctt gggcagtacc    300
tcccaacaag attgatctgt ttggattttg gtccatgatg gccttttat ttattttgac     360 gattggattt ctatatgaat ggaaaagggg tgcttcggat cgggagtaaa gtgatagggc    420
acaaaat                                                              427

<210> SEQ ID NO 26
<211> LENGTH: 29
<212> TYPE: DNA
<213> ORGANISM: Artificial Sequence
<220> FEATURE:
<223> OTHER INFORMATION: Synthetic sequence: NtATP6-PRO primer IM364

<400> SEQUENCE: 26
ggcgcgcctc tagtcgaata gagtattag                                       29

<210> SEQ ID NO 27
<211> LENGTH: 31
<212> TYPE: DNA
<213> ORGANISM: Artificial Sequence
<220> FEATURE:
<223> OTHER INFORMATION: Synthetic sequence: NtATP6-PRO primer IM365

<400> SEQUENCE: 27
atctcgagtg tgattgagat aaaaagattc c                                    31

<210> SEQ ID NO 28
<211> LENGTH: 30
<212> TYPE: DNA
<213> ORGANISM: Artificial Sequence
<220> FEATURE:
<223> OTHER INFORMATION: Synthetic sequence: AtATP6-PRO primer IM346

<400> SEQUENCE: 28
ctgcatgctc ctctactgag tcagtgacag                                      30

<210> SEQ ID NO 29
<211> LENGTH: 35
<212> TYPE: DNA
<213> ORGANISM: Artificial Sequence
<220> FEATURE:
<223> OTHER INFORMATION: Synthetic sequence: AtATP6-PRO primer IM347

<400> SEQUENCE: 29
attctagaat tggattaatt gatttcaaca aaatg                                35
```

<210> SEQ ID NO 30
<211> LENGTH: 361
<212> TYPE: DNA
<213> ORGANISM: Nicotiana tabacum

<400> SEQUENCE: 30

```
cctctagtcg aatagagtat tagtccgctc cattatattc cccattattt cactttctcg      60
ctattcgaaa tatcataaga gaagaaagct ggcaggttgg atcctagggt agattcctgc     120
tgttgaatga tcgactagct tcctctttag ttctttgata ttgggttcgt gttcagtgta     180
ccgctctttt tatatatgaa attacttcgt ccttttttt  agcccttttt cgtttgtcca     240
tcttttttc  tcccatgctt tccgttggtc aacaaccaac caaagtgctc tatacttctt     300
cactactcgt acaggcttga cggagttaag ctgtattgag ggaatctttt tatctcaatc     360
a                                                                    361
```

<210> SEQ ID NO 31
<211> LENGTH: 249
<212> TYPE: DNA
<213> ORGANISM: Arabidopsis thaliana

<400> SEQUENCE: 31

```
tcctctactg agtcagtgac agaagtgcag cagccaataa tacgtatata agaagaggac      60
tgcttacggg atcaaactat caatctcata agagaagaaa tctctatgcc ccctttttct     120
tggttttctc ccatgctttt gttggtcaac aaccaaccac aactttctat agttcttcac     180
tactcctaga ggcttgacgg agtgaagctg tctggaggga atcattttgt tgaaatcaat     240
taatccaat                                                            249
```

<210> SEQ ID NO 32
<211> LENGTH: 26
<212> TYPE: DNA
<213> ORGANISM: Artificial Sequence
<220> FEATURE:
<223> OTHER INFORMATION: Synthetic sequence: NtATP6-TER primer IM289

<400> SEQUENCE: 32

```
gagctcatgg gtatacttag tcgtgg                                          26
```

<210> SEQ ID NO 33
<211> LENGTH: 30
<212> TYPE: DNA
<213> ORGANISM: Artificial Sequence
<220> FEATURE:
<223> OTHER INFORMATION: Synthetic sequence: NtATP6-TER primer IM366

<400> SEQUENCE: 33

```
ccgcggcgag gacctttata gccataattc                                      30
```

<210> SEQ ID NO 34
<211> LENGTH: 304
<212> TYPE: DNA
<213> ORGANISM: Nicotiana tabacum

<400> SEQUENCE: 34

```
atgggtatac ttagtcgtgg agcattccga gtatttgctt tagggatcgt tcctgcgcat      60
ctccttactt tatagcagtt attgctccgg ttccagaagg tatagctctc gcctcagctt     120
tttctttgaa atcggagact gttccaattt cctactgaga taggcaagcg agggagaac      180
tagacgtatc ttgctaggca aagacaggtt agaatggata gctcgcgggt gggattgacg     240
```

```
ggatagatca ctattgcaga aggaggtaga accgggggaa gaattatggc tataaaggtc      300
ctcg                                                                   304

<210> SEQ ID NO 35
<211> LENGTH: 717
<212> TYPE: DNA
<213> ORGANISM: Artificial Sequence
<220> FEATURE:
<223> OTHER INFORMATION: Synthetic sequence: Green fluorescent protein
      (GFP) sequence, Genbank accession number XXU70496

<400> SEQUENCE: 35
atgagtaaag gagaagaact tttcactgga gttgtcccaa ttcttgttga attagatggt       60
gatgttaatg ggcacaaatt ttctgtcagt ggagagggtg aaggtgatgc aacatacgga      120
aaacttaccc ttaaatttat ttgcactact ggaaaactac ctgttccatg gccaacactt      180
gtcactactt tcacttatgg tgttcaatgc ttttcaagat acccagatca tatgaagcgg      240
cacgacttct tcaagagcgc catgcctgag ggatacgtgc aggagaggac catctctttc      300
aaggacgacg ggaactacaa gacacgtgct gaagtcaagt ttgagggaga cacccctgtc      360
aacaggatcg agcttaaggg aatcgatttc aaggaggacg gaaacatcct cggccacaag      420
ttggaataca actacaactc ccacaacgta tacatcacgg cagacaaaca aaagaatgga      480
atcaaagcta acttcaaaat tagacacaac attgaagatg gaagcgttca actagcagac      540
cattatcaac aaaatactcc aattggcgat ggccctgtcc ttttaccaga caaccattac      600
ctgtccacac aatctgccct ttcgaaagat cccaacgaaa agagagacca catggtcctt      660
cttgagtttg taacagctgc tgggattaca catggcatgg atgaactata caaataa        717

<210> SEQ ID NO 36
<211> LENGTH: 1631
<212> TYPE: DNA
<213> ORGANISM: Artificial Sequence
<220> FEATURE:
<223> OTHER INFORMATION: Synthetic sequence: PCFM sequence

<400> SEQUENCE: 36
gaactcaatg gggccagtta tagcatcctg cttcttctta caaagaaat ttcataagat        60 aagagagatg aggcaaagaa ggaattgata gaggtgcggc gagaagttca ataccttctt      120
gatcgagaaa atgtccttgc ttgtacttct cttctttat cgagattggg ttggtgttca       180
gtgtaccgct tgtctagcct atgctttgca tgaacatctc aatgtccaag ataaaaagaa      240
cgaggggaag aatcgacgag gccagtgttc tcgaagagaa aatcgtgatg gaaaaagcgt      300
gaggagaatt cgaaactcga gatgttagaa ggtgcaaaat caatgggtgc aggagctgct      360
acaattgctt cagcgggagc tgctatcggt attggaaacg tccttagttc ctcgattcat      420
tccgttttag ggatacaaat aacagactta catcacgatg tcttttttctt cgttattctg      480 attttggttt tcgtatcatg gatcttgggt cgcgctttat ggcatttcca ctataaaaaa      540
aatccaatcc cgcaaaggat tgttcatgga actactatcg agattcttcg gaccttattt      600
cctagtatca tccctatgtt cattgctata ccatcatttg ccctgtatgg gtattcggac      660
tataacagtt ccgatgaaca gtcactcact tttgacagtt atacgattcc agaagatgat      720
ccagaattgg gtcaatcacg tttattagaa gtcgacaata gagtggttgt accagcaaac      780
agttctctcc gttttattgt aacatctgcg gctgtacctt ccttaggtgt caaaggtgat      840
gctgtgcctt ccttaggtgt caaaggtgat gctgtgcctt ccttaggtgt caaaggtgat      900
```

```
gctgtgcctg ggcctgggcg ggttttcag acttggaccc gagcttttga gcgtttgggc    960
ctgttgacgg ttgcccattg cgccggcacc ggaacatcaa gctcgggctc ggtagtcagt   1020
cttccacagg acgaaatatg ggccgcccett gagggcgatc cccaggccct tccggaagac   1080
gggcaatttc acgccgtcgc ccctgagggg aatcccagg cccttccgga agacgggcaa    1140
tttcacgccg tcgcccctga ggggaatccc caggcccttc cggaagacgg gcaatttcac   1200
gccgtcgccc ctgaggggaa tcccaggcc cttccggaag acgggcaatt tcacgccatc    1260
gcctttgacc ctcttatagc aacacggcaa gacgcgtgga atacgctact tgtcttgttg   1320
cggcgcagca ccaaaattga gcctaaggcc aattttgtta ctaaagcagg ggaagatctt   1380
ggtatagata ccgcagaccc tgttcgcctt gacaagttag tacgggtact gaacacgtat   1440
atccaactcg ccccattaga aagcgggaga aaggtcctcc aaaacctgaa agccacgatg   1500
gctgaatggg aaaagaacgg aaggccctaa gtggtgtcgt gtactttttt caattataat   1560
taaataaaag gaggttaccg aatttacgcg gtggcccttt tatgtatgtt gctgtcgtaa   1620
agtttcgttc t                                                         1631
```

<210> SEQ ID NO 37
<211> LENGTH: 34
<212> TYPE: DNA
<213> ORGANISM: Artificial Sequence
<220> FEATURE:
<223> OTHER INFORMATION: Synthetic sequence: Primer IM374

<400> SEQUENCE: 37
ttccgcggcc tatctcacat tcacccaatt gtca                                  34

<210> SEQ ID NO 38
<211> LENGTH: 45
<212> TYPE: DNA
<213> ORGANISM: Artificial Sequence
<220> FEATURE:
<223> OTHER INFORMATION: Synthetic sequence: Primer IM368

<400> SEQUENCE: 38
ttagaagtat ccaatgcaca gtaggtacca tgacaattgg gtgaa                       45

<210> SEQ ID NO 39
<211> LENGTH: 45
<212> TYPE: DNA
<213> ORGANISM: Artificial Sequence
<220> FEATURE:
<223> OTHER INFORMATION: Synthetic sequence: Primer IM369

<400> SEQUENCE: 39
attggatact tctaaggaag tccacacaaa tcaagaacca ttaga                       45

<210> SEQ ID NO 40
<211> LENGTH: 46
<212> TYPE: DNA
<213> ORGANISM: Artificial Sequence
<220> FEATURE:
<223> OTHER INFORMATION: Synthetic sequence: Primer IM370

<400> SEQUENCE: 40
ctcacattct tctgtttggt tagatgaaac gtctaatggt tcttga                      46

<210> SEQ ID NO 41
<211> LENGTH: 150
<212> TYPE: DNA
<213> ORGANISM: Artificial Sequence

```
<220> FEATURE:
<223> OTHER INFORMATION: Synthetic sequence: Primer Binding Domain MIT

<400> SEQUENCE: 41
tatctcacat tcacccaatt gtcatggtac ctactgtgca ttggatactt ctaaggaagt      60
ccacacaaat caagaaccat tagacgtttc atctaaccaa acagaagaat gtgagaaggc     120
ttccactaag gctaactctc aacagacaac                                      150

<210> SEQ ID NO 42
<211> LENGTH: 29
<212> TYPE: DNA
<213> ORGANISM: Artificial Sequence
<220> FEATURE:
<223> OTHER INFORMATION: Synthetic sequence: Primer IM267

<400> SEQUENCE: 42
atactcgagt ctctctctac tcctttcac                                        29

<210> SEQ ID NO 43
<211> LENGTH: 29
<212> TYPE: DNA
<213> ORGANISM: Artificial Sequence
<220> FEATURE:
<223> OTHER INFORMATION: Synthetic sequence: Primer IM268

<400> SEQUENCE: 43
atagcatgct gatggctgag atgccggtg                                        29

<210> SEQ ID NO 44
<211> LENGTH: 243
<212> TYPE: DNA
<213> ORGANISM: Nicotiana tabacum

<400> SEQUENCE: 44
tctctctcta ctcctttcac tctctctcta gccaaaccct ccaccatggc ttctcggagg      60
cttctcgcct ctctcctccg tcaatcggct caacgtggcg gcggtctaat tcccgatcg     120 ttaggaaact ccatccctaa atccgcttca cgcgcctctt cacgcgcatc ccctaaggga    180
ttcctcttaa accgcgccgt acagtacgct acctccgcag cggcaccggc atctcagcca    240
tca                                                                   243

<210> SEQ ID NO 45
<211> LENGTH: 2720
<212> TYPE: DNA
<213> ORGANISM: Artificial Sequence
<220> FEATURE:
<223> OTHER INFORMATION: Synthetic sequence: mRTRHi - Ty1 sequence

<400> SEQUENCE: 45
ctcgagtctc tctctactcc tttcactctc tctctagcca aaccctccac catggcttct      60
cggaggcttc tcgcctctct cctccgtcaa tcggctcaac gtggcggcgg tctaatttcc     120
cgatcgttag gaaactccat ccctaaatcc gcttcacgcg cctcttcacg cgcatcccct    180
aagggattcc tcttaaaccg cgccgtacag tacgctacct ccgcagcggc accggcatct    240
cagccatcag catgcatgaa caattcatcc cacaacatcg ttcctatcaa gactccaact    300
actgtttctg agcagaacac tgaagaatct atcatcgctg atcttccact tcctgatctt    360
cctccagaat ctcctactga atttcctgat ccattcaaag aacttccacc tatcaactca    420
agacaaacta actcttcatt gggcggaatt ggcgattcta atgcttacac tactatcaac    480
```

```
tctaagaaga ggtattgtag ccagcctcaa ccagtcttt tgctgttaca ttttcttggg      540
ctcatctaat gttattttcc tatttgttt tcaggtcact tgaagataat gaaactgaaa      600
tcaaagtttc tagggataca tggaatacta agaatatgag atcacttgaa cctccaagat    660
ctaagaagag aatccatctt attgcagctg ttaaagctgt gaaatcaatc aaaccaatta    720
gaacaactct tagatacgat gaagcaatta catacaacaa agacatcaag gagaaggaga    780
aatacatcga ggcttaccac aaagaagtta ccaacttct taagatgaaa acttgggata    840
ctgatgaata ctacgataga aaagagattg accctaagag agttatcaac tcaatgttca    900
tcttcaacaa gaagagagac ggaactcaca aagctagatt cgttgcaaga ggagatattc    960
agcatcctga cacttacgat tcaggtaagt attccaatgt tcttcgatta tgagtcaatg   1020
ttgttactgt atctgtctct gtggtttatt gtttcaggct tagttattga ttagtattga   1080
aacttcactc acatatttt tgtttgttt tctgaattgt gcaggtatgc aatctaatac    1140
tgttcatcac tacgcattga tgacatctct ttcacttgca ttggacaata actactacat   1200
tacacaactt gacatatctt ctgcatacct ttacgctgat atcaaggagg agctttacat   1260
tagacctcca ccacatttgg gaatgaatga taagttgatc cgtttgaaga aatcactta   1320 cggattgaaa caatctggag ctaattggta cgaaactatc aaatcatacc ttattcagca   1380
atgcggtatg gaggaagtta ggggatggtc atgcgtattc aagaactctc aagttacaat   1440
ctgcctcttc gttgatgata tggtgctctt ctctaagaat cttaactcaa caagagaat   1500 cattgagaag ttgaagatgc aatacgacac taagatcatc aaccttggag aatctgatga   1560
ggaaattcaa tacgacattc ttggattgga aatcaaatac caaagaggtg agttatattt   1620
aacagctcat cagttactta aacactttt gggacaagca gttcaaactc atgttccaat   1680
cctaaaatta attgcaattc acaggtaagt acatgaagtt gggaatggaa aactcattga   1740
ctgagaagat tcctaaactt aacgttcctt tgaatccaaa gggaagaaag ctctctgctc   1800
caggacaacc aggactttac attgaccagg atgaacttga gattgatgag gatgaataca   1860
aggagaaagt acacgagatg cagaagttga ttggacttgc ttcatacgtt ggatacaaat   1920
tcagattcga ccttctttac tacatcaaca cacttgctca gcatatactt ttcccatcta   1980
ggcaagttct tgacatgaca tacgagctta tccaattcat gtgggacact agagacaagc   2040
aactcatatg gcacaagaac aagcctacag agccagataa caagctcgtt gcaatctctg   2100
atgcttctta cggaaaccaa ccatactaca atcacaaat tggaaacatc tacttgctta   2160
acggaaaggt acttttctca aagactttac cttattgtgg aatattgaat tttctgaaag   2220
acttcacctt atctacattt gtaattttac tatggtaatc aggtgattgg aggaaagagc   2280
actaaggctt cacttacatg cacttcaact actgaggcag agatccacgc tatatcagaa   2340
tctgtaccac ttcttaacaa ccttttcttac cttatccaag agcttaacaa gaagccaatc   2400
atcaagggac ttcttactga ctcaagatca acaatctcta tcattaagtc tacaaatgaa   2460
gagaaattca gaaacagatt cttcggaaca aaggcaatga acttagaga tgaagtttca   2520 ggtaagtatt aacttaccaa atgatcaata ttattttgaa atgcaggttt tagaataata   2580
ctctctgccg ttcttgttta tttccaggta acaaccttta cgtttactac atcgagacta   2640
agaagaacat tgctgacgtt atgacaaagc ctcttcctat caagaccttc aagttgctta   2700
ctaacaaatg gattcattaa                                               2720
```

<210> SEQ ID NO 46
<211> LENGTH: 2576

<212> TYPE: DNA
<213> ORGANISM: Artificial Sequence
<220> FEATURE:
<223> OTHER INFORMATION: Synthetic sequence: mLTRASi sequence

<400> SEQUENCE: 46

```
ctcgagtctc tctctactcc tttcactctc tctctagcca aaccctccac catggcttct      60
cggaggcttc tcgcctctct cctccgtcaa tcggctcaac gtggcggcgg tctaatttcc     120
cgatcgttag gaaactccat ccctaaatcc gcttcacgcg cctcttcacg cgcatcccct     180
aagggattcc tcttaaaccg cgccgtacag tacgctacct ccgcagcggc accggcatct     240
cagccatcag catgcatgaa gccaacaatg gcaatcctcg aacgaatctc taagaactca     300
caggagaaca tcgacgaggt acaataaccc atatatatga attgattcat gtgttactcg     360
tacttgtttg aatatgtttg gagcaagttt gatactttg gatgatgata tcgcaaattc      420
gttatctttt tggcgttata ggtcttcaca agactttacc gttaccttct ccgtcctgac     480
atctactacg tggcatatca gaacctctac tctaacaagg gagcttctac aaagggaatc     540
ctcgatgata cagctgatgg attctctgag gagaagatca agaagatcat ccaatctttg     600
aaggacggaa cttactaccc tcagcctgtc cgaagaatgt acatcgcaaa gaagaactct     660
aagaagatga gacctcttgg aatcccaact ttcacagaca gttgatcca ggaggctgtg      720
agaatcatcc ttgaatctat ctatgagcct gtcttcgagg atgtgtctca cggtttccga     780
cctcagcgaa gctgtcacac agctttgaag acaatcaaga gagagttcgg aggtaaatta     840
tatgctttgc cacttcctca aaagatcatt ttaggttcat tggtatgtgg ttttttttctt     900
aacaggtgca agatggttcg tggagggaga tatcaaggga tgcttcgata acatcgacca     960
cgtcacactc atcggactca tcaaccttaa gatcaaggat atgaagatga gccagttgat    1020
ctacaagttc ctcaaggcag gttacctcga aaactggcag taccacaaga cttacagcgg    1080
aacacctcag ggcggaatcc tctctcctct cctcgctaac atctatcttc atgaattgga    1140
caagttcgtt ctccaactca gatgaagtt cgaccgagag agtccagaga gaatcacacc     1200
tgaataccgg gagcttcaca acgagatcaa aagaatctct caccgtctca agaagttgga    1260
gggcgaggag aaggctaagg ttctcttgga ataccaggag aagaggaaga ggttgcctac    1320
actcccttgt acatcacaaa caaacaaggt tcgttctctc cattttcatt cgtttgagtc    1380
tgatttagtg ttttgtggtt gatctgaatc gatttattgt tgattagtga atcaatttga    1440
ggctgtgtcc taatgttttg actttgatt acaggtcttg aagtacgtcc gatacgctga     1500
cgacttcatc atctctgtta agggaagcaa ggaggactgt caatggatca aggagcaatt    1560
gaagctcttc atccataaca agctcaagat ggaattgagt gaggagaaga cactcatcac    1620
acatagcagt cagcctgctc gtttcctcgg atacgcatc cgagtcagga gaagtggaac     1680
tatcaagcga tctggaaagg ttcaattctt tctttcacat ttgtacttgt tcactcgttt    1740
tattaatcct ctttagaatg gagattctta cctctgtgtg gcctttggca ggtcaagaag    1800
agaacactca acgggagtgt ggagcttctc atccctctcc aagacaagat ccgtcaattc    1860
atcttcgaca gaagatcgc tatccagaag aaggatagct catggttccc agttcacagg    1920
aagtacctta tccgttcaac agacttggag atcatcacaa tctacaactc tgaattgaga    1980
ggtaagctgc tacctcaaac tttctagtgc ttccatattt cctttcttct gcaaggcaga    2040
gaaccattgt ggtaagtgt tttaaattgt gaatgtatag gtatctgcaa ctactacggt     2100
ctcgcaagta acttcaacca gctcaactac ttcgcttacc ttatggaata ctcttgcttg    2160
```

```
aagactatcg catctaagca taagggaaca ctctcaaaga ccatctctat gttcaaggat    2220
ggaagtggtt cttggggaat cccttacgag atcaagcagg ggaagcagag gagatacttc   2280
gccaacttca gtgaatgcaa atctccttac caattcactg atgagatcag tcaagctcct   2340
gtgctttacg gatacgctcg gaacactctt gagaacagac ttaaggctaa gtgttgtgag   2400
ctttgtggaa catctgatga gaacacatct tacgagatcc accacgtcaa caaggtcaag   2460
aaccttaagg gaaaggagaa gtgggagatg gcaatgatcg ctaagcagcg gaagactctt   2520
gttgtttgct tccattgtca tcgtcacgtg atccataagc acaagtgaac tagtaa       2576
```

<210> SEQ ID NO 47
<211> LENGTH: 35
<212> TYPE: DNA
<213> ORGANISM: Artificial Sequence
<220> FEATURE:
<223> OTHER INFORMATION: Synthetic sequence: Primer IM326

<400> SEQUENCE: 47

```
cgaagcttga attctaccgg atttggagcc aagtc                               35
```

<210> SEQ ID NO 48
<211> LENGTH: 42
<212> TYPE: DNA
<213> ORGANISM: Artificial Sequence
<220> FEATURE:
<223> OTHER INFORMATION: Synthetic sequence: Primer IM327

<400> SEQUENCE: 48

```
aaggatcctc tagatgtttg gtgacctgaa ataaaacaat ag                       42
```

<210> SEQ ID NO 49
<211> LENGTH: 1738
<212> TYPE: DNA
<213> ORGANISM: Arabidopsis thaliana

<400> SEQUENCE: 49

```
taccggattt ggagccaagt ctcataaacg ccattgtgga agaaagtctt gagttggtgg    60
taatgtaaca gagtagtaag aacagagaag agagagagtg tgagatacat gaattgtcgg    120
gcaacaaaaa tcctgaacat cttattttag caaagagaaa gagttccgag tctgtagcag    180
aagagtgagg agaaatttaa gctcttggac ttgtgaattg ttccgcctct tgaatacttc    240
ttcaatcctc atatattctt cttctatgtt acctgaaaac cggcatttaa tctcgcgggt    300
ttattccggt tcaacatttt ttttgttttg agtattatc tgggcttaat aacgcaggcc    360
tgaaataaat tcaaggccca actgtttttt tttttaagaa gttgctgtta aaaaaaaaa    420 aagggaatta acaacaacaa caaaaaaaga taaagaaaat aataacaatt actttaattg    480
tagactaaaa aaacatagat tttatcatga aaaaagaga aagaaataa aaacttggat     540 caaaaaaaaa acatacagat cttctaatta ttaacttttc ttaaaaatta ggtccttttt    600
cccaacaatt aggtttagag ttttggaatt aaaccaaaaa gattgttcta aaaaatactc    660
aaatttggta gataagtttc cttatttttaa ttagtcaatg gtagatactt ttttttcttt    720
tctttattag agtagattag aatcttttat gccaagtatt gataaattaa atcaagaaga    780
taaactatca taatcaacat gaaattaaaa gaaaaatctc atatatagta ttagtattct    840
ctatatatat tatgattgct tattcttaat gggttgggtt aaccaagaca tagtcttaat    900
ggaaagaatc tttttttgaac ttttttcctta ttgattaaat tcttctatag aaaagaaaga    960
aattatttga ggaaaagtat atacaaaaag aaaaatagaa aaatgtcagt gaagcagatg   1020
```

```
taatggatga cctaatccaa ccaccaccat aggatgtttc tacttgagtc ggtcttttaa      1080
aaacgcacgg tggaaaatat gacacgtatc atatgattcc ttcctttagt ttcgtgataa      1140
taatcctcaa ctgatatctt cctttttttg ttttggctaa agatatttta ttctcattaa      1200
tagaaaagac ggttttgggc ttttggtttg cgatataaag aagaccttcg tgtggaagat      1260
aataattcat cctttcgtct ttttctgact cttcaatctc tcccaaagcc taaagcgatc      1320
tctgcaaatc tctcgcgact ctctctttca aggtatattt tctgattctt tttgtttttg      1380
attcgtatct gatctccaat ttttgttatg tggattattg aatcttttgt ataaattgct      1440
tttgacaata ttgttcgttt cgtcaatcca gcttctaaat tttgtcctga ttactaagat      1500
atcgattcgt agtgtttaca tctgtgtaat ttcttgcttg attgtgaaat taggattttc      1560
aaggacgatc tattcaattt ttgtgttttc tttgttcgat tctctctgtt ttaggtttct      1620
tatgtttaga tccgtttctc tttggtgttg ttttgatttc tcttacggct tttgatttgg      1680
tatatgttcg ctgattggtt tctacttgtt ctattgtttt atttcaggtc accaaaca        1738
```

<210> SEQ ID NO 50
<211> LENGTH: 838
<212> TYPE: DNA
<213> ORGANISM: Artificial Sequence
<220> FEATURE:
<223> OTHER INFORMATION: Synthetic sequence: 35S-PRO sequence, based on
      GenBank accession number AF502128

<400> SEQUENCE: 50

```
ttagcctttt caatttcaga aagaatgcta acccacagat ggttagagag gcttacgcag       60
caggtctcat caagacgatc tacccgagca ataatctcca ggaaatcaaa taccttccca      120
agaaggttaa agatgcagtc aaaagattca ggactaactg catcaagaac acagagaaag      180
atatatttct caagatcaga agtactattc agtatggac gattcaaggc ttgcttcaca       240
aaccaaggca gtaatagag attggagtct ctaaaaaggt agttcccact gaatcaaagg       300
ccatggagtc aaagattcaa atagaggacc taacagaact cgccgtaaag actggcgaac      360
agttcataca gagtctctta cgactcaatg acaagaagaa aatcttcgtc aacatggtgg      420
agcacgacac acttgtctac tccaaaaata tcaaagatac agtctcagaa gaccaaaggg      480
caattgagac ttttcaacaa agggtaatat ccggaaacct cctcggattc cattgcccag      540
ctatctgtca ctttattgtg aagatagtgg aaaaggaagg tggctcctac aaatgccatc      600
attgcgataa aggaaaggcc atcgttgaag atgcctctgc cgacagtggt cccaaagatg      660
gacccccacc cacgaggagc atcgtggaaa aagaagacgt tccaaccacg tcttcaaagc      720
aagtggattg atgtgatatc tccactgacg taagggatga cgcacaatcc cactatcctt      780
cgcaagaccc ttcctctata taaggaagtt catttcattt ggagagaaca cgggggac        838
```

<210> SEQ ID NO 51
<211> LENGTH: 1102
<212> TYPE: DNA
<213> ORGANISM: Artificial Sequence
<220> FEATURE:
<223> OTHER INFORMATION: Synthetic sequence: TAF2 promoter sequence,
      based on sequence At1g73965 from the Arabidopsis genome

<400> SEQUENCE: 51

```
ggtaccatga tcgcttcatg ttttttatcta atttgttagc atattgaatg attgattttc       60
ttttaatttg gatatgttga ttgtcttgtt gcatcatcaa tgtatgtttt atttaacacc      120
```

```
ggaagatctt atgatgggtt cattacttca taataatctc cgagttctac aagactacaa      180
ctttcacgtg acttttacag cgacaaaaaa tgcatctagc gaaaattaat ccacaaccta      240 tgcattttg tcactcttca cacgcgtatg tgcataaata tatagtatat actcgacaat       300
cgatgcgtat gtgtacacaa ttaccaaaac aattatttga atattcagac atgggttgac      360
atcaccaagt aatattcaca gtatctgaaa actatgtttt gacatcccta aatagtttga      420
ctaaccagtt taatatgaga gcatttgtaa gaggcaagag ccatggtttt gttggctcgt      480
ttaatatgct catttaaccc ccccaaaaaa tactattaga tttaaacgta aaagaattaa      540
cgaacacaag aactgctaaa acaaaaaaaa atcaatggcc gacatttcat agttcataca      600
tcactaatac taaaagatgc atcatttcac tagggtctca tgaaatagga gttgacattt      660 tttttttgtaa cgacagaagt tgacatgtta agcatcaatt ttttttaagag tggattatac    720 tagttttttt ttttttttttt aatgtatggt atgatacaac aacaaaaact ataaaataga    780
aaaagtcagt gaaaccctcaa attgaaggaa aaacttttgc acaaaaagag agagagagag     840
aaagaatgta aatccaaata aatgggccta attgagaatg ctttaacttt ttttttttgg     900
ctaaaagaga atgctttaac taagcccata aaatgaacat caaactcaaa gggtaagatt      960
aatacattta gaaaacaata gccgaatatt taataagttt aagacataga ggagttttat     1020
gtaatttagg aaccgatcca tcgttggctg tataaaaagg ttacatctcc ggctaacata    1080
tcggcaaaaa aggaacctcg ag                                              1102

<210> SEQ ID NO 52
<211> LENGTH: 276
<212> TYPE: DNA
<213> ORGANISM: Artificial Sequence
<220> FEATURE:
<223> OTHER INFORMATION: Synthetic sequence: nos terminator sequence,
      based on GenBank sequence accession EU048864

<400> SEQUENCE: 52
tctagagtca agcagatcgt tcaaacattt ggcaataaag tttcttaaga ttgaatcctg       60
ttgccggtct tgcgatgatt atcatataat ttctgttgaa ttacgtgaag catgtaataa     120
ttaacatgta atgcatgacg ttatttatga gatgggtttt tatgattaga gtcccgcaat     180
tatacattta atacgcgata gaaaacaaaa tatagcgcgc aaactaggat aaattatcgc     240
gcgcggtgtc atctatgtta ctagatcgac ctgcag                               276

<210> SEQ ID NO 53
<211> LENGTH: 406
<212> TYPE: DNA
<213> ORGANISM: Artificial Sequence
<220> FEATURE:
<223> OTHER INFORMATION: Synthetic sequence: ags terminator sequence,
      based on GenBank sequence EU181145

<400> SEQUENCE: 53
gaattaacag aggtggatgg acagacccgt tcttacaccg gactgggcgc gggataggat       60
attcagattg ggatgggatt gagcttaaag ccggcgctga gaccatgctc aaggtaggca     120
atgtcctcag cgtcgagccc ggcatctatg tcgagggcat tggtggagcg cgcttcgggg     180
ataccgtgct tgtaactgag accggatatg aggccctcac tccgcttgat cttggcaaag     240
atatttgacg catttattag tatgtgttaa ttttcatttg cagtgcagta ttttctattc     300
gatctttatg taattcgtta caattaataa atattcaaat cagattattg actgtcattt     360
gtatcaaatc gtgtttaatg gatatttta ttataatatt gatgat                    406
```

<210> SEQ ID NO 54
<211> LENGTH: 27
<212> TYPE: DNA
<213> ORGANISM: Artificial Sequence
<220> FEATURE:
<223> OTHER INFORMATION: Synthetic sequence: Primer AS912

<400> SEQUENCE: 54
gccgcggctt tattaccgtg aatatta                                    27

<210> SEQ ID NO 55
<211> LENGTH: 30
<212> TYPE: DNA
<213> ORGANISM: Artificial Sequence
<220> FEATURE:
<223> OTHER INFORMATION: Synthetic sequence: Primer AS913

<400> SEQUENCE: 55
cgcggccgct ctgataagtg caacctgatt                                 30

<210> SEQ ID NO 56
<211> LENGTH: 333
<212> TYPE: DNA
<213> ORGANISM: Nicotiana tabacum

<400> SEQUENCE: 56
ctttattacc gtgaatatta ttttggtaag gggtttattc ccaacaactg gtatcagagc    60
acaggttctg ctcgttcact gaaatactat tcactgtcgg tagtactata cttggtgaaa   120
aataaaaatg tctggagtaa agtacgaggt agcaaaattc aatggagata acggtttctc   180
aacatggcaa agaaggatga gagatctgct catccaacaa ggattacaca aggttctaga   240
tgttgattcc aaaaagcctg ataccatgaa agctgaggat tgggctgact tggatgaaag   300
agctgctagt gcaatcaggt tgcacttatc aga                               333

<210> SEQ ID NO 57
<211> LENGTH: 26
<212> TYPE: DNA
<213> ORGANISM: Artificial Sequence
<220> FEATURE:
<223> OTHER INFORMATION: Synthetic sequence: Primer IM416

<400> SEQUENCE: 57
ggatccatat cgagccattg aagcag                                     26

<210> SEQ ID NO 58
<211> LENGTH: 23
<212> TYPE: DNA
<213> ORGANISM: Artificial Sequence
<220> FEATURE:
<223> OTHER INFORMATION: Synthetic sequence: Primer IM417

<400> SEQUENCE: 58
gcatgctcaa tcttgtccct tgg                                        23

<210> SEQ ID NO 59
<211> LENGTH: 925
<212> TYPE: DNA
<213> ORGANISM: Oryza sativa

<400> SEQUENCE: 59
ggattcatat cgagccattg aagcagcgcg tcgggctaca atcgggcaat tccatcgtgc    60

-continued

```
tatgagcgga caattccgaa gaaattgtaa gatatgggta agagttctcg cagatcttcc      120
tattacgggg aaacccgcag aagttcgaat gggaagagga aaaggaaatc ctacgggttg      180
gattgctcgt gtgtccacgg gacaaatccc atttgaaatg gatggtgtga gtttgtcaaa      240
tgctcgacaa gccgctagat tagcggcgca taaaccatgt tcgtcaacca agtttgttca      300
gtggtcgtaa cgtaattggt tagtggggaa aaaccgggcc gggactcaaa agaatttggc      360
gaagtgtttg ttcctgaacg agggaagtgg aagacaaag agggatagg agctcgcctc       420 cttcttttt tgaatcgccg aaattgtacg acgacccttc ttgttccagg catacgactc       480
tgagacgtga cggtgtcact tttccggccc ggtaaagtga cagttatata aataagaata     540
agaaagagaa gcgtgatgtt gtcagcaatc aaattatcgt aaatagatag tacggttgcg     600
ttgtttcaat ttctgttcgt cggtccttgg gttacgaagg tgtgggctta ctaatacgga     660
gagggttccg aatgataaag tgtcatgaaa gttcgtgaaa gaatgttctt gttttcgtt      720 ggaaacccca acgccacggc cacaaaacga aaaagtctcc cgtttgtttt gggagcagag     780 cttttaaaagg atatagttac cctatgatga gatttagttc aacggataag aaggatagaa    840
gaaatatgct atttgctgct attccatcta tttgtgcatt cagtgctgcc gttccccggg    900
ccccaaagga caagattgag catgc                                            925
```

```
<210> SEQ ID NO 60
<211> LENGTH: 24
<212> TYPE: DNA
<213> ORGANISM: Artificial Sequence
<220> FEATURE:
<223> OTHER INFORMATION: Synthetic sequence: Primer IM418

<400> SEQUENCE: 60
ttctagagtc gccgctatca cttt                                              24

<210> SEQ ID NO 61
<211> LENGTH: 26
<212> TYPE: DNA
<213> ORGANISM: Artificial Sequence
<220> FEATURE:
<223> OTHER INFORMATION: Synthetic sequence: Primer IM419

<400> SEQUENCE: 61
ccgcggctaa gactatagaa tgttcc                                            26

<210> SEQ ID NO 62
<211> LENGTH: 859
<212> TYPE: DNA
<213> ORGANISM: Oryza sativa

<400> SEQUENCE: 62
ttctagagtc gccgctatca ctttttttgg ggggccaatc ccgcgaagag ttatggaaag       60
attttatagc tcaattgaat gaagaaagtg aattcatgga caacattttt tttggtgttt     120
acaacgcgag aaacggctat gaaagcgcca cagttcttca gggaatacgg atagatttag     180
cgataaacgg ctatgaaagt gcatttttgt cggaatttgc acctatttgt atctatttag     240
tgatcagtcc gctagtttct ttgattccac tcgtgttcc ttttccattt gcttccaata      300
gttcgaccta tccagaaaaa ttgtcggcct acgaatgtgg tttcgatccc tccggtgatg     360
ccagaagtcg tttcgatata cgattttatc cggttcctat tttatttatt atccctgatc     420
tggaagtcac ctttttttt ccttgggcag tacctcctaa caagattgat ctgtttggat      480
cttggtccat gatggccttt ttattgattt tgacgattgg atttctctat gaatggaaaa     540
```

```
ggggtgcttc ggatcgggag taaccactag tgaaagggca aaggggggaa ggacatagga      600
aagagggatg cctacaaaaa atcaattgat tcgtcatggt agagaagaaa aacagcgcac      660
ggaccgtact cgagcttcgg atcaatgtcc ccaaaagcaa ggagtatgcc tgcgtgtttc      720
gacgagaaca ccgaaaaaac ctaattcagc tctacgtaag atagcaaaag tacggttgag      780
caatcgacat gatatatttg ctcacattcc aggcgaaggt cataattcgc aggaacattc      840
tatagtctta gccgcggcc                                                   859

<210> SEQ ID NO 63
<211> LENGTH: 22
<212> TYPE: DNA
<213> ORGANISM: Artificial Sequence
<220> FEATURE:
<223> OTHER INFORMATION: Synthetic sequence: Primer ARP1

<400> SEQUENCE: 63
gtcattcata tgcttgagaa ga                                               22

<210> SEQ ID NO 64
<211> LENGTH: 22
<212> TYPE: DNA
<213> ORGANISM: Artificial Sequence
<220> FEATURE:
<223> OTHER INFORMATION: Synthetic sequence: Primer ARP2

<400> SEQUENCE: 64
gcctacaaaa aagctccgca cg                                               22

<210> SEQ ID NO 65
<211> LENGTH: 1366
<212> TYPE: DNA
<213> ORGANISM: Oryza sativa

<400> SEQUENCE: 65
gtcattcata tgcttgagaa gagagtcggg atagtccaaa ataaaacaaa ggtaagatta      60
cctggtcaaa agtgaaaaca tcagttaaaa ggtggtataa gtaaaatatc ggtaataaaa     120
ggtggcccaa agtgaaattt actcttttct actattataa aaattgagga tgttttgtcg     180
gtactttgat acgtcatttt tgtatgaatt ggttttttaag tttattcgcg atttggaaat     240
gcatatctgt atttgagtcg ttttttaagt tcgttgcttt tgtaaataca gagggatttg     300
tataagaaat atctttaaaa aacccatatg ctaatttgac ataatttttg agaaaaatat     360
atattcaggc gaattccaca atgaacaata ataagattaa aatagcttgc ccccgttgca     420
gcgatgggta ttttttctag taaaataaaa gataaactta gactcaaaac atttacaaaa     480 acaacccta aagtcctaaa gcccaaagtg ctatgcacga tccatagcaa gcccagccca      540
acccaaccca acccaaccca ccccagtgca gccaactggc aaatagtctc cacccccggc     600
actatcaccg tgagttgtcc gcaccaccgc acgtctcgca gccaaaaaaa aaaaaagaaa     660 gaaaaaaag aaaagaaaa acagcaggtg ggtccgggtc gtgggggccg gaaaagcgag       720
gaggatcgcg agcagcgacg aggcccggcc ctccctccgc ttccaaagaa acgccccca      780 tcgccactat atacataccc ccccctctcc tccatcccc caacccta caccaccacc         840 accaccacct cctcccccct cgctgccgga cgacgagctc ctccccccctc cccctccgcc    900 gccgccggta accaccccgc ccctctcctc tttctttctc cgttttttttt ttcgtctcgg    960 tctcgatctt tggccttggt agtttgggtg ggcgagagcg gcttcgtcgc ccagatcggt    1020
```

-continued

```
gcgcgggagg ggcgggatct cgcggctggc gtctccgggc gtgagtcggc ccggatcctc    1080
gcggggaatg gggctctcgg atgtagatct gcgatccgcc gttgttgggg gagatgatgg    1140
ggggtttaaa atttccgcca tgctaaacaa gatcaggaag aggggaaaag ggcactatgg    1200
tttatatttt tatatatttc tgctgcttcg tcaggcttag atgtgctaga tcttctttct    1260
ttcttctttt tgtggtagaa tttgaatccc tcagcattgt tcatcggtag ttttctttt    1320 catgatttgt gacaaatgca gcctcgtgcg gagctttttt gtaggc                   1366
```

```
<210> SEQ ID NO 66
<211> LENGTH: 20
<212> TYPE: DNA
<213> ORGANISM: Artificial Sequence
<220> FEATURE:
<223> OTHER INFORMATION: Synthetic sequence: Primer ntLFS3F

<400> SEQUENCE: 66
cccaagttac agcgggctct                                                 20

<210> SEQ ID NO 67
<211> LENGTH: 20
<212> TYPE: DNA
<213> ORGANISM: Artificial Sequence
<220> FEATURE:
<223> OTHER INFORMATION: Synthetic sequence: Primer PCFMR (for tobacco)

<400> SEQUENCE: 67
tatggggctt ccctgtcgag                                                 20

<210> SEQ ID NO 68
<211> LENGTH: 20
<212> TYPE: DNA
<213> ORGANISM: Artificial Sequence
<220> FEATURE:
<223> OTHER INFORMATION: Synthetic sequence: Primer PCFMF (for tobacco)

<400> SEQUENCE: 68
gcagcaccaa aattgagcct                                                 20

<210> SEQ ID NO 69
<211> LENGTH: 20
<212> TYPE: DNA
<213> ORGANISM: Artificial Sequence
<220> FEATURE:
<223> OTHER INFORMATION: Synthetic sequence: Primer ntRFS3R

<400> SEQUENCE: 69
cgagttccag aggcatcttc                                                 20

<210> SEQ ID NO 70
<211> LENGTH: 20
<212> TYPE: DNA
<213> ORGANISM: Artificial Sequence
<220> FEATURE:
<223> OTHER INFORMATION: Synthetic sequence: Primer osLFSF

<400> SEQUENCE: 70
actgaatgcg gaaagtatgg                                                 20

<210> SEQ ID NO 71
<211> LENGTH: 20
<212> TYPE: DNA
<213> ORGANISM: Artificial Sequence
<220> FEATURE:
<223> OTHER INFORMATION: Synthetic sequence: Primer PCFMR (for rice)
```

```
<400> SEQUENCE: 71
tatggggctt ccctgtcgag                                              20

<210> SEQ ID NO 72
<211> LENGTH: 20
<212> TYPE: DNA
<213> ORGANISM: Artificial Sequence
<220> FEATURE:
<223> OTHER INFORMATION: Synthetic sequence: Primer PCFMF (for rice)

<400> SEQUENCE: 72
gcagcaccaa aattgagcct                                              20

<210> SEQ ID NO 73
<211> LENGTH: 20
<212> TYPE: DNA
<213> ORGANISM: Artificial Sequence
<220> FEATURE:
<223> OTHER INFORMATION: Synthetic sequence: Primer osRFSR

<400> SEQUENCE: 73
tagggctact agaaagagga                                              20
```